US010383918B2

(12) United States Patent  
Geissler et al.

(10) Patent No.: US 10,383,918 B2  
(45) Date of Patent: Aug. 20, 2019

(54) COMPOSITIONS IN THE FORM OF AN INJECTABLE AQUEOUS SOLUTION COMPRISING HUMAN GLUCAGON AND A STATISTICAL CO-POLYAMINO ACID

(71) Applicant: ADOCIA, Lyons (FR)

(72) Inventors: Alexandre Geissler, Lyons (FR); Ségolène Laage, Lyons (FR); Olivier Soula, Meyzieu (FR); David Duracher, Lyons (FR); Grégory Meiffren, Meyzieu (FR)

(73) Assignee: ADOCIA, Lyons (FR)

( * ) Notice: Subject to any disclaimer, the term of this patent is extended or adjusted under 35 U.S.C. 154(b) by 22 days.

(21) Appl. No.: 15/616,542

(22) Filed: Jun. 7, 2017

(65) Prior Publication Data

US 2017/0348394 A1 Dec. 7, 2017

(30) Foreign Application Priority Data

Jun. 7, 2016 (FR) ..................................... 16 55221  
Jan. 10, 2017 (FR) ..................................... 17 50221

(51) Int. Cl.
| A61K 38/26 | (2006.01) |
| A61K 9/00 | (2006.01) |
| A61K 9/08 | (2006.01) |
| A61K 47/34 | (2017.01) |

(52) U.S. Cl.  
CPC ............ *A61K 38/26* (2013.01); *A61K 9/0019* (2013.01); *A61K 9/08* (2013.01); *A61K 47/34* (2013.01)

(58) Field of Classification Search  
CPC ........ A61K 47/34; A61K 9/08; A61K 9/0019; A61K 47/36; A61K 38/28  
See application file for complete search history.

(56) References Cited

U.S. PATENT DOCUMENTS

| 6,384,016 B1 | 5/2002 | Kaarsholm |
| 2006/0099264 A1 | 5/2006 | Chan et al. |
| 2011/0097386 A1 | 4/2011 | Steiner et al. |
| 2013/0178415 A1 | 7/2013 | Soula |
| 2015/0291680 A1 | 10/2015 | Ward et al. |

FOREIGN PATENT DOCUMENTS

| FR | 2 801 226 A1 | 5/2001 |
| FR | 2 840 614 A1 | 12/2003 |
| GB | 1202607 | 8/1970 |
| WO | 01/37809 A1 | 5/2001 |
| WO | 2011/138802 A1 | 11/2011 |
| WO | 2012/059764 A1 | 5/2012 |
| WO | 2013/101749 A1 | 7/2013 |
| WO | 2014/096440 A2 | 6/2014 |
| WO | 2015/095389 A1 | 6/2015 |

OTHER PUBLICATIONS

Timothy J. Deming, "Facile Synthesis of Block Copolypeptides of Defined Architecture" Nature, (1997) vol. 390, pp. 386-389.  
Hua Lu et al., "N-Trimethylsilyl Amines for Controlled Ring-Opening Polymerization of Amino Acid N-Carboxyanhydrides and Facile End Group Functionalization of Polypeptides" J. Am. Chemical Society, vol. 130, No. 38, (2008) pp. 12562-12563.  
Hua Lu et al., "Hexamethyldisilazane-Mediated Controlled Polymerization of a-Amino Acid N-Carboxyanhydrides" J. Am. Chemical Society, vol. 129, No. 46, (2007) pp. 14114-14115.  
Timothy J. Deming, "Polypeptide and Polypeptide Hybrid Copolymer Synthesis Via NCA Polymerization" Advance Polymerization Science (2006) vol. 202, pp. 1-18.  
Subramanian, et al., "Structure of Complexes of Cationic Lipids and Poly(Glutamic Acid) Polypeptides: A Pinched Lamellar Phase," J. Am. Chem. Soc., vol. 122, 2000, pp. 26-34.  
Naiki, et al., "Fluorometric Determination of Amyloid Fibrils in Vitro Using the Flurorescent Dye, Thiotlavine T," Analytical Biochemistry, vol. 177, 1989, pp. 244-249.  
Harry LeVine III, "Quantification of ß-Sheet Amyloid Fibril Structures with Thiotlavin T," Methods in Enzymology, vol. 309, 1999, pp. 274-284.  
Aug. 9, 2017 International Search Report filed in Patent Application No. PCT/EP2017/063888.  
Aug. 9, 2017 International Search Report filed in Patent Application No. PCT/EP2017/063887.  
U.S. Appl. No. 15/616,627, filed Jun. 7, 2017 in the name of Alexandre Geissler.  
Onoue et al., "Mishandling of the Therapeutic Peptide Glucagon Generates Cytotoxic Amyloidogenic Fibrils," Pharmaceutical Research, vol. 21, No. 7, Jul. 2004, pp. 1274-1283.  
Kirsch, et al., "The degradation pathways of glucagon in acidic solutions," International Journal of Pharmaceutics, vol. 203, 2000, pp. 115-125.  
Jackson et al., "Stable Liquid Glucagon Formulations for Rescue Treatment and Bi-Hormonal Closed-Loop Pancreas," Curr Diab Rep 2012, vol. 12, pp. 705-710.  
Matilainen et al., "The Effect of Cyclodextrins of Chemical and Physical Stability of Glucagon and Characterization of Glucagon/y-CD Inclusion Complexes," Journal of Pharmaceutical Sciences, vol. 97, No. 7, Jul. 2008, pp. 2720-2729.  
Matilainen et al., "The stability and dissolution properties of Solid glucagon/y-cyclodextrin powder," European Journal of Pharmaceutical Sciences 2009, vol. 36, pp. 412-420.  
Garay et al., "Antibodies against polyethylene glycol in healthy subjects and in patients treated with PEG-conjugated agents," Expert Opinion Drug Deliv. 2012, vol. 9, pp. 1319-1323.  
Ganson et al., "Pre-existing anti-polyethylene glycol antibody linked to first-exposure allergic reactions to pegnivacogin, a PEGylated RNA aptamer," J. Allergy Clin. Immunol 2016, doi:10.1016/j.jac.2015.10.034.

(Continued)

*Primary Examiner* — Sudhakar Katakam  
(74) *Attorney, Agent, or Firm* — Oliff PLC

(57) ABSTRACT

Physically stable compositions in the form of an injectable aqueous solution, the pH of which is from 6.0 to 8.0, includes at least: a) human glucagon, and b) a co-polyamino acid bearing carboxylate charges and hydrophobic radicals Hy. In an embodiment, the compositions include, in addition, a gastrointestinal hormone.

15 Claims, No Drawings

(56) References Cited

OTHER PUBLICATIONS

Tan et al., "Coadministration of Glucagon-Like Peptide-1 During Glucagon Infusion in Humans Results in Increased Energy Expenditure and Amelioration of Hyperglycemia," Diabetes, vol. 62, Apr. 2013, pp. 1131-1138.
Sep. 27, 2018 Office Action issued in U.S. Appl. No. 15/616,627.

COMPOSITIONS IN THE FORM OF AN INJECTABLE AQUEOUS SOLUTION COMPRISING HUMAN GLUCAGON AND A STATISTICAL CO-POLYAMINO ACID

Human glucagon is a short-acting hyperglycemic hormone which makes it impossible to increase glycemia, thus correcting a hypoglycemic level that can result from an insulin excess. It enables the release of glucose by stimulation of hepatic glycogenolysis and it has insulin antagonistic properties (hypoglycemic). Human glucagon is normally secreted by the alpha cells of the islets of Langerhans in the pancreas when hypoglycemia is detected.

Human glucagon is used for therapeutic purposes, such as the emergency treatment of severe hypoglycemia, also referred to as "rescue," but also in a diagnostic context in the performance of medical examinations, for example, in order to inhibit gastrointestinal motility. Other applications are also considered for human glucagon, in particular its use in a bi-hormonal glycemia regulation system, also referred to as artificial pancreas, and in congenital hyperinsulinism, which is a rare disease characterized by very high insulin levels.

The clinical use of human glucagon has been limited because of some of its disadvantageous properties in terms of development of a stable pharmaceutical product with therapeutic intent. Indeed, human glucagon has a very low solubility at physiological pH and a high physical instability, due to its propensity to form fibrils in a large pH range. This is the reason why the only commercial products based on human glucagon (Glucagen®, NOVO NORDISK and Glucagon for injection, ELI LILLY) are lyophilized forms to be reconstituted extemporaneously.

The studies of Onoue t al. (Pharm. Res. 2004, 21(7), 1274-83) have shown the potentially dangerous characters of these fibrils: fibrillated human glucagon being cytotoxic in mammalian cells in culture.

In addition to its physical instability, human glucagon undergoes various types of chemical degradation. In an aqueous solution, it degrades rapidly to form several degradation products. At least 16 degradation products of human glucagon have been identified by Kirsh et al. (International Journal of Pharmaceutics, 2000, 203, 115-125). The chemical degradation of this human glucagon is thus rapid and complex.

The poor chemical and physical stability of human glucagon in solution has led pharmaceutical companies such as NOVO NORDISK, ELI LILLY and more recently FRESENIUS KABI to market this human glucagon in the form of a lyophilizate to be reconstituted at acidic pH (pH<3) immediately before injection. Human glucagon in lyophilizate form is more stable, and the preparation of the formulation at acidic pH immediately before use makes it possible to obtain a clear solution. However, once the product is reconstituted, it has to be used rapidly, because it undergoes an extremely rapid chemical and physical degradation in the acidic reconstitution buffer, with appearance of human glucagon fibrils within 24 hours after the reconstitution and/or gelling of the composition. However, this presentation of the product is unsatisfactory because it requires a very rapid use of the formulation. This instability not only makes it impossible to use it in a pump, but it also presents the disadvantage of leading to large product losses in diagnostic use. In fact, since a composition of this type is no longer usable a few hours after its preparation, this leads to wastage.

Finally, even in the application of an emergency treatment for severe hypoglycemic reactions that can occur during insulin therapy in diabetic patients, the formulation to be reconstituted is also not ideal because it involves a long and complicated preparation, for example, the package insert of GlucaGen® describes a 5-step procedure for injecting the recommended dose. Moreover, a study of the company LOCEMIA demonstrates that very few persons (approximately 10% of the participants) who were supposed to perform the reconstitution in emergency were capable of delivering the appropriate dose. Finally, the acidic pH of the solutions of human glucagon can generate pain upon injection in the patient.

Thus, there is a need for a ready-to-use human glucagon solution. Today, the solutions that are most advanced clinically speaking in order to enable the delivery of human glucagon circumvent the problem of stability of human glucagon in aqueous solution in different ways.

The company LOCEMIA has developed a lyophilized human glucagon spray which is currently being tested in phase 3 clinical study, and which is intended to be administered by the intranasal route. This spray is suitable for a so-called "rescue" use, that is to say in the case of a severe hypoglycemia, since it is ready to use and thus easy to use, in contrast to the solutions that need to be reconstituted. However, this product is not suitable for use in a pump or for a use that requires a precise control of the delivered quantity of human glucagon.

As for XERIS, it has developed a liquid formulation of human glucagon based on a polar aprotic solvent, such as DMSO, which is currently being tested in clinical studies. However, while the injection of a solution of organic solvents for "rescue" use can be considered, it is largely preferable to have an aqueous human glucagon solution for chronic use. Compositions comprising a combination with other peptides have been considered, notably amylin or a GLP-1 RA (glucagon-like peptide-1 receptor agonist).

Finally, in the face of the difficulties of formulation of human glucagon, analogs of human glucagon are in the process of being developed by large pharmaceutical companies such as NOVO NORDISK, SANOFI or ELI LILLY, in order to obtain formulations that have a stability compatible with pharmaceutical use. However, these peptides of which the primary sequence has been modified in comparison to the peptide of human origin can present a safety risk for the patients.

Thus, there is a major advantage in a solution that makes it possible to improve the solubilization and the stability, both chemical and physical, of human glucagon in an aqueous solution at a pH close to physiological pH, that is to say from 6.0 to 8.0. This could make it possible to obtain a pharmaceutical product that is easier to use by the patient in an emergency, but it could also open the field to new therapeutic applications of human glucagon, such as its use in a bi-hormonal artificial pancreas, for example.

The prior art proposes solutions in order to attempt to solve this problem.

Some documents propose using an alkaline pH. For example, US2015291680 teaches the solubilization of human glucagon at 1 mg/mL by using a pH from 8.8 to 9.4 and by using ferulic acid or tetrahydrocurcumin. However, apart from the fact that an alkaline pH is used, this solution presents the disadvantage of leading to a rather limited stability of the human glucagon over time. The article by Jackson et al. (Curr. Diab. Rep., 2012, 12, 705-710) proposes formulating human glucagon at an alkaline pH (approximately 10), in order to limit the formation of fibrils.

However, this solution does not prevent a rapid chemical degradation of human glucagon.

The application WO2014096440 (NOVOZYME), on the other hand, considers using a slightly acidic pH (approximately 5.5) in the presence of albumin and polysorbate, in order to improve the stability by reducing the rate of fibril formation. However, this solution presents a limited improvement of the stability. Most of the solutions described in the prior art making it possible to obtain a clear solution of human glucagon and to prevent aggregation, gelling or precipitation of the human glucagon involve the use of surfactants, detergents or other known solubilizing agents.

For example, Matilainen et al. (J. Pharm. Sci., 2008, 97, 2720-2729 and Eur. J. Pharm. Sci., 2009, 36, 412-420) described the use of cyclodextrin in order to limit the rate of formation of fibrils of human glucagon. However, the improvement provided does not appear to be sufficient for considering use in a pump.

The solutions proposed comprise hydrophilic surfactants:
GB1202607 (NOVO NORDISK) describes the use of anionic or cationic detergents.
U.S. Pat. No. 6,384,016 (NOVO NORDISK) and US2011097386 (BIODEL) use lysophospholipids (or lysolecithins).
WO2015095389 (AEGIS) describes non-ionic surfactants such as dodecyl maltoside for improving the bioavailability of therapeutic agents, in the case of delivery by application on the mucous membranes or the epidermis, and, in particular, in the case of ocular, nasal, oral or nasolacrimal delivery. This document describes that the presence of alkyl glycosides leads to an improvement of the absorption of human glucagon at the ocular site,
the application WO2012059764 (ARECOR) describes cationic surfactants and, more precisely, aromatic ammonium chlorides.

The surfactants indicated in the above documents can be too toxic or irritating for chronic use by the subcutaneous route. For example, the lysophospholipids (or lysolecithins) are known to lyse the red blood cells due to their hemolytic properties. In a subcutaneous injection, this can cause local damage to the tissues and pains at the injection site. In the case of continuous injection by means of a pump, this can lead to pains and/or irritation at the site of insertion of the needle. The international application WO2011138802 (Sun Pharma) describes a ready-to-use solution of human glucagon in a micellar aqueous solution at a pH from 5 to 7.5 in the presence of a pegylated lipid (pegylated distearoylphosphatidylethanolamine). However, Garay et al. (Expert Opin Drug Deliv (2012) 9, 1319-1323) teach that polyethylene glycol is both immunogenic and antigenic. This may be prejudicial to patients with anti-PEG antibodies. Moreover, Ganson et al. (J. Allergy Clin. Immunol. (2015) doi: 10.1016/j.jaci.2015.10.034) describe that a clinical study pertaining to pegnivacogin coupled to 40 kDa methoxypolyethylene glycol (mPEG) led to inflammatory responses starting with the first dose of pegnivacogin in 3 of the 640 patients. Among these three patients, two met the anaphylaxis criteria, and one had an isolated dermal reaction; each event was considered serious, and one was even considered life threatening to the patient. These adverse events resulted in the stopping of the clinical trial and raise the problem of the adverse effects of pegylated compounds.

The document WO2013101749 (LATITUDE) describes nanoemulsions of human glucagon. However, relatively moderate performances are claimed in terms of chemical stability, that is to say that the composition comprises at least 75% of the initial concentration after 3-7 days at 37° C.

In addition, it should be noted that, to this date, to the knowledge of the applicant, no pharmaceutical formulation comprising human glucagon in the form of an aqueous solution is being tested in a clinical study.

Thus, a need remains for a liquid aqueous formulation at a pH close to physiological pH, from 6.0 to 8.0, which enables solubilization and the obtention of a satisfactory stability of human glucagon, both in terms of physical stability and chemical stability. More particularly, there is need for such a formulation that can be used in a bi-hormonal pump (insulin/human glucagon).

This need is particularly clear in view of the fact that Tan et al. (Diabetes, 2013, 62, 1131-138) shows that combining human glucagon with a GLP-1 RA is an attractive proposition for treating obesity and diabetes. Now, being able to formulate human glucagon in a stable manner in an aqueous solution at a pH close to physiological pH from 6.0 to 8.0 makes it possible to be under conditions more favorable for being able to improve the stability of the GLP-1 RA which are sensitive to acidic or alkaline conditions.

The co-polyamino acids bearing carboxylate charges and hydrophobic radicals Hy according to the invention present an excellent resistance to hydrolysis. This can be shown particularly under accelerated conditions, for example, in hydrolysis tests at alkaline pH (pH 12).

In addition, forced oxidation tests, for example, of the Fenton oxidation type, show that the co-polyamino acids bearing carboxylate charges and hydrophobic radicals Hy present a good resistance to oxidation.

The invention thus relates to physically stable compositions in the form of an injectable aqueous solution, the pH of which is from 6.0 to 8.0, comprising at least:
a) human glucagon, and
b) a co-polyamino acid bearing carboxylate charges and hydrophobic radicals Hy, said co-polyamino acid consisting of glutamic or aspartic units, and said hydrophobic radicals Hy being radicals of the following formula I:

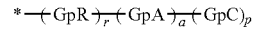

Formula I in which
GpR is a radical of formula II:

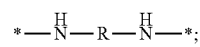

II

GpA is a radical of formula III or III':

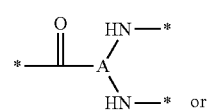

III or

III'

GpC is a radical of formula IV:

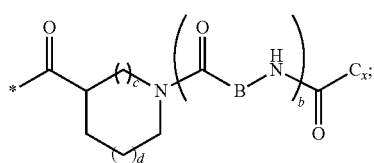

the * indicate the sites of attachment of the different groups;
a is a whole number equal to 0 or 1;
b is a whole number equal to 0 or 1;
p is a whole number equal to 1 or 2, and
  if p is equal to 1, then a is equal to 0 or 1 and GpA is a radical of formula III', and
  if p is equal to 2, then a is equal to 1 and GpA is a radical of formula III;
c is a whole number equal to 0 or 1, and, if c is equal to 0, then d is equal to 1 or 2;
d is a whole number equal to 0, to 1 or 2;
r is a whole number equal to 0 or 1, and
  if r is equal to 0, then the hydrophobic radical of formula I is bound to the co-polyamino acid via a covalent bond between a carbonyl of the hydrophobic radical and a nitrogen atom in N-terminal position of the co-polyamino acid therefore forming an amide function originating from the reaction of an amine function in N-terminal position of the precursor of the co-polyamino acid and an acid function borne by the precursor of the hydrophobic radical, and
  if r is equal to 1, then the hydrophobic radical of formula I is bound to the co-polyamino acid:
    via a covalent bond between a nitrogen atom of the hydrophobic radical and a carbonyl of the co-polyamino acid therefore forming an amide function originating from the reaction between an amine function of the precursor of the hydrophobic radical and an acid function borne by the precursor of the co-polyamino acid, or
    via a covalent bond between a carbonyl of the hydrophobic radical and a nitrogen atom in N-terminal position of the co-polyamino acid therefore forming an amide function originating from the reaction of an acid function of the precursor of the hydrophobic radical and an amine function in N terminal position borne by the precursor of the co-polyamino acid;
R is a radical selected from the group consisting of:
  a linear or branched divalent alkyl radical comprising, if GpR is a radical of formula II, from 2 to 12 carbon atoms;
  a linear or branched divalent alkyl radical comprising, if GpR is a radical of formula II, from 2 to 11 carbon atoms, said alkyl radical bearing one or more —CONH2 functions, and
  an unsubstituted ether or polyether radical comprising from 4 to 14 carbon atoms and from 1 to 5 oxygen atoms;
A is a linear or branched alkyl radical comprising from 1 to 6 carbon atoms;
B is a linear or branched alkyl radical, optionally comprising an aromatic ring, comprising from 1 to 9 carbon atoms;

$C_x$ is a linear or branched monovalent alkyl radical, in which x indicates the number of carbon atoms, and:
  if p is equal to 1, x is from 11 to 25 ($11 \leq x \leq 25$);
  if p is equal to 2, x is from 9 to 15 ($9 \leq x \leq 15$),
the ratio i between the number of hydrophobic radicals and the number of glutamic or aspartic units being between $0 < i \leq 0.5$;
when several hydrophobic radicals are borne by a co-polyamino acid, then they are identical or different,
the degree of polymerization DP in glutamic or aspartic units is from 5 to 250;
the free acid functions being in the form of a salt of an alkaline cation selected from the group consisting of $Na^+$ and $K^+$.

In an embodiment, the composition is characterized in that the pH is from 6.6 to 7.8.

In an embodiment, the composition is characterized in that the pH is from 7.0 to 7.8.

In an embodiment, the composition is characterized in that the pH is from 6.8 to 7.4.

In an embodiment, the composition is characterized in that said hydrophobic radicals are selected from the hydrophobic radicals of formula I in which p is equal to 1, and, if x is less than or equal to 14 ($x \leq 14$), then r=0 or r=1.

In an embodiment, the composition is characterized in that said hydrophobic radicals are selected from the hydrophobic radicals of formula I in which p is equal to 1, and, if x is from 15 to 16 ($15 \leq x \leq 16$), then r=1.

In an embodiment, the composition is characterized in that said hydrophobic radicals are selected from the hydrophobic radicals of formula I in which p is equal to 1, and, if x is greater than 17 ($17 \leq x$), then r=1 and R is an ether or polyether radical.

In an embodiment, the composition is characterized in that said hydrophobic radicals are selected from the hydrophobic-radicals of formula I in which, if p is equal to 1, then x is from 17 to 25 ($17 \leq x \leq 25$).

In an embodiment, the composition is characterized in that said hydrophobic radicals are selected from the hydrophobic radicals of formula I in which p=1, represented by the following formula V:

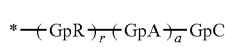

formula V

GpR, GpA, GpC, r and a have the definitions given above.

In an embodiment, the composition is characterized in that the hydrophobic radical is a radical of formula V, in which r is equal to 1 (r=1), and a is equal to 0 (a=0).

In an embodiment, the composition is characterized in that the hydrophobic radical is a radical of formula V in which r is equal to 1 (r=1) and a is equal to 1 (a=1).

In an embodiment, the composition is characterized in that the hydrophobic radical is a radical of formula V in which GpR is a radical of formula II.

In an embodiment, the composition is characterized in that the hydrophobic radical is a radical of formula V in which GpR is a radical of formula II, in which R is a divalent linear alkyl radical comprising from 2 to 12 carbon atoms.

In an embodiment, the composition is characterized in that the hydrophobic radical is a radical of formula V in which GpR is a radical of formula II in which R is a divalent alkyl radical comprising from 2 to 6 carbon atoms.

In an embodiment, the composition is characterized in that the hydrophobic radical is a radical of formula V in which GpR is a radical of formula II in which R is a divalent linear alkyl radical comprising from 2 to 6 carbon atoms.

In an embodiment, the composition is characterized in that the hydrophobic radical is a radical of formula V in which GpR is a radical of formula II in which R is a divalent alkyl radical comprising from 2 to 4 carbon atoms.

In an embodiment, the composition is characterized in that the hydrophobic radical is a radical of formula V in which GpR is a radical of formula II in which R is a divalent linear alkyl radical comprising from 2 to 4 carbon atoms.

In an embodiment, the composition is characterized in that the hydrophobic radical is a radical of formula V in which GpR is a radical of formula II in which R is a divalent alkyl radical comprising 2 carbon atoms.

In an embodiment, the composition is characterized in that the hydrophobic radical is a radical of formula V in which GpR is a radical of formula II'.

In an embodiment, the composition is characterized in that the hydrophobic radical is a radical of formula V in which GpR is a radical of formula II in which R is a divalent alkyl radical comprising from 2 to 5 carbon atoms and bearing one or more amide functions (—$CONH_2$).

In an embodiment, the composition is characterized in that the hydrophobic radical is a radical of formula V in which GpR is a radical of formula II, in which R is a divalent linear alkyl radical comprising from 2 to 5 carbon atoms and bearing one or more amide functions (—$CONH_2$).

In an embodiment, the composition is characterized in that the hydrophobic radical is a radical of formula V in which GpR is a radical of formula II in which R is a radical selected from the group consisting of the radicals represented by the formulas below:

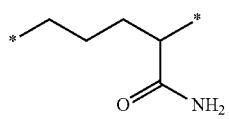

Formula X1

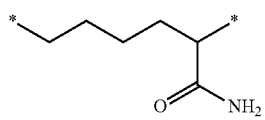

Formula X2

In an embodiment, the composition is characterized in that the radical R is bound to the co-polyamino acid via an amide function borne by the carbon in delta or epsilon position (or in position 4 or 5) with respect to the amide function (—$CONH_2$).

In an embodiment, the composition is characterized in that the hydrophobic radical is a radical of formula V in which GpR is a radical of formula II or II', in which R is an unsubstituted linear ether or polyether radical comprising from 4 to 14 carbon atoms and from 1 to 5 oxygen atoms.

In an embodiment, the composition is characterized in that the hydrophobic radical is a radical of formula V in which GpR is a radical of formula II or II', in which R is an ether radical.

In an embodiment, the composition is characterized in that the hydrophobic radical is a radical of formula V in which GpR is a radical of formula II or II', in which R is an ether radical comprising from 4 to 6 carbon atoms.

In an embodiment, the composition is characterized in that the hydrophobic radical is a radical of formula V in which GpR is a radical of formula II, in which R is an ether radical represented by the formula

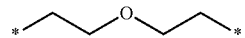

of formula X7.

In an embodiment, the composition is characterized in that the hydrophobic radical is a radical of formula V in which GpR is a radical of formula II or II', in which R is a polyether radical.

In an embodiment, the composition is characterized in that the hydrophobic radical is a radical of formula V in which GpR is a radical of formula II or II', in which R is a linear polyether radical comprising from 6 to 10 carbon atoms and from 2 to 3 oxygen atoms.

In an embodiment, the composition is characterized in that the hydrophobic radical of formula V in which GpR is a radical of formula II or II', in which R is a polyether radical selected from the group consisting of the radicals represented by the formulas below:

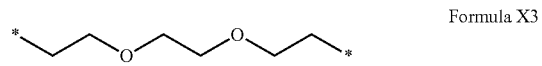

Formula X3

Formula X4

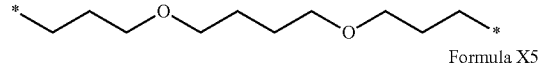

Formula X5

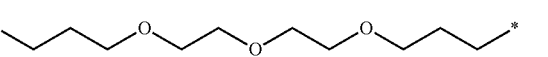

Formula X6

In an embodiment, the composition is characterized in that the hydrophobic radical of formula V in which GpR is a radical of formula II or IP, in which R is a radical of formula X3.

In an embodiment, the composition is characterized in that the hydrophobic radical of formula V in which GpR is a radical of formula II or II', in which R is a radical of formula X4.

In an embodiment, the composition is characterized in that the hydrophobic radical of formula V in which GpR is a radical of formula II or II', in which R is a radical of formula X5.

In an embodiment, the composition is characterized in that the hydrophobic radical of formula V in which GpR is a radical of formula II or II', in which R is a radical of formula X6.

In an embodiment, the composition is characterized in that the hydrophobic radical of formula V in which GpR is a radical of formula II in which R is a polyether radical selected from the group consisting of the radicals represented by the formulas below:

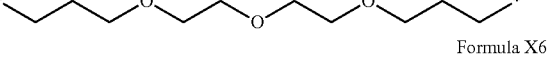

Formula X5

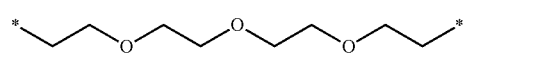

Formula X6

In an embodiment, the composition is characterized in that the hydrophobic radical of formula V in which GpR is a radical of formula II in which R is a polyether radical of formula X5.

In an embodiment, the composition is characterized in that the hydrophobic radical of formula V in which GpR is a radical of formula II in which R is a polyether radical of formula X6.

In an embodiment, the composition is characterized in that the hydrophobic radical is a radical of formula V in which a is equal to 0 (a=0) and r is equal to 0 (r=0).

In an embodiment, the composition is characterized in that the hydrophobic radical is a radical of formula V in which a is equal to 1 (a=1), and the radical GpA of formula III' is selected from the group consisting of the radicals represented by the formulas below;

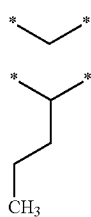

Formula Y1

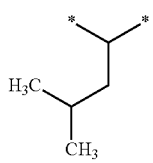

Formula Y2

Formula Y3

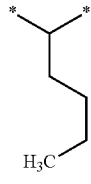

Formula Y4

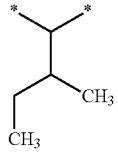

Formula Y5

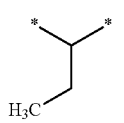

Formula Y6

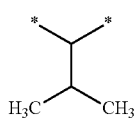

Formula Y7

Formula Y8

In an embodiment, the composition is characterized in that the hydrophobic radical is a radical of formula V in which a is equal to 1 (a=1), and the radical GpA of formula III' is a radical of formula Y1.

In an embodiment, the composition is characterized in that the hydrophobic radical is a radical of formula V in which a is equal to 1 (a=1), and the radical GpA of formula III' is a radical of formula Y2.

In an embodiment, the composition is characterized in that the hydrophobic radical is a radical of formula V in which a is equal to 1 (a=1) and the radical GpA of formula III' is a radical of formula Y3.

In an embodiment, the composition is characterized in that the hydrophobic radical is a radical of formula V in which a is equal to 1 (a=1) and the radical GpA of formula III' is a radical of formula Y4.

In an embodiment, the composition is characterized in that the hydrophobic radical is a radical of formula V in which a is equal to 1 (a=1) and the radical GpA of formula III' is a radical of formula Y5.

In an embodiment, the composition is characterized in that the hydrophobic radical is a radical of formula V in which a is equal to 1 (a=1) and the radical GpA of formula III' is a radical of formula Y6.

In an embodiment, the composition is characterized in that the hydrophobic radical is a radical of formula V in which a is equal to 1 (a=1) and the radical GpA of formula III' is a radical of formula Y7.

In an embodiment, the composition is characterized in that the hydrophobic radical is a radical of formula V in which a is equal to 1 (a=1) and the radical GpA of formula III' is a radical of formula Y8.

In an embodiment, the composition is characterized in that the hydrophobic radical is a radical of formula V in which the radical GpC of formula IV is selected from the group consisting of the radicals of formula IVa, IVb or IVc represented hereafter:

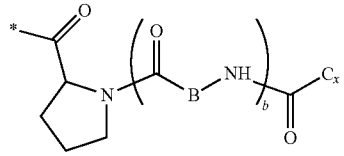

Formula IVa

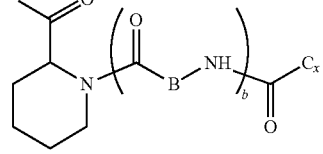

Formula IVb

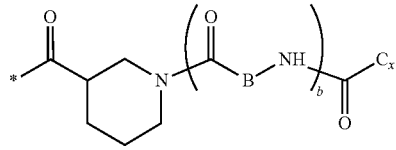

Formula IVc

In an embodiment, the composition is characterized in that the hydrophobic radical is a radical of formula V in which the radical GpC is of formula IVa.

In an embodiment, the composition is characterized in that the hydrophobic radical is a radical of formula V in which the radical GpC of formula IV is selected from the group consisting of the radicals of formula IVa, IVb or IVc in which b is equal to 0, respectively corresponding to formulas IVd, IVe and IVf, represented hereafter:

Formula IVd
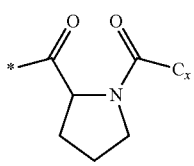

Formula IVe
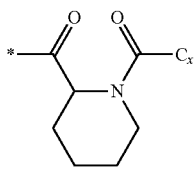

Formula IVf
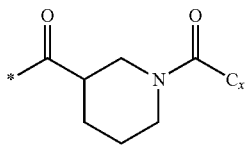

In an embodiment, the composition is characterized in that the hydrophobic radical is a radical of formula V in which the radical GpC corresponds to formula IV or IVa in which b=0, and corresponds to formula IVd.

In an embodiment, the composition is characterized in that the hydrophobic radical is a radical of formula V in which the radical GpC of formula IV in which b=1 is selected from the group consisting of the radicals in which B is an amino acid residue selected from the group consisting of the radicals represented by the formulas below:

Formula Y1

Formula Y2

Formula Y3
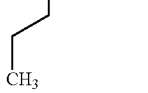

Formula Y4

Formula Y5

Formula Y6
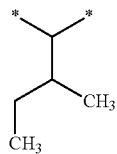

Formula Y7
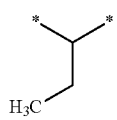

Formula Y8
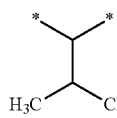

Formula Y9
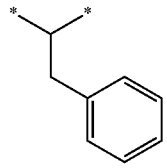

In an embodiment, the composition is characterized in that the hydrophobic radical is a radical of formula V in which the radical GpC of formula corresponds to formula IV or IVa in which b=1, is selected from the group consisting of the radicals in which B is an amino acid residue selected from the group consisting of the radicals represented by the formulas below:

Formula Y3
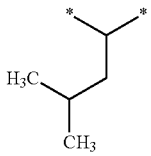

Formula Y9
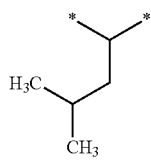

In an embodiment, the composition is characterized in that the hydrophobic radical is a radical of formula V in which the radical GpC of formula IV is selected from the group consisting of the radicals in which Cx is selected from the group consisting of the linear alkyl radicals.

In an embodiment, the composition is characterized in that the hydrophobic radical is a radical of formula V in which the radical GpC of formula IV is selected from the group consisting of radicals in which Cx is selected from the group consisting of the branched alkyl radicals.

In an embodiment, the composition is characterized in that the hydrophobic radical is a radical of formula V in which the radical GpC of formula IV is selected from the group consisting of alkyl radicals in which Cx is selected from the group consisting of the alkyl radicals comprising from 11 to 14 carbon atoms.

In an embodiment, the composition is characterized in that the hydrophobic radical is a radical of formula V in which the radical GpC of formula IV is selected from the group consisting of radicals in which Cx is selected from the group consisting of the radicals represented by the formulas below:

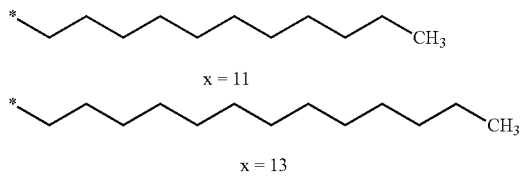

In an embodiment, the composition is characterized in that the hydrophobic radical is a radical of formula V in which the radical GpC of formula IV is selected from the group consisting of the radicals in which Cx is selected from the group consisting of the alkyl radicals comprising from 15 to 16 carbon atoms.

In an embodiment, the composition is characterized in that the hydrophobic radical is a radical of formula V in which the radical GpC of formula IV is selected from the group consisting of the radicals in which Cx is selected from the group consisting of the radicals represented by the formulas below;

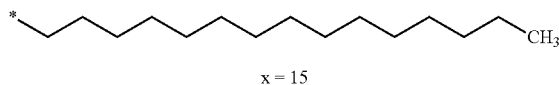

In an embodiment, the composition is characterized in that the hydrophobic radical is a radical of formula V in which the radical GpC of formula IV is selected from the group consisting of the radicals in which Cx is selected from the group consisting of the radicals represented by the formulas below:

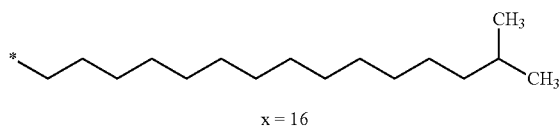

In an embodiment, the composition is characterized that the hydrophobic radical is a radical of formula V in which the radical GpC of formula IV is selected from the group consisting of the radicals in which Cx is selected from the group consisting of the alkyl radicals comprising from 17 to 25 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals comprising from 17 to 18 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals represented by the formulas below:

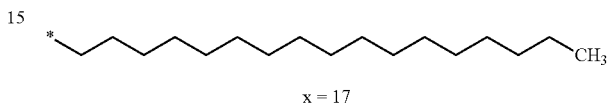

In an embodiment, the composition characterized in that the hydrophobic radical is a radical of formula V in which the radical GpC of formula IV is selected from the group consisting of the radicals in which Cx is selected from the group consisting of the alkyl radicals comprising from 18 to 25 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals represented by the formulas below:

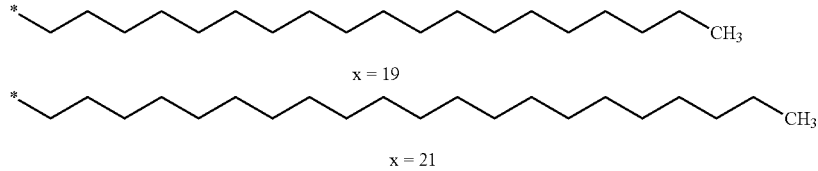

In an embodiment, the composition is characterized in that said hydrophobic radicals of formula I are selected from the hydrophobic radicals of formula I in which a=1 and p=2, represented by the following formula VI:

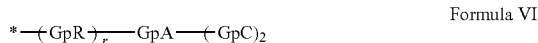

Formula VI in which
GpR, GpA, GpC, r and a have the definitions given above.

In an embodiment, the composition is characterized in that the hydrophobic radical is a radical of formula VI in which r=1.

In an embodiment, the composition is characterized in that the hydrophobic radical is a radical of formula VI in which GpR is a radical of formula II.

In an embodiment, the composition is characterized in that the hydrophobic radical is a radical of formula VI in which GpR is a radical of formula II in which R is a divalent linear alkyl radical comprising from 2 to 12 carbon atoms.

In an embodiment, the composition is characterized in that the hydrophobic radical is a radical of formula VI in which GpR is a radical of formula II in which R is a divalent alkyl radical comprising from 2 to 6 carbon atoms.

In an embodiment, the composition is characterized in that the hydrophobic radical is a radical of formula VI in which GpR is a radical of formula U in which R is a divalent linear alkyl radical comprising from 2 to 6 carbon atoms.

In an embodiment, the composition is characterized in that the hydrophobic radical is a radical of formula VI in which GpR is a radical of formula II in which R is an alkyl radical comprising from 2 to 4 carbon atoms.

In an embodiment, the composition is characterized in that the hydrophobic radical is a radical of formula VI in which GpR is a radical of formula II in which R is a divalent linear alkyl radical comprising from 2 to 4 carbon atoms.

In an embodiment, the composition is characterized in that the hydrophobic radical is a radical of formula VI in which GpR is a radical of formula II in which R is a divalent linear alkyl radical comprising 2 carbon atoms.

In an embodiment, the composition is characterized in that the hydrophobic radical is a radical of formula VI in which GpR is a radical of formula IF.

In an embodiment, the composition is characterized in that the hydrophobic radical is a radical of formula VI in which GpR is a radical of formula II, in which R is a divalent alkyl radical comprising from 2 to 5 carbon atoms and bearing one or more amide functions (—CONH2).

In an embodiment, the composition is characterized in that the hydrophobic radical is a radical of formula VI in which GpR is a radical of formula II, in which R is a divalent linear alkyl radical comprising from 2 to 5 carbon atoms and bearing one or more amide functions (—CONH2).

In an embodiment, the composition is characterized in that the hydrophobic radical is a radical of formula VI in which GpR is a radical of formula II, in which R is a radical selected from the group consisting of the radicals represented by the formulas below:

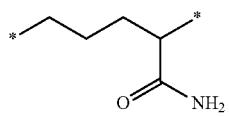

Formula X1

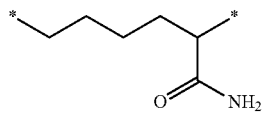

Formula X2

In an embodiment, the composition is characterized in that the hydrophobic radical is a radical of formula VI in which the amine function of the GpR radical involved in the formation of the amide function which binds said GpR radical to the co-polyamino acid is borne by a carbon in delta or epsilon position (or in position 4 or 5) with respect to the amide function (—CONH2).

In an embodiment, the composition is characterized in that the hydrophobic radical is a radical of formula VI in which GpR is a radical of formula II, in which R is an unsubstituted linear ether or polyether radical comprising from 4 to 14 carbon atoms and from 1 to 5 oxygen atoms.

In an embodiment, the composition is characterized in that the hydrophobic radical is a radical of formula VI in which GpR is a radical of formula II in which R is an ether radical.

In an embodiment, the composition is characterized in that the ether radical R is a radical comprising from 4 to 6 carbon atoms.

In an embodiment, the composition is characterized in that the ether radical is

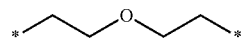 [SMILES: *CCOCC*]

of formula X7.

In an embodiment, the composition is characterized in that the hydrophobic radical is a radical of formula VI in which GpR is a radical of formula II, in which R is a polyether radical.

In an embodiment, the composition is characterized in that the hydrophobic radical is a radical of formula VI in which GpR is a radical of formula II, in which R is a linear polyether radical comprising from 6 to 10 carbon atoms and from 2 to 3 oxygen atoms.

In an embodiment, the composition is characterized in that the hydrophobic radical is a radical of formula VI in which GpR is a radical of formula II in which R is a linear polyether radical selected from the group consisting of the radicals represented by the formulas below:

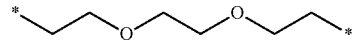

Formula X3

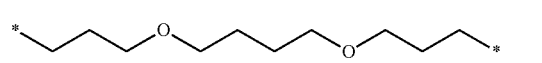

Formula X4

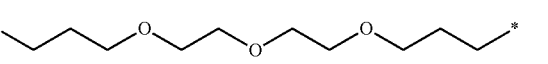

Formula X5

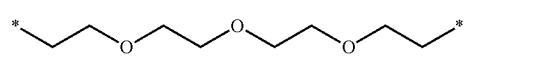

Formula X6

In an embodiment, the composition is characterized in that the hydrophobic radical is a radical of formula VI in which GpR is a radical of formula II in which R is a linear polyether radical of formula X4.

In an embodiment, the composition is characterized in that the hydrophobic radical is a radical of formula VI in which GpR is a radical of formula II in which R is a linear polyether radical of formula X5.

In an embodiment, the composition is characterized in that the hydrophobic radical is a radical of formula VI in which GpR is a radical of formula II in which R is a linear polyether radical of formula X6.

In an embodiment, the composition is characterized in that the hydrophobic radical is a radical of formula VI in which the radical GpA of formula III is selected from the group consisting of the radicals of formulas IIIa, IIIb and IIIc represented hereafter:

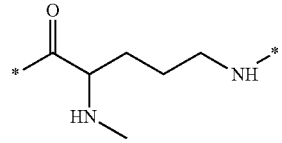

Formula IIIa

-continued

Formula IIIb

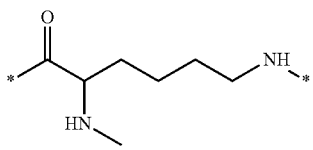

In an embodiment, the composition is characterized in that the hydrophobic radical is a radical of formula VI in which the radical GpA of formula II is a radical of formula IIIb represented hereafter:

Formula IIIb

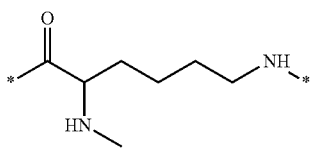

In an embodiment, the composition is characterized in that the hydrophobic radical is a radical of formula VI in which the radical GpA of formula III is a radical of formula IIIc.

In an embodiment, the composition is characterized in that the hydrophobic radical is a radical of formula VI in which the radical GpC of formula IV is selected from the group consisting of formulas IVa, IVb and IVc represented hereafter:

Formula IVa

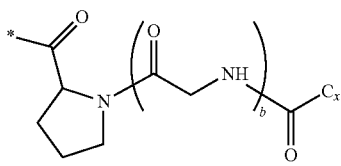

Formula IVb

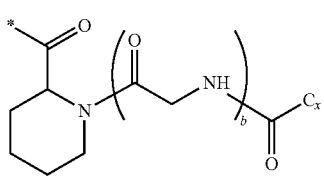

Formula IVc

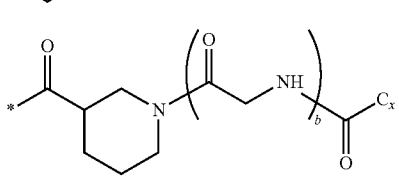

In an embodiment, the composition is characterized in that the hydrophobic radical is a radical of formula VI in which the radical GpC is of formula IVa.

In an embodiment, the composition is characterized in that the hydrophobic radical is a radical of formula VI in which the radical GpC of formula IV is selected from the group consisting of the radicals of formula IVa, IVb or IVc in which b is equal to 0, respectively corresponding to the formulas IVd, IVe and IVf, represented hereafter:

Formula IVd

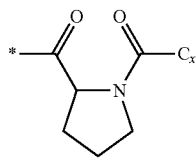

Formula IVe

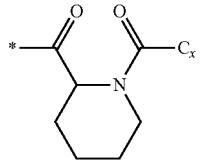

Formula IVf

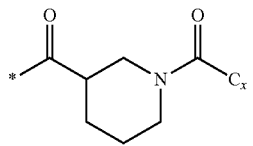

In an embodiment, the composition is characterized in that the hydrophobic radical is a radical of formula VI in which the radical GpC corresponds to formula IV or IVa in which b=0, and it corresponds to formula IVd.

In an embodiment, the composition is characterized in that the hydrophobic radical is a radical of formula VI in which the radical GpC of formula IV is selected from the group consisting of the radicals in which Cx is selected from the group consisting of the linear alkyl radicals comprising from 9 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the branched alkyl radicals comprising from 9 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising 9 or 10 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising from 11 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising from 11 to 13 carbon atoms.

In an embodiment, the composition is characterized in that the hydrophobic radical is a radical of formula VI in which the radical GpC of formula IV is selected from the group consisting of the radicals in which Cx is selected from the group consisting of the radicals represented by the formulas below:

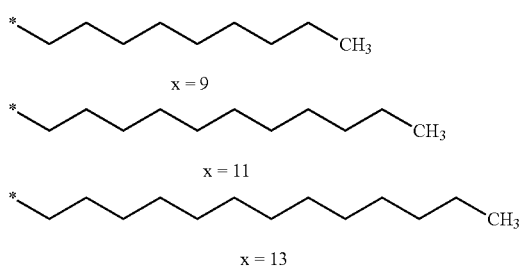

In an embodiment, the composition is characterized in that the hydrophobic radical is a radical of formula VI in which the radical GpC of formula IV is selected from the group consisting of the radicals in which Cx is selected from the group consisting of the alkyl radicals comprising 14 or 15 carbon atoms.

In an embodiment, the composition is characterized in that the hydrophobic radical is a radical of formula VI in which the radical GpC of formula IV is selected from the group consisting of the radicals in which Cx is selected from the group consisting of the radicals represented by the formulas below:

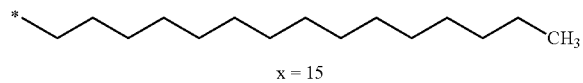

The co-polyamino acid bearing carboxylate charges and at least one hydrophobic radical of formula I can also be referred to as "co-polyamino acid" in the present description.

In an embodiment, the composition is characterized in that the co-polyamino acid bearing carboxylate charges and hydrophobic radicals is selected from the co-polyamino acids of the following formula VIIa:

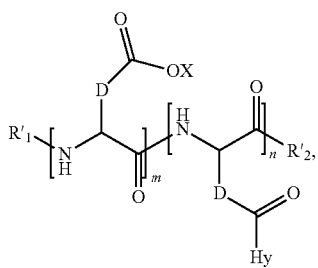

Formula VIIa in which,
D represents, independently, either a —CH$_2$— group (aspartic unit) or a —CH$_2$—CH$_2$— group (glutamic unit),
Hy is a hydrophobic radical selected from the hydrophobic radicals of formula I, V or VI, in which r=1 and GpR is a radical of Formula II,
X represents H or a cationic entity selected from the group comprising the metal cations;
n+m represents the degree of polymerization DP of the co-polyamino acid, that is to say the average number of monomer units per co-polyamino acid chain and $5 \leq n+m \leq 250$;

R'1 is a radical selected from the group consisting of H, a C2 to C10 linear acyl group, a C4 to C10 branched acyl group, benzyl, a terminal "amino acid" unit and a pyroglutamate, R'2 is a —NR'R" radical, R' and R", which are identical or different, being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms selected from the group consisting of O, N and S.

In an embodiment, the composition according to the invention is characterized in that the co-polyamino acid bearing carboxylate charges and hydrophobic radicals is selected from the co-polyamino acids of formula VIIa in which Hy is a radical of formula V or of formula VI, with r=1.

In an embodiment, the composition according to the invention is characterized in that the co-polyamino acid bearing carboxylate charges and hydrophobic radicals is selected from the co-polyamino acids of formula VIIa in which Hy is a radical of formula V or of formula VI, with GpR of formula II.

In an embodiment, the composition according to the invention is characterized in that the co-polyamino acid bearing carboxylate charges and hydrophobic radicals is selected from the co-polyamino acids of formula VIIa in which Hy is a radical of formula V.

In an embodiment, the composition according to the invention is characterized in that the co-polyamino acid bearing carboxylate charges and hydrophobic radicals is selected from the co-polyamino acids of formula VIIa in which Hy is of formula V and GpC is a radical of formula IVd.

In an embodiment, the composition according to the invention is characterized in that the co-polyamino acid bearing carboxylate charges and hydrophobic radicals is selected from the co-polyamino acids of formula VIIa in which Hy is of formula V and GpC is a radical of formula IVd in which x=13.

In an embodiment, the composition according to the invention is characterized in that the co-polyamino acid bearing carboxylate charges and hydrophobic radicals is selected from the co-polyamino acids of formula VIIa in which Hy is of formula V and GpC is a radical of formula IVd in which x=15.

In an embodiment, the composition according to the invention is characterized in that the co-polyamino acid bearing carboxylate charges and hydrophobic radicals is selected from the co-polyamino acids of formula VIIa in which Hy is of formula V and GpC is a radical of formula IVd in which x=17.

In an embodiment, the composition according to the invention is characterized in that the co-polyamino acid bearing carboxylate charges and hydrophobic radicals is selected from the co-polyamino acids of formula VIIa in which Hy is of formula V and GpC is a radical of formula IVd in which x=19.

In an embodiment, the composition according to the invention is characterized in that the co-polyamino acid bearing carboxylate charges and hydrophobic radicals is selected from the co-polyamino acids of formula VIIa in which Hy is a radical of formula VI.

In an embodiment, the composition according to the invention is characterized in that the co-polyamino acid bearing carboxylate charges and hydrophobic radicals is selected from the co-polyamino acids of formula VIIa in which Hy is a radical of formula VI in which r=1 and GpR is of formula I.

In an embodiment, the composition according to the invention is characterized in that the co-polyamino acid bearing carboxylate charges and hydrophobic radicals is selected from the co-polyamino acids of formula VIIa in which Hy is a radical of formula VI in which r=1 and GpR is of formula II and for GpC, b=0.

In an embodiment, the composition according to the invention is characterized in that the co-polyamino acid bearing carboxylate charges and hydrophobic radicals is selected from the co-polyamino acids of formula VIIa in which Hy is of formula VI, GpR of formula II and GpC is a radical of formula IVd.

In an embodiment, the composition according to the invention is characterized in that the co-polyamino acid bearing carboxylate charges and hydrophobic radicals is selected from the co-polyamino acids of formula VIIa in which Hy is of formula VI, GpR of formula II and GpC is a radical of formula IVd and r=1.

In an embodiment, the composition according to the invention is characterized in that the co-polyamino acid bearing carboxylate charges and hydrophobic radicals is selected from the co-polyamino acids of formula VIIa in which Hy is of formula VI, GpR of formula II and GpC is a radical of formula IVd in which x is from 11 to 15.

In an embodiment, the composition according to the invention is characterized in that, when the co-polyamino acid comprises aspartate units, then the co-polyamino acid can, in addition, comprise monomer units of formula VIII and/or VIII':

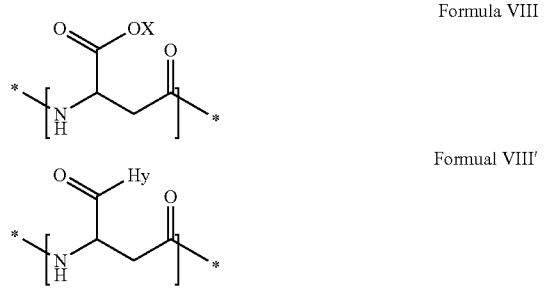

Formula VIII

Formual VIII'

In an embodiment, the composition is characterized in that $R_1$ is a radical selected from the group consisting of a $C_2$ to $C_{10}$ linear acyl group, a $C_4$ to $C_{10}$ branched acyl group, benzyl, a terminal "amino acid" unit and a pyroglutamate.

In an embodiment, the composition is characterized in that $R_1$ is a radical selected from the group consisting of a $C_2$ to $C_{10}$ linear acyl group or a $C_4$ to $C_{10}$ branched acyl group.

In an embodiment, the composition is characterized in that the co-polyamino acid bearing carboxylate charges and hydrophobic radicals is selected from the co-polyamino acids of formula VIIa in which the group D is a group —$CH_2$— (aspartic unit).

In an embodiment, the composition is characterized in that the co-polyamino acid bearing carboxylate charges and hydrophobic radicals is selected from the co-polyamino acids of formula VIIa in which the group D is a —$CH_2$—$CH_2$— group (glutamic unit).

In an embodiment, the composition is characterized in that the ratio i between the number of hydrophobic radicals and the number of glutamic or aspartic units is from 0.007 to 0.3.

In an embodiment, the composition is characterized in that the ratio i between the number of hydrophobic radicals and the number of glutamic of glutamic or aspartic units is from 0.01 to 0.3.

In an embodiment, the composition is characterized in that the ratio i between the number of hydrophobic radicals and the number of glutamic or aspartic units is from 0.02 to 0.2.

In an embodiment, the composition is characterized in that the hydrophobic radical corresponds to formula VI and the ratio i between the number of hydrophobic radicals and the number of glutamic or aspartic units is from 0.007 to 0.15.

In an embodiment, the composition is characterized in that the hydrophobic radical corresponds to formula VI and the ratio i between the number of hydrophobic radicals and the number of glutamic or aspartic units is from 0.01 to 0.1.

In an embodiment, the composition is characterized in that the hydrophobic radical corresponds to formula VI and the ratio i between the number of hydrophobic radicals and the number of glutamic or aspartic units is from 0.02 to 0.08.

In an embodiment, the composition is characterized in that the hydrophobic radical corresponds to formula VI in which the radical Cx comprises from 9 to 10 carbon atoms and the ratio i between the number of hydrophobic radicals and the number of glutamic or aspartic units is from 0.03 to 0.15.

In an embodiment, the composition is characterized in that the hydrophobic radical corresponds to formula VI in which the radical Cx comprises from 11 to 12 carbon atoms and the ratio i between the number of hydrophobic radicals and the number of glutamic or aspartic units is from 0.015 to 0.1.

In an embodiment, the composition is characterized in that the hydrophobic radical corresponds to formula VI in which the radical Cx comprises from 11 to 12 carbon atoms and the ratio i between the number of hydrophobic radicals and the number of glutamic or aspartic units is from 0.02 to 0.08.

In an embodiment, the composition is characterized in that the hydrophobic radical corresponds to formula VI in which the radical Cx comprises from 13 to 15 carbon atoms and the ratio i between the number of hydrophobic radicals and the number of glutamic or aspartic units is from 0.01 to 0.1.

In an embodiment, the composition is characterized in that the hydrophobic radical corresponds to formula VI in which the radical Cx comprises from 13 to 15 carbon atoms, and the ratio i between the number of hydrophobic radicals and the number of glutamic or aspartic units is from 0.01 to 0.06.

In an embodiment, the composition is characterized in that the hydrophobic radical corresponds to formula V, and the ratio i between the number of hydrophobic radicals and the number of glutamic or aspartic units is from 0.007 to 0.3.

In an embodiment, the composition is characterized in that the hydrophobic radical corresponds to formula V, and the ratio i between the number of hydrophobic radicals and the number of glutamic or aspartic units is from 0.01 to 0.3.

In an embodiment, the composition is characterized in that the hydrophobic radical corresponds to formula V, and the ratio i between the number of hydrophobic radicals and the number of glutamic or aspartic units is from 0.015 to 0.2.

In an embodiment, the composition is characterized in that the hydrophobic radical corresponds to formula V in which the radical Cx comprises from 11 to 14 carbon atoms, and the ratio i between the number of hydrophobic radicals and the number of glutamic or aspartic units is from 0.1 to 0.2.

In an embodiment, the composition is characterized in that the hydrophobic radical corresponds to formula V in which the radical Cx comprises from 15 to 16 carbon atoms, and the ratio i between the number of hydrophobic radicals and the number of glutamic or aspartic units is from 0.04 to 0.15.

In an embodiment, the composition is characterized in that the hydrophobic radical corresponds to formula V in which the radical Cx comprises from 17 to 18 carbon atoms, and the ratio i between the number of hydrophobic radicals and the number of glutamic or aspartic units is from 0.02 to 0.06.

In an embodiment, the composition is characterized in that the hydrophobic radical corresponds to formula V in which the radical Cx comprises from 19 to 25 carbon atoms, and the ratio i between the number of hydrophobic radicals and the number of glutamic or aspartic units is from 0.01 to 0.06.

In an embodiment, the composition is characterized in that the hydrophobic radical corresponds to formula V in which the radical Cx comprises from 19 to 25 carbon atoms, and the ratio i between the number of hydrophobic radicals and the number of glutamic or aspartic units is from 0.01 to 0.05.

In an embodiment, the composition according to the invention is characterized in that n+m is from 10 to 250.

In an embodiment, the composition according to the invention is characterized in that n+m is from 10 to 200.

In an embodiment, the composition according to the invention is characterized in that n+m is from 15 to 150.

In an embodiment, the composition according to the invention is characterized in that n+m is from 15 to 100.

In an embodiment, the composition according to the invention is characterized in that n+m is from 15 to 80.

In an embodiment, the composition according to the invention is characterized in that n+m is from 15 to 65.

In an embodiment, the composition according to the invention is characterized in that n+m is from 20 to 60.

In an embodiment, the composition according to the invention is characterized in that n+m is from 20 to 50.

In an embodiment, the composition according to the invention is characterized in that n+m is from 20 to 40.

The invention also relates to said co-polyamino acid bearing carboxylate charges and hydrophobic radicals of formula I and the precursors of said hydrophobic radicals.

The co-polyamino acid bearing carboxylate charges and hydrophobic radicals of formula I are soluble in distilled water at a pH from 6 to 8, at a temperature of 25° C., and at a concentration of less than 100 mg/mL.

The invention moreover relates to a method for preparing stable injectable compositions.

"Soluble" is understood to mean capable of enabling the preparation of a clear, particle-free solution at a concentration of less than 100 mg/mL in distilled water at 25° C.

"Solution" is understood to mean a liquid composition free of visible particles, using the procedure according to the pharmacopoeias EP 8.0, under point 2.9.20, and US <790>.

"Physically stable composition" is understood to mean compositions which, after a certain storage time at a certain temperature meet the criteria of visual inspection described in the European, American and international pharmacopoeias, that is to say compositions which are clear and contain no visible particles, and are also colorless.

"Chemically stable composition" is understood to mean compositions which after a certain storage time at a certain temperature, present a minimum recovery of the active ingredients and are in compliance with the specifications applicable to the pharmaceutical products.

A conventional method for measuring the stabilities of the proteins or peptides consists in measuring the formation of fibrils with the aid of Thioflavin T, also referred to as ThT. This method makes it possible, under temperature and stirring conditions that enable an acceleration of the phenomenon, to measure the lag time before the formation of fibrils by measuring the increase in fluorescence. The compositions according to the invention have a lag time before the formation of fibrils which is clearly greater than the lag time of the glucagon at the pH of interest.

"Injectable aqueous solution" is understood to mean water-based solutions which meet the conditions of the EP and US pharmacopoeias, and which are sufficiently liquid to be injected.

"Co-polyamino acid consisting of glutamic or aspartic units" is understood to mean noncyclic linear chains of glutamic acid or aspartic acid units bound together by peptide bonds, said chains having a C-terminal part corresponding to the carboxylic acid of one end and an N-terminal part corresponding to the amine of the other end of the chain.

"Alkyl radical" is understood to mean a linear or branched carbon chain which comprises no heteroatom.

The co-polyamino acid is a statistical or block co-polyamino acid.

The co-polyamino acid is a statistical co-polyamino acid in the chain of the glutamic and/or aspartic units.

In the formulas, the * indicate the sites of attachment of the different elements represented.

In formulas I, V and VI, the * indicate the sites of attachment of the hydrophobic radicals to the co-polyamino acid. The radicals Hy are attached to the polyamino acid via amide functions.

In formulas II and II', the * indicate, from left to right, respectively, the sites of attachment of GpR:
 to the co-polyamino acid and
 to the GpA if a=1, or to GPC if a=0.

In formulas III and III', the * indicate, from left to right, respectively, the sites of attachment of GpA:
 to GpR if r=1, or to the co-polyamino acid if r=0, and
 to GpC.

In formula IV, the * indicates the site of attachment of GpC:
 to GpA if a=1, GpR if r=1 and a=0, or to the co-polyamino acid if r=0 and a=0.

All the attachments between the different groups GpR, GpA and GpC are amide functions.

The radicals Hy, GpR, GpA, GpC, and D are each independently identical or different from one monomer unit to the next.

When the co-polyamino acid comprises one or more aspartic unit(s), it (they) can undergo structural rearrangements.

In an embodiment, the composition according to the invention is characterized in that the co-polyamino acids obtained moreover comprise monomer units of formula VIII and/or VIII':

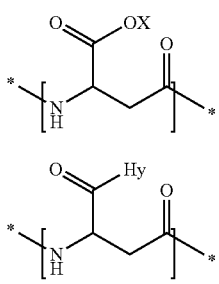

In an embodiment, the at least one hydrophobic radical of formula I is selected from the radicals of formula I in which, r=1, a=0, p=1, GpR corresponds to formula II in which R is —CH$_2$—CH$_2$—, GpC corresponds to formula IVd in which x=15 and Cx is

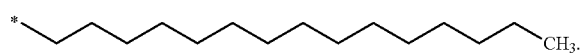

In an embodiment, the at least one hydrophobic radical of formula I is selected from the radicals of formula I in which, r=1, a=0, p=1, GpR corresponds to formula II in which R is —CH$_2$—CH$_2$—, GpC corresponds to formula IVd in which x=16 and Cx is

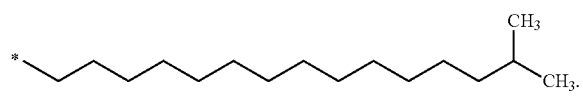

In an embodiment, the at least one hydrophobic radical of formula I is selected from the radicals of formula I in which r=1, a=0, p=1, GpR corresponds to formula II in which R is

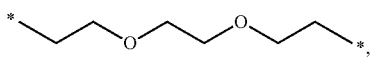

GpC corresponds to formula IVd in which x=15 and Cx is

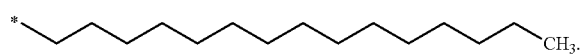 [SMILES: CCCCCCCCCCCCCCCC]

In an embodiment, the at least one hydrophobic radical of formula I is selected from the radicals of formula I in which r=1, a=0, p=1, GpR corresponds to formula II in which R is

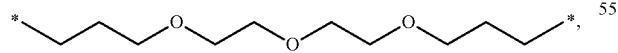

GpC corresponds to formula IVd in which x=15 and Cx is

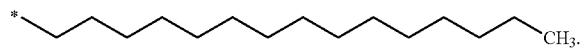

In an embodiment, the at least one hydrophobic radical of formula I is selected from the radicals of formula 1 in which r=1, a=0, p=1, GpR corresponds to formula II in which R is

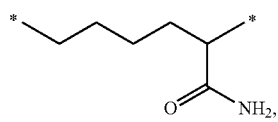

GpC corresponds to formula IVd in which x=15 and Cx is

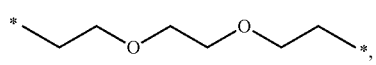

In an embodiment, the at least one hydrophobic radical of formula I is selected from the radicals of formula I in which r=1, a=0, p=1, GpR corresponds to formula II in which R is

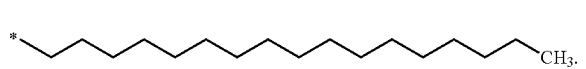

GpC corresponds to formula IVd in which x=17 and Cx is

In an embodiment, the at least one hydrophobic radical of formula I is selected from the radicals of formula I in which r=1, a=0, p=1, GpR corresponds to formula II in which R is

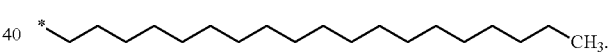

GpC corresponds to formula IVd in which x=19 and Cx is

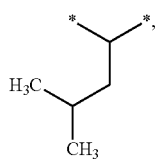

In an embodiment, the at least one hydrophobic radical of formula I is selected from the radicals of formula I in which r=1, a=0, p=1, GpR corresponds to formula II in which R is —CH$_2$—CH$_2$—, GpC corresponds to formula IVa in which b=1, B is

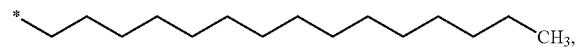

x=15 and Cx is

In an embodiment, the at least one hydrophobic radical of formula I is selected from the radicals of formula I in which r=1, a=0, p=1, GpR corresponds to formula II in which R is —CH$_2$—CH$_2$—, GpC corresponds to formula IVa in which b=1, B is

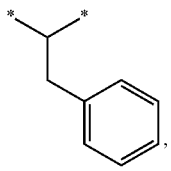

x=11 and Cx

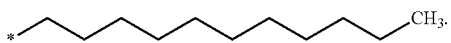 [SMILES: *CCCCCCCCCCC]

In an embodiment, the at least one hydrophobic radical of formula I is selected from the radicals of formula 1 in which r=1, a=1, p=2, GpR corresponds to formula II in which R is —CH$_2$—CH$_2$—, GpA corresponds to formula IIIb, GpC corresponds to formula IVd in which x=9 and Cx is

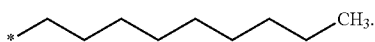

In an embodiment, the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

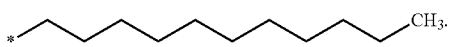

In an embodiment, the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=13 and Cx is

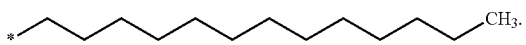

In an embodiment, the at least one hydrophobic radical of formula I is selected from the radicals of formula I in which r=1, a=1, p=2, GpR corresponds to formula II in which R is

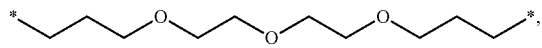

GpA corresponds to formula IIIb, GpC corresponds to formula IVd in which x=13 and Cx is

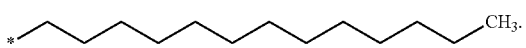 [SMILES: *CCCCCCCCCCCCC]

In an embodiment, the co-polyamino acid bearing carboxylate charges and hydrophobic radicals is a co-polyamino acid of formula VII or VIIa in which DP=23+/−5, i=0.05+/−0.02 and the at least one hydrophobic radical of formula I is selected from the radicals of formula I in which r=1, a=0, p=1, GpR corresponds to formula II in which R is —CH$_2$—CH$_2$—, GpC corresponds to formula IVd in which x=15 and Cx is

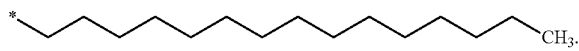

The values of the degree of polymerization DP and of ratio i are estimated by $^1$H NMR in D$_2$O by comparing the integration of the signals originating from the hydrophobic groups with the integration of the signals originating from the main chain of the co-polyamino acid.

In an embodiment, the co-polyamino acid bearing carboxylate charges and hydrophobic radicals is a co-polyamino acid of formula VII or VIIa in which DP=35+/−5, i=0.05+/−0.02 and the at least one hydrophobic radical of formula is selected from the radicals of formula I in which r=1, a=0, p=1, GpR corresponds to formula II in which R equals —CH$_2$—CH$_2$—, GpC corresponds to formula IVd in which x=15 and Cx is

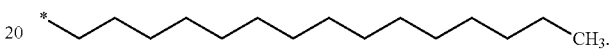

In an embodiment, the co-polyamino acid bearing carboxylate charges and hydrophobic radicals is a co-polyamino acid of formula VII or VIIa in which DP=35+/−5, i=0.10+/−0.02 and the at least one hydrophobic radical of formula I is selected from the radicals of formula I in which r=1, a=0, p=1, GpR corresponds to formula II in which R equals —CH$_2$—CH$_2$—, GpC corresponds to formula IVd in which x=15 and Cx is

In an embodiment, the co-polyamino acid bearing carboxylate charges and hydrophobic radicals is a co-polyamino acid of formula VII or VIIa in which DP=35+/−5, i=0.05+/−0.02 and the at least one hydrophobic radical of formula I is selected from the radicals of formula I in which r=1, a=0, p=1, GpR corresponds to formula II in which R equals —CH$_2$—CH$_2$—, GpC corresponds to formula IVd in which x=16 and Cx is

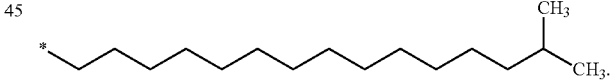

In an embodiment, the co-polyamino acid bearing carboxylate charges and hydrophobic radicals is a co-polyamino acid of formula VII or VIIa in which DP=23+/−5, i=0.05+/−0.02 and the at least one hydrophobic radical of formula I is selected from the radicals of formula I in which r=1, a=0, p=1, GpR corresponds to formula II in which R is

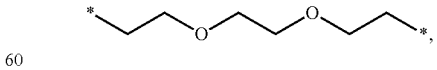

GpC corresponds to formula IVd in which x=17 and Cx is

In an embodiment, the co-polyamino acid bearing carboxylate charges and hydrophobic radicals is a co-polyamino acid of formula VII or VIIa in which DP=22+/−5, i=0.05+/−0.02 and the at least one hydrophobic radical of formula I is selected from the radicals of formula I in which r=1, a=0, p=1, GpR corresponds to formula II in which R is

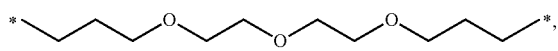

GpC corresponds to formula IVd in which x=19 and Cx is

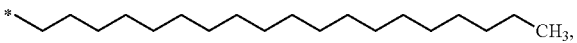 [SMILES: CCCCCCCCCCCCCCCCCCCC]

In an embodiment, the co-polyamino acid bearing carboxylate charges and hydrophobic radicals is a co-polyamino acid of formula VII or VIIa in which DP=30+/−5, i=0.10+/−0.03 and the at least one hydrophobic radical of formula I is selected from the radicals of formula I in which r=1, a=0, p=1, GpR corresponds to formula II in which R is

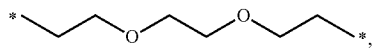

GpC corresponds to formula IVd in which x=15 and Cx is

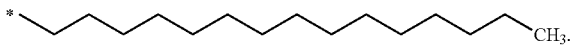

In an embodiment, the co-polyamino acid bearing carboxylate charges and hydrophobic radicals is a co-polyamino acid of formula VII or VIIa in which DP=23+/−5, i=0.07+/−0.02 and the at least one hydrophobic radical of formula I is selected from the radicals of formula I in which r=1, a=0, p=1, GpR corresponds to formula II in which R is

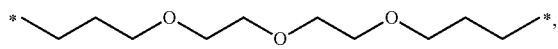

GpC corresponds to formula IVd in which x=15 and Cx is

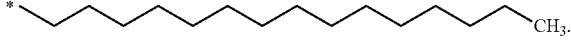 [SMILES: CCCCCCCCCCCCCCCC]

In an embodiment, the co-polyamino acid bearing carboxylate charges and hydrophobic radicals is a co-polyamino acid of formula VII or VIIa in which DP=23+/−5, i=0.05+/−0.02 and the at least one hydrophobic radical of formula I is selected from the radicals of formula I in which r=1, a=0, p=1, GpR corresponds to formula II in which R is

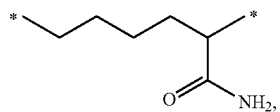

GpC corresponds to formula IVd in which x=15 and Cx is

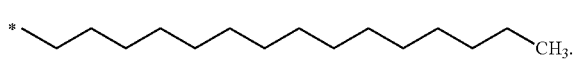 [SMILES: CCCCCCCCCCCCCCCC]

In an embodiment, the co-polyamino acid bearing carboxylate charges and hydrophobic radicals is a co-polyamino acid of formula VII or VIIa in which DP=26+/−5, i=0.04+/−0.02 and the at least one hydrophobic radical of formula I is selected from the radicals of formula I in which r=1, a=0, p=1, GpR corresponds to formula II in which R is —CH$_2$—CH$_2$—, GpC corresponds to formula IVa in which b=1, B is

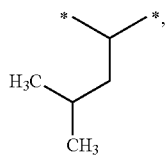

x=15 and Cx is

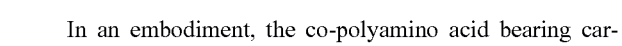

In an embodiment, the co-polyamino acid bearing carboxylate charges and hydrophobic radicals is a co-polyamino acid of formula VII or VIIa in which DP=35+/−5, i=0.13+/−0.04 and the at least one hydrophobic radical of formula I is selected from the radicals of formula I in which r=1, a=0, p=1, GpR corresponds to formula II in which R is —CH$_2$—CH$_2$—, GpC corresponds to formula IVa in which b=1, B is

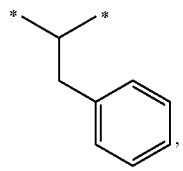

x=11 and Cx is

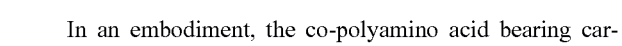

In an embodiment, the co-polyamino acid bearing carboxylate charges and hydrophobic radicals is a co-polyamino acid of formula VII or VIIa, in which DP=23+/−5, i=0.05+/−0.02 and the at least one hydrophobic radical of formula I is selected from the radicals of formula I in which r=1, a=0, p=1, GpR corresponds to formula II in which R is

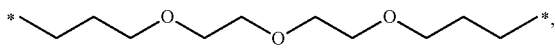

GpC corresponds to formula IVd in which x=19 and Cx is

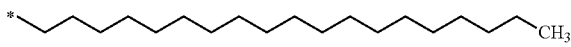 [SMILES: CCCCCCCCCCCCCCCCCCCC]

In an embodiment, the co-polyamino acid bearing carboxylate charges and hydrophobic radicals is a co-polyamino acid of formula VII or VIIb, in which DP=25+/−5, 0.033≤i≤0.05, and the hydrophobic radical of formula I is selected from the radicals of formula I in which r=1, a=0, p=1, GpR corresponds to formula II in which R is —CH$_2$—CH$_2$—, GpC corresponds to formula IVd in which x=15 and Cx is

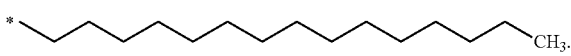

In an embodiment, the co-polyamino acid bearing carboxylate charges and hydrophobic radicals is a co-polyamino acid of formula VII or VIIb, in which DP=30+/−5, 0.028≤i≤0.04, and the at least one hydrophobic radical of formula I is selected from the radicals of formula I in which r=1, a=0, p=1, GpR corresponds to formula II in which R is

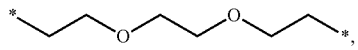

GpC corresponds to formula IVd in which x=17 and Cx is

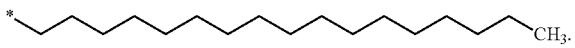

In an embodiment, the co-polyamino acid bearing carboxylate charges and hydrophobic radicals is a co-polyamino acid of formula VII or VIIb, in which DP=45+/−10, 0.018≤i≤0.028, and the at least one hydrophobic radical of formula I is selected from the radicals of formula f in which r=1, a=0, p=1, GpR corresponds to formula II in which R is

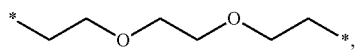

GpC corresponds to formula IVd in which x=17 is

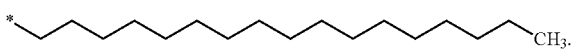

In an embodiment, the co-polyamino acid bearing carboxylate charges and hydrophobic radicals is a co-polyamino acid of formula VII or VIIb, in which DP=60+/−10, 0.014≤i≤0.02, and the at least one hydrophobic radical of formula I is selected from the radicals of formula I in which r=1, a=0, p=1, GpR corresponds to formula II in which R is GpC corresponds to formula IVd in which x=17 and Cx is

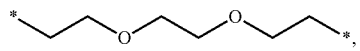

In an embodiment, the co-polyamino acid bearing carboxylate charges and hydrophobic radicals is a co-polyamino acid of formula VII or VIIb, in which DP=25+/−5, 0.033≤i≤0.05, and the hydrophobic radical of formula I is selected from the radicals of formula I in which r=1, a=0, p 1=, GpR corresponds to formula II in which R is

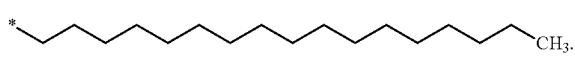

GpC corresponds to formula IVd in which x=19 and Cx is

In an embodiment, the co-polyamino acid bearing carboxylate charges and hydrophobic radicals is a co-polyamino acid of formula VII or VIIa in which DP=22+/−5, i=0.05+/−0.02 and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

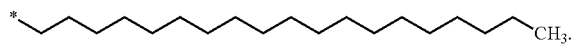

In an embodiment, the co-polyamino acid bearing carboxylate charges and hydrophobic radicals is a co-polyamino acid of formula VII or VIIa in which DP=35+/−5, i=0.05+/−0.02 and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

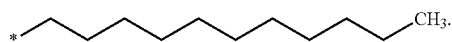

In an embodiment, the co-polyamino acid bearing carboxylate charges and hydrophobic radicals is a co-polyamino acid of formula VII or VIIa in which DP=65+/−5, i=0.05+/−0.02 and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

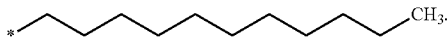

In an embodiment, the co-polyamino acid bearing carboxylate charges and hydrophobic radicals is a co-polyamino acid of formula VII or VIIa in which DP=22+/−5, i=0.04+/−0.02 and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=13 and Cx is

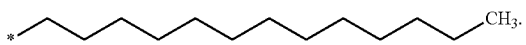

In an embodiment, the co-polyamino acid bearing carboxylate charges and hydrophobic radicals is a co-polyamino acid of formula VII or VIIa in which DP=22+/−5, 0.03+/−0.01 and the at least one hydrophobic radical of formula I is selected from the radicals of formula I in which r=1, a=1, p=2, GpR corresponds to formula II in which R is

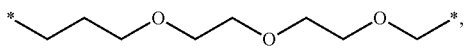

GpA corresponds to formula IIIb, GpC corresponds to formula IVd in which x=13 and Cx is

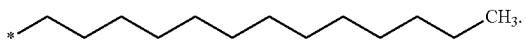 [SMILES: *CCCCCCCCCCCCC]

In an embodiment, the co-polyamino acid bearing carboxylate charges and hydrophobic radicals is a co-polyamino acid of formula VII or VIIa in which DP=22+/−5, i=0.07+/−0.02 and the at least one hydrophobic radical of formula I is selected from the radicals of formula I in which r=1, a=1, p=2, GpR corresponds to formula II in which R is

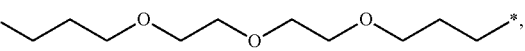

GpA corresponds to formula IIIb, GpC corresponds to formula IVd in which x=9 and Cx is

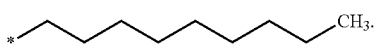

In an embodiment, the co-polyamino acid bearing carboxylate charges and hydrophobic radicals is a co-polyamino acid of formula VII or VIIb, in which DP=27+/−5, 0.031≤i≤0.045, and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

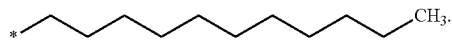

In an embodiment, the co-polyamino acid bearing carboxylate charges and hydrophobic radicals is a co-polyamino acid of formula VII or VIIb, in which DP=22+/−5, 0.037≤i≤0.055, and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=13 and Cx is

In an embodiment, the co-polyamino acid bearing carboxylate charges and hydrophobic radicals is a co-polyamino acid of formula VII or VIIb, in which DP=22+/−5, 0.037≤i≤0.055, and the at least one hydrophobic radical of formula I is selected from the radicals of formula I in which r=1, a=1, p=2, GpR corresponds to formula II in which R is

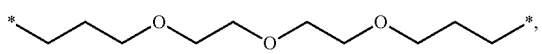

GpA corresponds to formula IIIb, GpC corresponds to formula IVd in which x=13 and Cx is

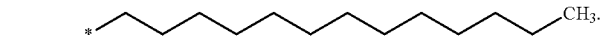 [SMILES: *CCCCCCCCCCCCC]

In an embodiment, the co-polyamino acid bearing carboxylate charges and hydrophobic radicals is a co-polyamino acid of formula VII or VIIb, in which DP=60+/−10, 0.014≤i≤0.02, and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=13 and Cx is

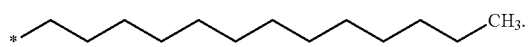

In an embodiment, the co-polyamino acid bearing carboxylate charges and hydrophobic radicals is a co-polyamino acid of formula VII or VIIb, in which DP=40+/−5, 0.022≤i≤0.029, and the at least one hydrophobic radical of formula I is selected from the radicals of formula I in which r=1, a=1, p=2, GpR corresponds to formula II in which R is —CH$_2$—CH$_2$—, A corresponds to formula IIIb, GpC corresponds to formula IVd in which x=13 and Cx is

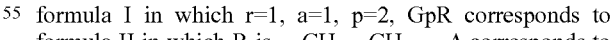

In an embodiment, the composition according to the invention is characterized in that the co-polyamino acid originates from a polyamino acid obtained by polymerization.

In an embodiment, the composition according to the invention is characterized in that the co-polyamino acid originates from a polyamino acid obtained by ring-opening polymerization of a glutamic acid N-carboxyanhydride derivative or an aspartic acid N-carboxyanhydride derivative.

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative described in the review article Adv. Polym. Sci. 2006, 202, 1-18 (Deming, T. J.).

In an embodiment, the composition according to the invention is characterized in that the co-polyamino acid originates from a polyamino acid obtained by polymerization of a glutamic acid N-carboxyanhydride derivative.

In an embodiment, the composition according to the invention is characterized in that the co-polyamino acid originates from a polyamino acid obtained by polymerization of a glutamic acid N-carboxyanhydride derivative selected from the group consisting of methyl glutamate N-carboxyanhydride (GluOMe-NCA), benzyl glutamate N-carboxyanhydride (GluOBzl-NCA), and t-butyl glutamate N-carboxyanhydride (GluOtBu-NCA).

In an embodiment, the glutamic acid N-carboxyanhydride derivative is methyl L-glutamate N-carboxyanhydride (L-GluOMc-NCA).

In an embodiment, the glutamic acid N-carboxyanhydride derivative is benzyl L-glutamate N-carboxyanhydride (L-GluOBzl-NCA).

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative using, using as initiator, an organometallic complex of a transition metal, as described in the publication Nature 1997, 390, 386-389 (Deming, T J.).

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative, using, as initiator, ammonia or a primary amine as described in the patent FR 2,801,226 (Touraud, F. et al.) and the references cited in this patent.

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative, using as initiator hexamethyldisilazane, as described in the publication J. Am. Chem. Soc. 2007, 129, 14114-14115 (Lu H. et al.) or a silylated amine as described in the publication J. Am. Chem. Soc. 2008, 130, 12562-12563 (Lu H. et al.).

In an embodiment, the composition according to the invention is characterized in that the method for synthetizing the polyamino acid obtained by polymerization of a glutamic acid N-carboxyanhydride derivative or an aspartic acid N-carboxyanhydride derivative from which the co-polyamino acid originates comprises a step of hydrolysis of ester functions.

In an embodiment, this step of hydrolysis of ester functions can consist of a hydrolysis in an acidic medium or a hydrolysis in an alkaline medium or it can be carried out by hydrogenation.

In an embodiment, this step of hydrolysis of ester groups is a hydrolysis in an acidic medium.

In an embodiment, this step of hydrolysis of ester groups is carried out by hydrogenation.

In an embodiment, the composition according to the invention is characterized in that the co-polyamino acid originates from a polyamino acid obtained by depolymerization of a polyamino acid of higher molecular weight.

In an embodiment, the composition according to the invention is characterized in that the co-polyamino acid originates from a polyamino acid obtained by enzymatic depolymerization of a polyamino acid of higher molecular weight.

In an embodiment, the composition according to the invention is characterized in that the co-polyamino acid originates from a polyamino acid obtained by chemical depolymerization of a polyamino acid of higher molecular weight.

In an embodiment, the composition according to the invention is characterized in that the co-polyamino acid originates from a polyamino acid obtained by enzymatic and chemical depolymerization of a polyamino acid of higher molecular weight.

In an embodiment, the composition according to the invention is characterized in that the co-polyamino acid originates from a polyamino acid obtained by depolymerization of a polyamino acid of higher molecular weight selected from the group consisting of sodium polyglutamate and sodium polyaspartate.

In an embodiment, the composition according to the invention is characterized in that the co-polyamino acid originates from a polyamino acid obtained by depolymerization of a sodium polyglutamate of higher molecular weight.

In an embodiment, the composition according to the invention is characterized in that the co-polyamino acid originates from a polyamino acid obtained by depolymerization of a sodium polyaspartate of higher molecular weight.

In an embodiment, the composition according to the invention is characterized in that the co-polyamino acid is obtained by grafting a hydrophobic group onto a poly-L-glutamic acid or poly-L-aspartic acid using the methods for forming amide bonds, which are well known to the person skilled in the art.

In an embodiment, the composition according to the invention is characterized in that the co-polyamino acid is obtained by grafting of a hydrophobic group onto a poly-L-glutamic acid or poly-L-aspartic acid using the methods for forming amide bonds, used for peptide synthesis.

In an embodiment, the composition according to the invention is characterized in that the co-polyamino acid is obtained by grafting of a hydrophobic group onto a poly-L-glutamic acid or poly-L-aspartic acid as described in the patent FR 2,840,614 (Chan, Y. P.; et al.).

In an embodiment, the concentration of co-polyamino acid bearing carboxylate charges and hydrophobic radicals is at most 40 mg/mL.

In an embodiment, the concentration of co-polyamino acid bearing carboxylate charges and hydrophobic radicals is at most 30 mg/mL.

In an embodiment, the concentration of co-polyamino acid bearing carboxylate charges and hydrophobic radicals is at most 20 mg/mL.

In an embodiment, the concentration of co-polyamino acid bearing carboxylate charges and hydrophobic radicals is at most 10 mg/mL.

In an embodiment, the concentration of co-polyamino acid bearing carboxylate charges and hydrophobic radicals is at most 5 mg/mL.

In an embodiment, the concentration of co-polyamino acid bearing carboxylate charges and hydrophobic radicals is at most 2.5 mg/mL.

In an embodiment, the concentration of co-polyamino acid bearing carboxylate charges and hydrophobic radicals is at most 1 mg/mL.

In an embodiment, the concentration of co-polyamino acid bearing carboxylate charges and hydrophobic radicals is at most 0.5 mg/mL.

In an embodiment, the weight ratio of co-polyamino acid bearing carboxylate charges and hydrophobic radicals over glucagon is from 1.5 to 25.

In an embodiment, the weight ratio of co-polyamino acid bearing carboxylate charges and hydrophobic radicals over glucagon is from 2 to 20.

In an embodiment, the weight ratio of co-polyamino acid bearing carboxylate charges and hydrophobic radicals over glucagon is from 2.5 to 15.

In an embodiment, the weight ratio of co-polyamino acid bearing carboxylate charges and hydrophobic radicals over glucagon is from 2 to 10.

In an embodiment, the weight ratio of co-polyamino acid bearing carboxylate charges and hydrophobic radicals over glucagon is from 2 to 7.

Human glucagon is used at doses that vary depending on the applications.

In the emergency treatment of hypoglycemia, the recommended dosage is 1 mg by the intramuscular or intravenous route (0.5 mg if the body weight is less than 25 kg). This administration is carried out with a solution of human glucagon at the concentration of 1 mg/mL.

In pumps, the daily dose considered is approximately 0.5 mg; thus the solutions can comprise from 0.25 mg/mL to 5 mg/mL of human glucagon.

In an embodiment, the solutions can comprise from 0.5 mg/mL to 3 mg/mL of human glucagon.

In the treatment of obesity, the daily dose considered is approximately 0.5 mg, the solutions thus can comprise from 0.25 mg/mL to 5 mg/mL of human glucagon.

In an embodiment, the concentration of human glucagon is from 0.25 to 5 mg/mL.

In an embodiment, the concentration of human glucagon is from 0.5 to 4 mg/mL.

In an embodiment, the concentration of human glucagon is from 0.75 to 3 mg/mL.

In an embodiment, the concentration of human glucagon is from 0.75 to 2.5 mg/mL.

In an embodiment, the concentration of human glucagon is from 0.75 to 2 mg/mL.

In an embodiment, the concentration of human glucagon is from 1 to 2 mg/mL.

In an embodiment, the molar ratio [hydrophobic radical]/[human glucagon] is less than 20.

In an embodiment, the molar ratio [hydrophobic radical]/[human glucagon] is less than 15.

In an embodiment, the molar ratio [hydrophobic radical]/[human glucagon] is less than 10.

In an embodiment, the molar ratio [hydrophobic radical]/[human glucagon] is less than 5.

In an embodiment, the molar ratio [hydrophobic radical]/[human glucagon] is less than 2.5.

In an embodiment, the molar ratio [hydrophobic radical]/[human glucagon] is less than 1.5.

Human glucagon is a highly preserved polypeptide comprising a simple chain of 29 amino acid residues having the following sequence H-His-Ser-Gln-Gly-Thr-Phe-Thr-Ser-Asp-Tyr-Ser-Lys-Tyr-Leu-Asp-Ser-Arg-Arg-Ala-Gn-Asp-Phe-Val-Gn-Trp-Leu-Met-Asn-Thr-OH.

It can be obtained in different manners, by recombinant peptide synthesis.

Human glucagon is available from numerous sources. For example, the human glucagon produced by Bachem via peptide synthesis is available, in particular under reference 407473.

In an embodiment, the composition comprises, in addition, a nicotinic compound or one of the derivatives thereof.

In an embodiment, the composition comprises nicotinamide.

In an embodiment, the concentration of nicotinamide ranges from 10 to 160 mM.

In an embodiment, the concentration of nicotinamide ranges from 20 to 150 mM.

In an embodiment, the concentration of nicotinamide ranges from 40 to 120 mM.

In an embodiment, the concentration of nicotinamide ranges from 60 to 100 mM.

In an embodiment, the composition comprises, in addition, a polyanionic compound In an embodiment, the polyanionic compound is selected from the group consisting of the carboxylic polyacids and the $Na^+$, $K^+$, $Ca^{2+}$ or $Mg^{2+}$ salts thereof.

In an embodiment, the carboxylic acid is selected from the group consisting of citric acid, tartaric acid and the $Na^+$, $K^+$, $Ca^{2+}$ or $Mg^{2+}$ salts thereof.

In an embodiment, the polyanionic compound is selected from the group consisting of the phosphoric polyacids and the $Na^+$, $K^+$, $Ca^{2+}$ or $Mg^{2+}$ salts thereof.

In an embodiment, the phosphoric polyacid is triphosphate and the $Na^+$, $K^+$, $Ca^{2+}$ or $Mg^{2+}$ salts thereof.

In an embodiment, the polyanionic compound is citric acid and the $Na^+$, $K^+$, $Ca^{2+}$ or $Mg^{2+}$ salts thereof.

In an embodiment, the polyanionic compound is tartaric acid and the $Na^+$, $K^+$, $Ca^{2+}$ or $Mg^{2+}$ salts thereof.

In an embodiment, the polyanionic compound is triphosphoric acid and the $Na^+$, $K^+$, $Ca^{2+}$ or $Mg^{2+}$ salts thereof.

In an embodiment, the concentration of polyanionic compound is from 1 to 20 mM.

In an embodiment, the concentration of polyanionic compound is from 2 to 15 mM.

In an embodiment, the concentration of polyanionic compound is from 3 to 12 mM.

In an embodiment, the concentration of polyanionic compound is 10 mM.

In an embodiment, the concentration of polyanionic compound is 5 mM.

In an embodiment, the concentration of polyanionic compound is 10 mM for concentrations of glucagon from 0.5 mg/mL to 3 mg/mL.

In an embodiment, the concentration of polyanionic compound is 10 mM for concentrations of glucagon from 0.5 mg/mL to 2 mg/mL.

In an embodiment, the concentration of polyanionic compound is 10 mM for concentrations of glucagon from 1 mg/mL to 2 mg/mL.

In an embodiment, the concentration of polyanionic compound is 5 mM for concentrations of glucagon from 0.5 mg/mL to 3 mg/mL.

In an embodiment, the concentration of polyanionic compound is 5 mM for concentrations of glucagon from 0.5 mg/mL to 2 mg/mL.

In an embodiment, the concentration of polyanionic compound is 5 mM for concentrations of glucagon from 1 mg/mL to 2 mg/mL.

In an embodiment, the concentration of citric acid and the $Na^+$, $K^+$, $Ca^{2+}$ or $Mg^{2+}$ salts thereof is from 1 to 20 mM.

In an embodiment, the concentration of citric acid and the $Na^+$, $K^+$, $Ca^{2+}$ or $Mg^{2+}$ salts thereof is from 2 to 15 mM.

In an embodiment, the concentration of citric acid and the $Na^+$, $K^+$, $Ca^{2+}$ or $Mg^{2+}$ salts thereof is from 3 to 12 mM.

In an embodiment, the concentration of citric acid and the $Na^+$, $K^+$, $Ca^{2+}$ or $Mg^{2+}$ salts thereof is 10 mM.

In an embodiment, the concentration of citric acid and the $Na^+$, $K^+$, $Ca^{2+}$ or $Mg^{2+}$ salts thereof is 5 mM.

In an embodiment, the concentration of citric acid and the $Na^+$, $K^+$, $Ca^{2+}$ or $Mg^{2+}$ salts thereof is 10 mM for concentrations of glucagon from 0.5 mg/mL to 3 mg/mL.

In an embodiment, the concentration of citric acid and the $Na^+$, $K^+$, $Ca^{2+}$ or $Mg^{2+}$ salts thereof is 10 mM for concentrations of glucagon from 0.5 mg/mL to 2 mg/mL.

In an embodiment, the concentration of citric acid and the $Na^+$, $K^+$, $Ca^{2+}$ or $Mg^{2+}$ salts thereof is 10 mM for concentrations of glucagon from 1 mg/mL to 2 mg/mL.

In an embodiment, the concentration of citric acid and the $Na^+$, $K^+$, $Ca^{2+}$ or $Mg^{2+}$ salts thereof is 5 mM for concentrations of glucagon from 0.5 mg/mL to 3 mg/mL.

In an embodiment, the concentration of citric acid and the $Na^+$, $K^+$, $Ca^{2+}$ or $Mg^{2+}$ salts thereof is 5 mM for concentrations of glucagon from 0.5 mg/mL to 2 mg/mL.

In an embodiment, the concentration of citric acid and the $Na^+$, $K^+$, $Ca^{2+}$ or $Mg^{2+}$ salts thereof is 5 mM for concentrations of glucagon from 1 mg/mL to 2 mg/mL.

In an embodiment, the compositions according to the invention comprise, in addition, a gastrointestinal hormone.

"Gastrointestinal hormones" is understood to mean the hormones selected from the group consisting of the GLP-1 RA for agonists of the human glucagon-like peptide-1 receptor (glucagon like peptide-1 receptor agonist) and GIP (glucose-dependent insulinotropic peptide), oxyntomodulin (a derivative of human proglucagon), peptide YY, amylin, cholecystokinin, pancreatic polypeptide (PP), ghrelin and enterostatin, the analogs or derivatives thereof and/or the pharmaceutically acceptable salts thereof.

In an embodiment, the gastrointestinal hormones are analogs or derivatives of GLP-1 RA (Glucagon like peptide-1 receptor agonist) selected from the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), the analogs or derivatives thereof and the pharmaceutically acceptable salts thereof.

In an embodiment, the gastrointestinal hormone is pramlintide or Symlin® (ASTRA-ZENECA).

In an embodiment, the gastrointestinal hormone is exenatide or Byetta®, the analogs or derivatives thereof and the pharmaceutically acceptable salts thereof.

In an embodiment, the gastrointestinal hormone is liraglutide or Victoza®, the analogs or derivatives thereof and the pharmaceutically acceptable salts thereof.

In an embodiment, the gastrointestinal hormone is lixisenatide or Lyxumia®, the analogs or derivatives thereof and the pharmaceutically acceptable salts thereof.

In an embodiment, the gastrointestinal hormone is albiglutide or Tanzeum®, the analogs or derivatives thereof and the pharmaceutically acceptable salts thereof.

In an embodiment, the gastrointestinal hormone is dulaglutide or Trulicity®, the analogs or derivatives thereof and the pharmaceutically acceptable salts thereof.

In an embodiment, the gastrointestinal hormone is pramlintide or Symlin®, the analogs or derivatives thereof and the pharmaceutically acceptable salts thereof.

"Analog," when used in reference to a peptide or a protein, is understood to mean a peptide or a protein in which one or more constitutive residues of amino acids have been substituted by other residues of amino acids and/or in which one or more constitutive residues of amino acids have been eliminated and/or in which one or more constitutive residues of amino acids have been added. The admissible percentage of homology for the present definition of an analog is 50%.

"Derivative," when used in reference to a peptide or a protein, is understood to mean a peptide or a protein or an analog which has been chemically modified by a substituent which is not present in the peptide or the protein or the analog of reference, that is to say a peptide or a protein which has been made by creation of covalent bonds, in order to introduce substituents.

In an embodiment, the substituent is selected from the group consisting of the fatty chains.

In an embodiment, the concentration of gastrointestinal hormone is within a range from 0.01 to 10 mg/mL.

In an embodiment, the concentration of exenatide, the analogs or derivatives thereof and the pharmaceutically acceptable salts thereof is within a range from 0.04 to 0.5 mg/mL.

In an embodiment, the concentration of liraglutide, the analogs or derivatives thereof and the pharmaceutically acceptable salts thereof is within a range from 1 to 10 mg/mL.

In an embodiment, the concentration of lixisenatide, the analogs or derivatives thereof and the pharmaceutically acceptable salts thereof is within a range from 0.01 to 1 mg/mL.

In an embodiment, the concentration of pramlintide, the analogs or derivatives thereof and the pharmaceutically acceptable salts thereof is within a range from 0.1 to 5 mg/mL.

In an embodiment, the compositions according to the invention are produced by mixing of human glucagon solutions obtained by reconstitution of lyophilizate and of solutions of GLP-1 RA (Glucagon like peptide-1 receptor agonist) GLP-1 RA, of analog or of derivative of GLP-1 RA, said solutions of GLP-1 RA being commercial or reconstituted from lyophilizate.

In an embodiment, the compositions according to the invention comprise, in addition, buffers.

In an embodiment, the compositions according to the invention comprise buffers at concentrations from 0 to 100 mM.

In an embodiment, the compositions according to the invention comprise buffers at concentrations from 15 to 50 mM.

In an embodiment, the compositions according to the invention comprise a buffer selected from the group consisting of a phosphate buffer, Tris (trishydroxymethylaminomethane) or sodium citrate.

In an embodiment, the buffer is sodium phosphate.

In an embodiment, the buffer is Tris (trishydroxymethylaminomethane).

In an embodiment, the buffer is sodium citrate.

In an embodiment, the composition comprises, in addition, a zinc salt, in particular zinc chloride.

In an embodiment, the concentration of zinc salt is from 50 to 5000 µM.

In an embodiment, the concentration of zinc salt is from 100 to 2000 μM.

In an embodiment, the concentration of zinc salt is from 200 to 1500 μM.

In an embodiment, the concentration of zinc salt is from 200 to 1000 μM.

In an embodiment, the zinc concentration is such that the molar ratio [zinc]/[glucagon] is from 0.1 to 2.5.

In an embodiment, the zinc concentration is such that the molar ratio [zinc]/[glucagon] is from 0.2 to 2.

In an embodiment, the zinc concentration is such that the molar ratio [zinc]/[glucagon] is from 0.5 to 1.5.

In an embodiment, the zinc concentration is such that the molar ratio [zinc]/[glucagon] is 1.

In an embodiment, the compositions according to the invention comprise, in addition, preservatives.

In an embodiment, the preservatives are selected from the group consisting of m-cresol and phenol, alone or in a mixture.

In an embodiment, the compositions according to the invention comprise, in addition, antioxidants.

In an embodiment, the antioxidants are selected from methionine.

In an embodiment, the concentration of preservatives is from 10 to 50 mM.

In an embodiment, the concentration of preservatives is from 10 to 40 mM.

In an embodiment, the compositions according to the invention comprise, in addition, a surfactant.

In an embodiment, the surfactant is selected from the group consisting of propylene glycol or polysorbate.

The compositions according to the invention can, in addition, comprise additives such as tonicity agents.

In an embodiment, the tonicity agents are selected from the group consisting of sodium chloride, mannitol, saccharose, sorbitol and glycerol.

The compositions according to the invention can comprise, in addition, all the excipients in accordance with the pharmacopoeias and compatible with human glucagon and the GLP-1 RA used at the conventional concentrations.

The invention also relates to a pharmaceutical composition according to the invention, characterized in that it is obtained by drying and/or lyophilization.

In the case of local and systemic releases, the modes of administration considered are by intravenous, subcutaneous, intradermal or intramuscular route.

The transdermal, oral, nasal, vaginal, ocular, buccal, pulmonary routes of administration are also considered.

The invention also relates to single-dose formulations at pH from 6.6 to 7.8 comprising human glucagon.

The invention also relates to single-dose formulations at a pH from 6.6 to 7.8 comprising human glucagon and a gastrointestinal hormone, as defined above.

In an embodiment, the single-dose formulations comprise, in addition, a substituted co-polyamino acid as defined above.

In an embodiment, the formulations are in the form of an injectable solution. In an embodiment, the GLP-1 RA, analog or derivative of GLP-1 RA is selected from the group comprising exenatide (Byetta®), liraglutide (Victoza®), lixisenatide (Lyxumia®), albiglutide (Tanzeum®), dulaglutide (Trulicity®) or one of the derivatives thereof.

In an embodiment, the gastrointestinal hormone is exenatide.

In an embodiment, the gastrointestinal hormone is liraglutide.

In an embodiment, the gastrointestinal hormone is lixisenatide.

In an embodiment, the gastrointestinal hormone is albiglutide.

In an embodiment, the gastrointestinal hormone is dulaglutide.

Moreover and just as importantly, the applicant was able to verify that human glucagon in the presence of a co-polyamino acid bearing carboxylate charges and at least one hydrophobic radical according to the invention preserves its action, whether alone or in combination with a gastrointestinal hormone.

The preparation of a composition according to the invention has the advantage that it can be carried out by simple mixing of a solution of human glucagon, of a solution of GLP-1 RA, of an analog or a derivative of GLP-1 RA, and of a co-polyamino acid bearing carboxylate charges and at least one hydrophobic radical according to the invention, in aqueous solution or in lyophilized form. If necessary, the pH of the preparation is adjusted to pH 7.

In an embodiment, the mixture of human glucagon and of substituted co-polyamino acid is concentrated by ultrafiltration before the mixing with GLP-1 RA, an analog or a derivative of GLP-1 RA in aqueous solution and in lyophilized form.

If necessary, the composition of the mixture is adjusted in terms of excipients such as glycerol, m-cresol and polysorbate (Tween®) by addition of concentrated solutions of these excipients within the mixture. If necessary, the pH is adjusted to 7.

Part A

AA: Synthesis of the Hydrophobic Molecules in which p=1

The hydrophobic radicals are represented in the following table by the corresponding hydrophobic molecule before grafting onto the co-polyamino acid.

TABLE 1A list and structures of the hydrophobic molecules synthesized according to the invention.

| No. | Structure of the hydrophobic molecule before grafting onto the co-polyamino acid |
|---|---|
| AA1 | 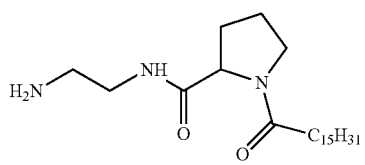 |

TABLE 1A-continued
list and structures of the hydrophobic molecules synthesized according to the invention.
| No. | Structure of the hydrophobic molecule before grafting onto the co-polyamino acid |
|---|---|
| AA2 | 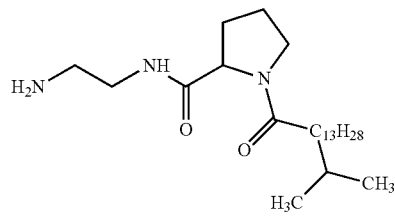 |
| AA3 | 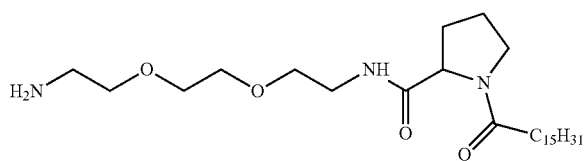 |
| AA4 | 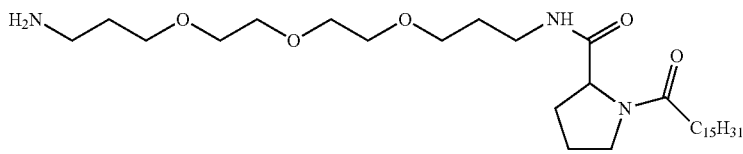 |
| AA5 | 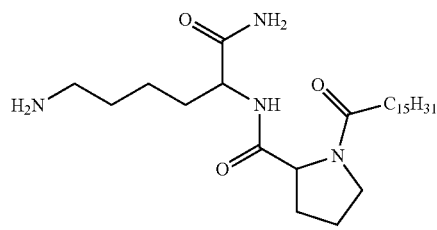 |
| AA6 | 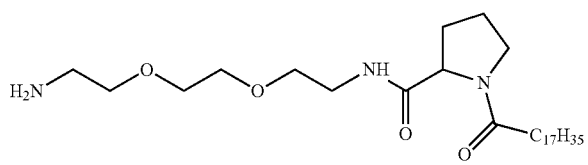 |
| AA7 | 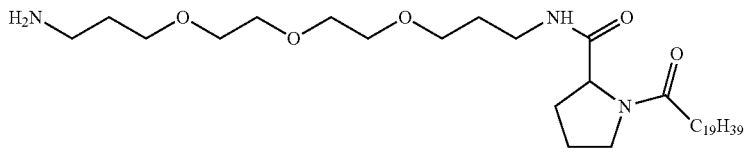 |
| AA8 | 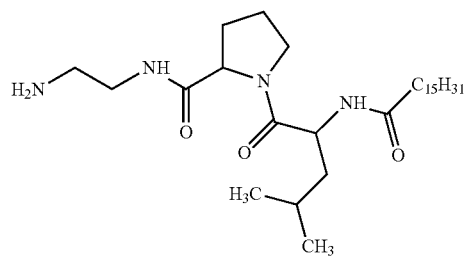 |

TABLE 1A-continued list and structures of the hydrophobic molecules synthesized according to the invention.

| No. | Structure of the hydrophobic molecule before grafting onto the co-polyamino acid |
|---|---|
| AA9 | 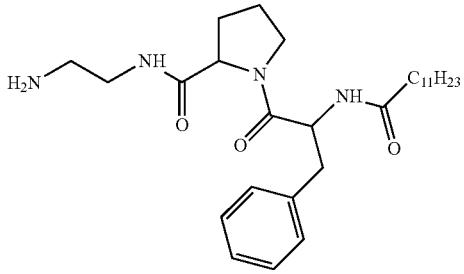 |
| AA10 | 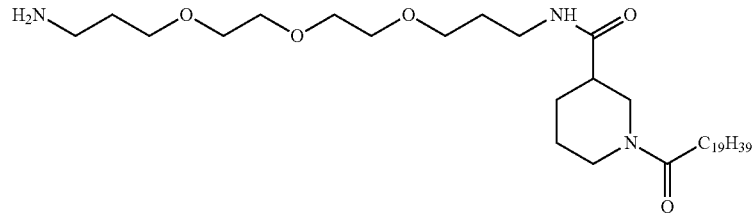 |
| AA12 | 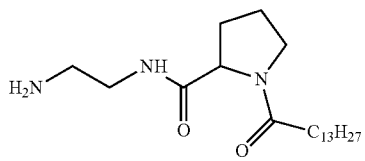 |
| AA14 | 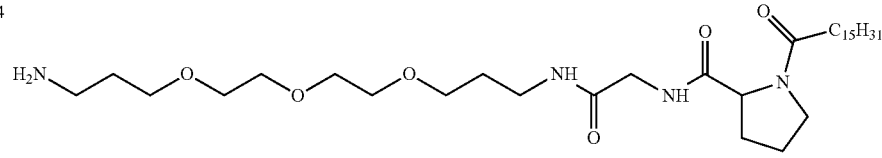 |

EXAMPLE AA1: MOLECULE AA1

Molecule A1: Product Obtained by the Reaction Between Palmitoyl Chloride and L-Proline.

A solution of palmitoyl chloride (23.0 g, 83.7 mmol) in acetone (167 mL) is added dropwise within 90 minutes to a solution of L-proline (10.6 g, 92.1 mmol) in 1 N aqueous sodium hydroxide (230 mL; 230 mmol). After 14 h of stirring at room temperature, the heterogeneous mixture is cooled to 0° C., then filtered through a sintered filter to yield a white solid which is washed with water (2×100 mL), then diisopropyl ether (100 mL). The solid is dried at reduced pressure. The solid is then dissolved at reflux in 200 mL of water, then 8 mL of 37% hydrochloric acid solution are added until obtaining pH=1. The opalescent reaction mixture is then cooled to 0° C. The precipitate obtained is filtered through a sintered filter, then washed with water (5×50 mL) until filtrates of physiological pH from 6.0 to 8.0 are obtained, to be dried subsequently in an oven at 50° C. under a vacuum overnight. The product is purified by recrystallization in diisopropyl ether. A white solid is obtained.

Yield: 22.7 g (77%).

$^1$H NMR (CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

Molecule A2: Product Obtained by Reaction Between Molecule A1 and Boc-Ethylenediamine.

N,N-diisopropylethylamine (DIPEA) (68.8 g, 532.3 mmol), 1-hydroxybenzotriaolze (HOBt) (37.1 g, 274.6 mmol), then N-(3-dimethylaminopropyl)-N'-ethylcarbodiimide (EDC) (53.1 g, 277.0 mmol) are added successively and at room temperature to a solution of molecule A1 (75.1 g, 212.4 mmol) in 1500 mL of chloroform. After 15 minutes of stirring at room temperature, a solution of Boc-ethylenediamine (Boc-ethylenediamine) (37.6 g, 234.7 mmol) in 35 mL of chloroform is added. After 18 h of stirring at room temperature, a 0.1 N HCl solution (2.1 L), then a saturated NaCl solution (1 L) are added. The phases are separated, then the organic phase is washed successively with a 0.1 N HCl/saturated NaCl solution (2.1 L/1 L), a saturated NaCl solution (2 L), a saturated NaHCO$_3$ solution (2 L), then a saturated NaCl solution (2 L). The organic phase is dried over anhydrous sodium sulfate, filtered, then concentrated at reduced pressure. The solid obtained is purified by triturations in diisopropyl ether (3×400 mL), to yield a solid after drying under a vacuum at 40° C.

Yield: 90.4 g (86%).

$^1$H NMR (CDCl$_3$, ppm): 0.88 (3H); 1.20-1.37 (24H); 1.44 (9H); 1.54-1.70 (2H); 1.79-1.92 (1H); 1.92-2.04 (1H); 2.03-2.17 (1H); 2.17-2.44 (3H); 3.14-3.36 (4H); 3.43 (1H); 3.56 (1H); 4.29 (0.1H); 4.51 (0.9H); 4.82 (0.1H); 5.02 (0.9H); 6.84 (0.1H); 7.22 (0.9H).

Molecule AA1

A 4 M hydrochloric acid solution in dioxane (100 mL, 400 mmol) is added dropwise at 0° C. to a solution of molecule A2 (20.1 g, 40.5 mmol) in 330 mL of dichloromethane. After 3 h 30 of stirring at room temperature, the solution is concentrated at reduced pressure. The residue is purified by flash chromatography (methanol, dichloromethane) to yield a white solid of molecule AA1 in hydrochloride salt form.

Yield: 16.3 g (93%).

$^1$H NMR (CDCl$_3$, ppm): 0.88 (3H); 1.07-1.40 (24H); 1.49-1.63 (2H); 1.77-2.18 (4H); 2.18-2.45 (2H); 3.14-3.32 (2H); 3.42-3.63 (2H); 3.63-3.84 (2H); 4.37 (0.1H); 4.48 (0.9H); 6.81-8.81 (4H).

LC/MS (ESI): 396.5; (calculated ([M+H]$^+$): 396.4).

EXAMPLE AA2: MOLECULE AA2

Molecule A3: 15-methylhexadecan-1-ol.

Magnesium (9.46 g, 389 mmol) in the form of chips is introduced into a three-neck flask under argon. The magnesium is covered with anhydrous THF (40 mL), and a few drops of 1-bromo-3-methylbutane are added at room temperature to initiate the reaction. After the observation of an exothermic reaction and slight turbidity of the medium, the rest of the 1-bromo-3-methylbutane (53.87 g, 357 mmol) is added dropwise within 90 min, while the temperature of the medium remains stable from 50 to 60° C. The reaction medium is then heated at 70° C. for 2 h.

A solution of 12-bromo-1-dodecanol (43 g, 162.1 mmol) in THF (60 mL) is added dropwise to a solution of CuCl (482 mg, 4.86 mmol) dissolved in NMP (62 mL) at 0° C. in a three-neck flask are argon. The solution of extemporaneously prepared hot organic magnesium solution is then added dropwise to this solution in a manner so as to maintain the temperature of the medium below 20° C. The mixture is then stirred at room temperature for 16 h. The medium is cooled to 0° C. and the reaction is stopped by addition of a 1N aqueous HCl solution until the pH is 1, and the medium is extracted with ethyl acetate. After washing of the organic phase with a saturated NaCl solution and drying over Na$_2$SO$_4$, the solution is filtered and concentrated under a vacuum to yield an oil. After purification by DCVC on a silica gel (cyclohexane, ethyl acetate), an oil which crystallizes at room temperature is obtained.

Yield: 32.8 g (74%)

$^1$H NMR (CDCl$_3$, ppm): 0.87 (6H); 1.14 (2H); 1.20-1.35 (22H); 1.50-1.55 (3H); 3.64 (2H).

Molecule A4: 15-methylhexadecanoic acid.

Potassium permanganate (38.2 g, 241.5 mmol) is added in small portions to a solution of molecule A3 (20.65 g, 80.5 mmol) and tetrabutylammonium bromide (14.02 g, 42.5 mmol) in a mixture of acetic acid/dichloroethane/water (124/400/320 mL) at room temperature. After stirring at reflux for 5 h and return to room temperature, the medium is acidified at pH 1 by gradual addition of 5N HCl. Na$_2$SO$_3$ (44.6 g, 354.3 mmol) is then added gradually until discoloration of the medium. The aqueous phase is extracted with dichloromethane, and the combined organic phases are dried over Na$_2$SO$_4$, filtered and concentrated under a vacuum. After purification by chromatography on silica gel (cyclohexane, ethyl acetate, acetic acid), a white solid is obtained.

Yield: 19.1 g (quantitative)

$^1$H NMR (CDCl$_3$, ppm): 0.87 (6H); 1.14 (2H); 1.22-1.38 (20H); 1.51 (1H); 1.63 (2H); 2.35 (2H).

Molecule A5: Product Obtained by Reaction Between Molecule A4 and L-Proline.

Dicyclohexyl carbodiimide (DCC) (8.01 g, 38.8 mmol) and N-hydroxysuccinimide (NHS) (4.47 g, 38.8 mmol) are added successively to a solution of molecule A4 (10 g, 37 mmol) in THF (360 mL) at 0° C. After 17 h of stirring at room temperature, the medium is cooled to 0° C. for 20 min, filtered through a sintered filter. L-Proline (4 g, 37.7 mmol), trimethylamine (34 mL) and water (30 mL) are added to the filtrate. After stirring at room temperature for 20 h, the medium is treated with a 1N aqueous HCl solution until the pH is 1. The aqueous phase is extracted with dichloromethane (2×125 ml). The combined organic phases are washed with a 1N aqueous HCl solution (2×100 ml), water (100 mL), then a saturated aqueous NaCl solution (100 mL). After drying over Na$_2$SO$_4$, the organic phase is filtered, concentrated under a vacuum, and the residue is purified by chromatography on silica gel (cyclohexane, ethyl acetate, acetic acid).

Yield: 9.2 g (72%)

$^1$H NMR (CDCl$_3$, ppm): 0.86 (6H); 1.14 (2H); 1.22-1.38 (20H); 1.50 (1H); 1.67 (2H); 1.95-2.10 (3H); 2.34 (2H); 2.49 (1H); 3.47 (1H); 3.56 (1H); 4.61 (1H).

LC/MS (ESI): 368.3; (calculated ([M+H]$^+$): 368.6).

Molecule A6: Product Obtained by Reaction Between Molecule A5 and Boc-Ethylenediamine.

Triethylamine (TEA) (5.23 mL) and 2-(1H-benzotriazol-1-yl)-1,1,3,3-tetramethyluronium tetrafluoroborate (TBTU) at room temperature are added to a solution of molecule A5 (9.22 g, 25.08 mmol) in a mixture of THF/DMF (200/50 mL). After 10 min of stirring, Boc-ethylenediamine (4.42 g, 27.6 mmol) is added. After stirring at room temperature for 17 h, the mixture is diluted with water (300 mL) at 0° C. and cold stirred for 20 min. The precipitate formed is filtered through a sintered filter, and the filtrate is extracted with ethyl acetate. The combined organic phases are washed with a saturated solution of NaHCO$_3$, washed over Na$_2$SO$_4$, filtered, concentrated under a vacuum, and the residue is purified by flash chromatography (ethyl acetate, methanol).

Yield: 6.9 g (54%)

$^1$H NMR (CDCl$_3$, ppm): 0.86 (6H); 1.15 (2H); 1.22-1.38 (20H); 1.43 (9H); 1.50 (1H); 1.64 (4H); 1.85 (1H); 1.95 (1H); 2.10 (1H); 2.31 (2H); 3.20-3.35 (3H); 3.45 (1H); 3.56 (1H); 4.51 (In); 5.05 (1H); 7.24 (1H).

LC/MS (ESI): 510.6; (calculated ([M+H]$^+$): 510.8).

Molecule AA2

A 4N HCl solution in dioxane (13 mL) is added to a solution of molecule A6 (5.3 g, 10.40 mmol) in dichloromethane (50 mL) at 0° C. After 5 h of stirring at 0° C., the medium is concentrated under a vacuum, taken up in water and lyophilized to yield a white solid of molecule AA2 in hydrochloride salt form.

Yield: 4.6 g (99%)

$^1$H NMR (D$_2$O, ppm): 0.91 (6H); 1.22 (2H); 1.22-1.50 (20H); 1.63 (3H); 1.98 (1H); 2.10 (2H); 2.26 (1H); 2.39 (1H); 2.43 (1H); 3.22 (2H); 3.45-3.60 (3H); 3.78 (1H); 4.42 (1H).

LC/MS (ESI): 410.4; (calculated ([M+H]$^+$): 410.7).

EXAMPLE AA3: MOLECULE AA3

Molecule A7: Product Obtained by the Reaction Between Molecule A1 and Boc-tri(ethylene glycol)diamine.

By a method similar to the one used for the preparation of molecule A2, applied to molecule A1 (4.0 g, 11.3 mmol) and to Boc-tri(ethylene glycol)diamine (3.1 g, 12.4 mmol), a colorless oil is obtained after purification by flash chromatography (methanol, toluene).

Yield: 5.5 g (84%).

$^1$H NMR (CDCl$_3$, ppm): 0.88 (3H); 1.09-1.39 (24H); 1.44 (9H); 1.64 (2H); 1.79-2.01 (2H); 2.06-2.43 (4H); 3.23-3.68 (14H); 4.33 (0.2H); 4.56 (0.8H); 5.25 (1H); 6.49 (0.2H); 7.13-7.50 (0.8H).

Molecule AA3

By a method similar to the one used for the preparation of molecule AA1, applied to molecule A7 (5.5 g, 9.4 mmol), a white solid of molecule AA3 in hydrochloride salt form is obtained after purification by flash chromatography (methanol, dichloromethane).

Yield: 4.3 g (92%).

$^1$H NMR (DMSO-d6, ppm): 0.85 (3H); 1.08-1.40 (24H); 1.40-1.52 (2H); 1.71-2.02 (4H); 2.02-2.31 (2H); 2.90-2.98 (2H); 3.15-3.47 (5H); 3.50-3.66 (7H); 4.24 (0.6H); 4.32 (0.4H); 7.83 (0.6H); 7.95 (3H); 8.17 (0.4H).

LC/MS (ESI): 484.6; (calculated ([M+H]$^+$): 484.4).

EXAMPLE AA4: MOLECULE AA4

Molecule A8: Product Obtained by the Reaction Between Molecule A1 and Boc-1-amino-4,7,10-trioxa-13-tridecaneamine.

By a method similar to the one used for the preparation of molecule A2, applied to molecule A1 (4.5 g, 12.7 mmol) and to Boc-1-amino-4,7,10-trioxa-13-tridecaneamine (4.5 g, 14.0 mmol), a yellow oil is obtained after purification by flash chromatography (methanol, dichloromethane).

Yield: 7.7 g (92%).

$^1$H NMR (CDCl$_3$, ppm): 0.88 (3H); 1.22-1.37 (2H); 1.44 (9H); 1.59-1.67 (2H); 1.67-2.00 (6H); 2.06-2.45 (4H); 3.18-3.76 (18H); 4.28 (0.2H); 4.52 (0.8H); 4.69-5.04 (1H); 6.77 (0.2H); 7.20 (0.8H).

Molecule AA4

By a method similar to the one used for the preparation of molecule AA1, applied to molecule A5 (7.7 g, 11.8 mmol), a yellow oil is obtained after purification by flash chromatography (methanol, dichloromethane). Coevaporation with diisopropyl ether makes it possible to obtain the molecule AA4 in hydrochloride salt form in the form of a white solid which is dried under a vacuum at 50° C.

Yield: 5.4 g (76%).

$^1$H NMR (CDCl$_3$, ppm): 0.88 (3H); 1.08-1.40 (24H); 1.49-1.65 (2H); 1.76-2.39 (10H); 3.07-3.28 (3H); 3.34-3.80 (15H); 4.34 (0.05H); 4.64 (0.95H); 7.35 (0.05H); 7.66-8.58 (3.95H).

LC/MS (ESI): 556.7; (calculated ([M+H]$^+$): 556.5).

EXAMPLE AA5: MOLECULE AA5

Molecule A9: Product Obtained by Reaction Between Molecule A1 and N-Boc-L-lysine methyl ester.

By a method similar to the one used for the preparation of molecule A2, applied to molecule A1 (4 g, 11.3 mmol) and to N-Boc-L-lysine methyl ester (3.2 g, 12.4 mmol), a colorless oil is obtained after purification by flash chromatography (methanol, dichloromethane).

Yield: 4.9 g (73%).

$^1$H NMR (CDCl$_3$, ppm): 0.88 (3H); 0.99-1.54 (37H); 1.54-1.75 (3H); 1.75-2.04 (3H); 2.04-2.41 (4H); 2.94-3.19 (2H); 3.19-3.81 (5H); 4.28-4.64 (2H); 4.94 (1H); 6.45 (0.1H); 7.36 (0.9H).

LC/MS (ESI): 596.7; (calculated ([M+H]$^+$): 596.5).

Molecule A10: Product Obtained by Treatment of Molecule A9 with Ammonia.

320 mL of a 7N ammonia solution in methanol are added to a suspension of molecule A9 (4.9 g, 8.2 mmol) in 10 mL of methanol. After 19 h of stirring at room temperature in closed atmosphere, an additional 100 mL of ammonia solution are added. After 24 h of stirring at room temperature in closed atmosphere, the reaction medium is concentrated at reduced pressure. The residue is purified by trituration in diisopropyl ether at reflux (100 mL) to yield a white solid which is dried under a vacuum at 50° C.

Yield: 4.1 g (85%).

$^1$H NMR (CDCl$_3$, ppm): 0.88 (3H); 1.06-1.57 (37H); 1.57-1.79 (3H); 1.88-2.41 (7H); 3.09 (2H); 3.49 (1H); 3.62 (1H); 4.34 (1H); 4.51 (1H); 4.69-4.81 (1H); 5.43 (0.95H); 5.57 (0.05H); 6.25 (0.05H); 6.52 (0.95H); 6.83 (0.05H); 7.11 (0.95H).

Molecule AA5

By a method similar to the one used for the preparation of molecule AA1, applied to molecule A10 (388 mg, 0.67 mmol), a white solid of molecule AA5 in hydrochloride salt form is obtained after purification by triturateion in diisopropyl ether.

Yield: 292 mg (85%).

$^1$H NMR (DMSO-d6, ppm): 0.85 (3H); 1.06-2.34 (38H); 2.61-2.81 (2H); 3.29-3.68 (21H); 4.05-4.17 (1.7H); 4.42 (0.3H); 7.00 (1H); 7.16 (0.7H); 7.43 (0.3H); 7.73-8.04 (3.7H); 8.16 (0.3H).

LC/MS (ESI): 481.6; (calculated ([M+H]$^+$): 481.4).

EXAMPLE AA6: MOLECULE AA6

Molecule A11: Product Obtained by the Reaction Between Stearoyl Chloride and L-proline.

By a method similar to the one used for the preparation of molecule A1, applied to L-proline (5.0 g, 43.4 mmol) and to stearoyl chloride (12.0 g, 39.6 mmol), a white solid is obtained after purification by flash chromatography (methanol, dichloromethane).

Yield: 5.37 g (36%)

$^1$H NMR (CDCl$_3$, ppm): 0.88 (3H); 1.26-1.37 (28H); 1.64-1.70 (2H); 1.88-2.10 (3H); 2.36 (2H); 2.54-2.58 (1H); 3.46 (1H); 3.56 (1H); 4.62 (1H).

LC/MS (ESI): 382.6; (calculated ([M+H]$^+$): 382.3).

Molecule A12: Product Obtained by Reaction Between Molecule A11 and Boc-tri(ethyleneglycol)diamine.

By a method similar to the one used for the preparation of molecule A6, applied to molecule A11 (33.81 g, 88.6 mmol) and to Boc-tri(ethylene glycol)diamine (26.4 g, 106.3 mmol) in THF using DIPEA instead of TEA, a white solid is obtained after purification by flash chromatography (ethyl acetate, methanol).

Yield: 43.3 g (80%)

$^1$H NMR (CDCl$_3$, ppm): 0.87 (3H); 1.24 (30H); 1.43 (9H); 1.61 (2H); 1.82 (1H); 1.96 (1H); 2.25-2.45 (2H); 3.25-3.65 (14H); 4.30 (0.15H); 4.53 (0.85H); 5.25 (1H); 6.43 (0.15H); 7.25 (0.85H).

LC/MS (ESI): 612.6; (calculated ([M+H]$^+$): 612.9).

Molecule AA6

By a method similar to the one used for the preparation of molecule AA2, applied to molecule A12 (43 g, 70.3 mmol), the residue obtained after concentration under a vacuum is triturated in acetonitrile. The suspension is filtered, and the solid is washed with acetonitrile, then acetone. After drying under a vacuum, a white solid of molecule AA6 in hydrochloride salt form is obtained.

Yield: 31.2 g (81%)

$^1$H NMR (DMSO-d$_6$, ppm): 0.85 (3H); 1.23 (28H); 1.45 (2H); 1.70-2.05 (4H); 2.13 (1H); 2.24 (1H); 2.95 (2H); 3.10-3.25 (2H); 3.30-3.65 (10H); 4.20-4.45 (1H); 7.85-8.25 (4H).

LC/MS (ESI): 512.4; (calculated ([M+H]$^+$): 512.8).

EXAMPLE AA7: MOLECULE AA7

Molecule A13: Product Obtained by Reaction Between Arachidonic Acid and L-proline.

By a method similar to the one used for the preparation of molecule A5, applied to arachidonic acid (15.51 g, 49.63 mmol) and to L-proline (6 g, 52.11 mmol) using DIPEA instead of TEA, a white solid is obtained after purification by column chromatography on silica gel (cyclohexane, ethyl acetate, acetic acid).

Yield: 12.9 g (63%)

$^1$H NMR (CDCl$_3$, ppm): 0.88 (3H); 1.28 (34H); 1.66 (2H); 1.95-2.15 (2H); 2.34 (2H); 2.45 (1H); 3.47 (1H); 3.56 (1H); 4.60 (1H).

LC/MS (ESI): 410.4; (calculated ([M+H]$^+$): 410.6).

Molecule A14: Product Obtained by the Reaction Between Molecule A13 and Boc-1-amino-4,7,10-trioxa-13-tridecane.

By a method similar to the one used for the preparation of molecule A12, applied to molecule A13 (10.96 g, 26.75 mmol) and to Boc-1-amino-4,7,10-trioxa-13-tridecane (10.29 g, 32.11 mmol), a solid is obtained after purification by column chromatography on silica gel (cyclohexane, ethyl acetate, methanol).

Yield: 14.2 g (75%)

$^1$H NMR (CDCl$_3$, ppm): 0.88 (3H); 1.24 (32H); 1.43 (9H); 1.57-2.00 (8H); 2.10-2.45 (4H); 3.20-3.75 (18H); 4.30 (0.20H); 4.55 (0.80H); 5.03 (1H); 6.75 (0.20H); 7.20 (0.80H).

LC/MS (ESI): 712.8; (calculated ([M+H]$^+$): 713.1).

Molecule AA7

After a method similar to the one used for the preparation of molecule AA2, applied to molecule A14 (14.25 g, 20.01 mmol), the residue obtained after concentration under a vacuum of the reaction medium is dissolved in methanol and evaporated at reduced pressure, the operation being repeated 4 times to yield a white solid of molecule AA7 in hydrochloride salt form.

Yield: 12.7 g (98%)

$^1$H NMR (DMSO-d$_6$, ppm): 0.85 (3H); 1.23 (32H); 1.45 (2H); 1.64 (2H); 1.70-2.05 (6H); 2.10-2.30 (2H); 2.82 (2H); 3.08 (2H); 3.30-3.60 (14H); 4.15-4.30 (1H); 7.73-8.13 (4H).

LC/MS (ESI): 612.7; (calculated ([M+H]$^+$): 612.9).

EXAMPLE AA8: MOLECULE AA8

Molecule A15: Product Obtained by the Reaction Between L-leucine and palmitoyl chloride.

By a method similar to the one used for the preparation of molecule A1, applied to L-leucine (15.0 g, 114.4 mmol) and to palmitoyl chloride (34.5 g, 125 mmol), a white solid is obtained by trituration in diisopropyl ether.

Yield: 13.0 g (31%)

$^1$H NMR (CDCl$_3$, ppm): 0.88 (3H); 0.96 (6H); 1.16-1.35 (24H); 1.55-1.77 (5H); 2.23 (2H); 4.55-4.60 (1H); 5.88 (1H).

Molecule A6: Product Obtained by the Reaction Between Molecule A15 and L-proline methyl ester By a method similar to the one used for the preparation of molecule A2, applied to molecule A15 (6.00 g, 16.2 mmol) and to L-proline methyl ester (3.23 g, 19.5 mmol), a slightly yellow oil is obtained after purification by flash chromatography (methanol, dichloromethane).

Yield: 5.8 g (74%)

$^1$H NMR (CDCl$_3$, ppm): 0.83-1.00 (9H); 1.18-1.32 (24H); 1.40-1.73 (5H); 1.84-2.33 (6H); 3.47-3.89 (2H); 3.70 (1.14H); 3.71 (1.21H); 3.74 (0.53H); 3.76 (0.12H); 4.40-4.56 (1H); 4.63-4.67 (0.04H); 4.84 (0.38); 4.90 (0.40); 5.06 (0.18); 5.99 (0.18H); 6.08-6.21 (0.82).

LC/MS (ESI): 481.6; (calculated ([M+H]$^+$): 481.4).

Molecule a 17: Product Obtained by Saponification of the Methyl Ester of Molecule A16.

1N sodium hydroxide (13.5 mL, 13.5 mmol) is added to a solution of molecule A16 (5.8 g, 12.06 mmol) in 30 mL of methanol. After 20 h of stirring at room temperature, the solution is diluted with water, then acidified with 20 mL of 1 N hydrochloric acid at 0° C. The precipitate is filtered, then rinsed with water (50 mL), before it being solubilized in 50 mL of dichloromethane. The organic phase is dried over Na$_2$SO$_4$, filtered, then concentrated at reduced pressure to yield a colorless oil.

Yield: 4.5 g (80%)

$^1$H NMR (CDCl$_3$, ppm): 0.85-0.99 (9H); 1.14-1.41 (2414); 1.43-1.72 (5H); 1.87-2.47 (7H); 3.48-3.55 (0.6H); 3.56-3.62 (0.41H); 3.83-3.90 (0.4H); 3.90-3.96 (0.6H); 4.52-4.56 (0.6H); 4.56-4.59 (0.41H); 4.80-4.86 (0.4H); 4.86-4.91 (0.6H); 6.05 (0.4H); 6.11 (0.6H).

LC/MS (ESI): 467.6; (calculated ([M+H]$^+$): 467.4).

Molecule A18: Product Obtained by the Reaction Between Boc-ethylenediamine and Molecule A17.

By a method similar to the one used for the preparation of molecule A2, applied to molecule A17 (4.5 g, 9.64 mmol) and to Boc-ethylenediamine (1.70 g, 10.61 mmol), a colorless oil is obtained after purification by flash chromatography (methanol, dichloromethane).

Yield: 2.0 g (34%)

$^1$H NMR (CDCl$_3$, ppm): 0.83-0.99 (9H); 1.19-1.32 (24H); 1.44 (9H); 1.48-2.37 (14H); 3.09-3.99 (4H); 4.28-5.01 (2H); 5.64-6.04 (1H); 6.87-7.06 (1H).

LC/MS (ESI): 609.7; (calculated ([M+H]$^+$): 609.5).

Molecule AA8

By a method similar to the one used for the preparation of molecule AA1, applied to molecule A18 (2 g, 3.28 mmol), a solid of molecule AA8 in hydrochloride salt form is obtained after purification by flash chromatography (methanol, dichloromethane).

Yield: 1.5 g (90%)

$^1$H NMR (CDCl$_3$, ppm): 0.83-1.00 (9H); 1.18-1.32 (24H); 1.37-1.77 (5H); 1.93-2.41 (6H); 3.07-3.97 (6H); 4.44-4.77 (2H); 7.66-8.21 (2H).

LC/MS (ESI): 509.6; (calculated ([M+H]$^+$): 509.4).

EXAMPLE AA9: MOLECULE AA9

Molecule A19: Product Obtained by the Reaction Between Lauric Acid and L-phenylalanine.

By a method similar to the one used for the preparation of molecule A5, applied to lauric acid (8.10 g, 40.45 mmol) and to L-phenylalanine (7 g, 42.38 mmol), a white solid is obtained.

Yield: 12.7 g (98%)

$^1$H NMR (DMSO-d$_6$, ppm): 0.86 (3H); 1.10-1.30 (16H); 1.36 (2H); 2.02 (2H); 2.82 (1H); 3.05 (1H); 4.42 (1H); 7.15-7.30 (5H); 8.05 (1H); 12.61 (1H).

LC/MS (ESI): 348.2; (calculated ([M+H]$^+$): 348.5).

Molecule A20: Product Obtained by the Reaction Between Molecule A19 and the Hydrochloride Salt of the Methyl Ester of L-proline.

By a method similar to the one used for the preparation of molecule A6, applied to molecule A19 (9.98 g, 28.72 mmol) and to the hydrochloride salt of the methyl ester of L-proline (5.23 g, 31.59 mmol), a colorless oil is obtained after purification by column chromatography on silica gel (cyclohexane, ethyl acetate).

Yield: 5.75 g (44%)

$^1$H NMR (CDCl$_3$, ppm): 0.88 (3H); 1.10-1.30 (16H); 1.50-1.75 (3H); 1.80-2.02 (3H); 2.17 (2H); 2.65 (0.5H); 2.95 (1K); 3.05-3.20 (1.5H); 3.50-3.65 (1H); 3.75 (3H); 4.29 (0.5H); 4.46 (0.5H); 4.70 (0.1H); 4.95 (0.9H); 6.20-6.30 (1H); 7.15-7.30 (5H).

LC/MS (ESI): 459.2; (calculated ([M+H]$^+$): 459.6).

Molecule A21: Product Obtained by Saponification of Molecule A20.

Lithium hydroxide (LiOH) (600.49 mg, 25.07 mmol) is added to a solution of molecule A20 (5.75 g, 12.54 mmol) in a mixture of THF/methanol/water (40/40/40 mL) at 0° C., then the mixture is stirred at room temperature for 20 h. After evaporation of the organic solvents in a vacuum, the aqueous phase is diluted in water, acidified with a 1 N aqueous HCl solution until the pH is 1. The product is then extracted with ethyl acetate. The combined organic phases are washed with a saturated aqueous NaCl solution, dried over Na$_2$SO$_4$, filtered and concentrated at reduced pressure to yield a colorless oil.

Yield: 5.7 g (quantitative)

$^1$H NMR (CDCl$_3$, ppm): 0.88 (3H); 1.10-1.30 (16H); 1.50-1.80 (3H); 1.67-2.02 (2H); 2.20 (2H); 2.25 (0.4H); 2.60 (0.6H); 2.85-3.10 (2.6H); 3.55-3.65 (1.4H); 4.35 (0.6H); 4.55 (0.4H); 4.94 (1H); 6.28 (0.4H); 6.38 (0.6H); 7.20-7.30 (51H).

LC/MS (ESI): 445.2; (calculated ([M+H]$^+$): 445.6).

Molecule A22: Product Obtained by Reaction Between Boc-ethylenediamine and Molecule A21.

By a method similar to the one used for the preparation of molecule A6, applied to molecule A21 (5.67 g, 12.75 mmol) and to Boc-ethylenediamine (2.25 g, 14.03 mmol), a colorless oil is obtained after purification by column chromatography on silica gel (dichloromethane, methanol).

Yield: 5.7 g (76%)

$^1$H NMR (CDCl$_3$, ppm): 0.88 (3H); 1.25 (16H); 1.43 (9H); 1.58 (2.6H); 1.75-1.95 (1.4H); 2.15-2.30 (3H); 2.64 (0.5H); 2.95-3.10 (2.5H); 3.20-3.40 (4H); 3.45 (0.5H); 3.55 (0.2H); 3.66 (1H); 4.44 (1H); 4.50 (0.2H); 4.60 (0.6H); 4.99 (0.7H); 5.54 (0.5H); 5.95 (0.2H); 6.17 (1H); 6.60 (0.5H); 7.07 (0.5H); 7.20-7.40 (5H).

LC/MS (ESI): 587.4; (calculated ([M+H]$^+$): 587.8).

Molecule AA9

After a method similar to the one used for the preparation of molecule AA2, applied to molecule A22 (5.66 g, 9.65 mmol), the residue obtained after concentration under a vacuum of the reaction medium is dissolved in methanol and evaporated at reduced pressure, the operation being repeated 4 times to yield a white foam of molecule AA9 in hydrochloride salt form.

Yield: 4.9 g (97%)

$^1$H NMR (DMSO-d$_6$, 120° C., ppm): 0.89 (3H); 1.26 (16H); 1.43 (2H); 1.68 (0.6H); 1.75-2.00 (3H); 2.05-2.25 (2.4H); 2.82-3.05 (5H); 3.38 (2H); 3.50-3.70 (1.4H); 4.25 (0.6H); 4.63 (0.4H); 4.77 (0.6H); 7.25-7.50 (5H); 7.55-8.20 (4H).

LC/MS (ESI): 487.4; (calculated ([M+H]$^+$): 487.7).

EXAMPLE AA10: MOLECULE AA10

Molecule A23: Product Obtained by the Reaction Between Nipecotic Acid and Arachidonic Acid By a method similar to the one used for the preparation of molecule A5, applied to arachidonic acid (2.30 g, 7.37 mmol) and to nipecotic acid (1.00 g, 7.74 mmol), a white solid is obtained after filtration of the aqueous phase acidified until the pH is 1, and washing of the solid with water, then dichloromethane.

Yield: 1.65 g (53%)

1H NMR (CDCl$_3$, ppm): 0.88 (3H); 1.07-1.88 (37H); 2.10 (1H); 2.28-2.45 (2H); 2.52 (1H); 2.91-3.17 (1.5H); 3.42 (0.5H); 3.72 (0.5H); 3.84 (0.5H); 4.08 (0.5H); 4.56 (0.5H).

LC/MS (ESI): 424.4; 848.0; (calculated ([M+H]$^+$): 424.4; ([2M+H]$^+$): 847.8).

Molecule A24: Product Obtained by the Reaction Between Molecule A23 and Boc-1-amino-4,7,10-trioxa-13-tridecaneamine.

DIPEA (1.01 g, 7.79 mmol) and TBTU (1.31 g, 4.09 mmol) are added successively and at room temperature to a suspension of molecule A23 (1.65 g, 3.89 mmol) in 20 mL of THF. After 30 minutes of stirring, Boc-1-amino-4,7,10-trioxa-13-tridecaneamine (1.37 g, 4.28 mmol) is added, and the reaction medium is stirred at room temperature for 18 h. After evaporation of the solvent at reduced pressure, the residue is diluted with ethyl acetate (100 mL), the organic phase is washed successively with a saturated aqueous NaHCO$_3$ solution, a 1 N aqueous HCl solution, a saturated aqueous NaCl solution, dried over Na$_2$SO$_4$, filtered and concentrated at reduced pressure. A white solid is obtained after purification by flash chromatography (cyclohexane, ethyl acetate, methanol).

Yield: 1.97 g (70%)

$^1$H NMR (CDCl$_3$, ppm): 0.88 (3H); 1.15-2.70 (54H); 3.10-3.46 (6H); 3.46-3.71 (12.6H); 3.92 (0.4H); 4.17 (0.6H); 4.49 (0.4H); 4.80-5.16 (1H); 6.35-6.76 (1H).

LC/MS (ESI): 726.8; (calculated ([M+H]$^+$: 726.6).

Molecule AA10

By a method similar to the one used for the preparation of molecule AA1, applied to molecule A24 (1.97 g, 2.71 mmol), a white solid of molecule AA10 is obtained after evaporation of the solvent, trituration in acetone, filtration and washing with acetone, then drying at reduced pressure at 50° C.

Yield: 1.66 g (92%)

$^1$H NMR (DMSO-d$_6$, ppm): 0.86 (3H); 1.09-1.90 (42H); 2.05-2.68 (5H); 2.45-2.68 (1H); 2.78-3.19 (6H); 3.36-3.44 (2H); 3.44-3.60 (10H); 3.69-3.87 (1H); 4.20 (0.4H); 4.35 (0.6H).

LC/MS (ESI): 626.7; (calculated ([M+H]$^+$): 626.5).

EXAMPLE AA12: MOLECULE AA12

Molecule A26: Product Obtained by the Reaction Between Myristoyl Chloride and L-proline Myristoyl chloride (322 g, 1.30 mol) in solution in dichloromethane (1.63 L) is added slowly within 1 h to a solution of L-proline (300.40 g, 2.61 mol) in 2 N aqueous sodium hydroxide (1.63 L) at 0° C. At the end of the addition, the temperature of the reaction medium is brought back to 20° C. within 2 h, then stirred for an additional 2 h. The mixture is cooled to 0° C., then a 37% HCl solution (215 mL) is added within 15 minutes. The reaction medium is stirred for 10 min at 0° C., then for 1 h from 0° C. to 20° C. The organic phase is separated, washed with a 10% HCl solution (3×430 mL), a saturated aqueous NaCl solution (430 mL), dried over $Na_2SO_4$, filtered through cotton, then concentrated at reduced pressure. The residue is solubilized in heptane (315 mL), then pentane (1.6 L) is added under mechanical stirring. A white solid is obtained after filtration through a sintered filter and drying at reduced pressure.

Yield: 410.6 g (97%)

$^1$H NMR ($CDCl_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7; (calculated ($[M+H]^+$): 326.3; ($[2M+H]^+$): 651.6).

Molecule A27: Product Obtained by the Reaction Between Molecule A26 and Boc-ethylenediamine.

HOBt (1.83 g, 11.98 mmol), then Boc-ethylenediamine (1.62 g, 10.14 mmol) are added successively to a solution of molecule A26 (3.00 g, 9.21 mmol) at room temperature in methyl-THF (50 mL), and the medium is cooled to 0° C. EDC (2.29 g, 11.98 mmol) is added, then the mixture is stirred for 17 h between 0° C. and room temperature. The reaction medium is then washed with a saturated aqueous $NH_4Cl$ solution (50 mL), a saturated aqueous $NaHCO_3$ solution (50 mL), then a saturated aqueous NaCl solution (50 mL), dried over $Na_2SO_4$, filtered and concentrated at reduced pressure. A white solid is obtained after recrystallization in methanol.

Yield: 2.34 g (49%).

$^1$H NMR ($CDCl_3$, ppm): 0.88 (3H); 1.16-1.38 (20H); 1.44 (9H); 1.56-1.71 (2H); 1.78-2.45 (6H); 3.11-3.72 (6H); 4.30 (0.1H); 4.51 (0.9H); 4.87 (0.1H); 5.04 (0.9H); 6.87 (0.1H); 7.23 (0.9H).

LC/MS (ESI): 468.0; (calculated ($[M+H]^+$): 468.4).

Molecule AA12

By a method similar to the one used for the preparation of molecule AA1, applied to molecule A27 (2.34 g, 5.00 mmol), a white solid of molecule AA12 is obtained after evaporation of the solvent and triturations in diisopropyl ether.

Yield: 1.5 g (74%)

$^1$H NMR (MeOD-d4, ppm): 0.90 (3H); 1.21-1.43 (20H); 1.54-1.66 (2H); 1.85-2.28 (4H); 2.39 (2H); 3.00-3.17 (2H); 3.30-3.40 (1H); 3.43-3.71 (3H); 4.29 (0.94H); 4.48 (0.06H).

LC/MS (ESI): 368.2; (calculated ($[M+H]^+$): 368.3).

EXAMPLE AA14: MOLECULE AA14

Resin AA14-1: Product Obtained by the Reaction Between 4,7,10-trioxa-1,13-Tridecanediamine and the resin 2-Cl-trityl chloride DIPEA (8.64 mL, 49.60 mmol) is added to a solution of 4,7,10-trioxa-1,13-tridecanediamine (10.87 mL, 49.60 mmol) in dichloromethane (50 mL) at room temperature. This solution is poured onto the resin 2-Cl-trityl chloride which was washed beforehand with dichloromethane (100-200 mesh, 1% DVB, 1.24 mmol/g) (4.00 g, 4.96 mmol) in a reactor adapted for peptide synthesis on a solid support. After 2 h of stirring at room temperature, HPLC grade methanol (0.8 mL/g resin, 3.2 mL) is added, and the mixture is stirred at room temperature for 15 min. The resin is filtered, washed successively with dichloromethane (3×50 mL), DMF (2×50 mL), dichloromethane (2×50 mL), isopropanol (1×50 mL) and dichloromethane (3×50 mL).

Resin AA14-2: Product Obtained by Reaction Between the Resin AA14-1 and Fmoc-glycine.

DIPEA (5.18 mL, 29.76 mmol) is added to a suspension of Fmoc-glycine (4.42 g, 14.88 mmol) and 1-[bis(dimethylamino)methylene]-1H-1,2,3-triazolo[4,5-b]pyridinium 3-oxide-hexafluorophosphate (HATU, 5.66 g, 14.88 mmol) in a mixture of DMF/dichloromethane 1:1 (60 mL). After complete solubilization, the solution obtained is poured onto resin AA14-1. After 2 h of stirring at room temperature, resin is filtered, washed successively with DMF (3×60 mL), isopropanol (1×60 ml) and dichloromethane (3×60 ml).

Resin AA14-3: product obtained by reaction between resin AA14-2 and a mixture of DMF/piperidine 80:20. The resin AA14-2 is treated with a mixture of DMF/piperidine 80:20 (50 mL). After 30 minutes of stirring at room temperature, the resin is filtered, washed successively with DMF (3×50 mL), isopropanol (1×50 mL) and dichloromethane (3×50 mL).

Resin AA14-4: Product Obtained by the Reaction Between Resin AA14-3 and Fmoc-proline.

By a method similar to the one used for resin AA14-2, applied to resin AA14-3 and Fmoc-proline (5.02 g, 14.88 mmol) in DMF (50 mL), resin AA14-4 is obtained.

Resin AA14-5: Product Obtained by Reaction Between Resin AA14-4 and a Mixture of DMF/piperidine 80:20.

By a method similar to the one used for resin AA14-3, applied to resin AA14-4 and a mixture of DMF/piperidine 80:20 (50 mL), resin AA14-5 is obtained.

Resin AA14-6: Product Obtained by Reaction Between Resin AA14-5 and Palmitic Acid.

By a method similar to the one used for the preparation of resin AA14-4, applied to resin AA14-5 and to palmitic acid (3.82 g, 14.88 mmol), resin AA14-6 is obtained.

Molecule AA14

The resin AA14-6 is treated with a mixture of TFA/dichloromethane 1:1 (50 mL). After 30 minutes of stirring at room temperature, the resin is filtered and washed with dichloromethane (3×50 mL). The solvents are evaporated under a vacuum. Two coevaporations are then carried out on the residue with dichloromethane (50 mL), then diisopropyl ether (50 mL). The residue is solubilized in dichloromethane (50 mL), and the organic phase is washed with a 1 N aqueous NaOH solution (1×50 mL), then a saturated NaCl solution (2×50 mL). After drying over Na$_2$SO$_4$, the organic phase is filtered, concentrated under a vacuum, and the residue is filtered by chromatography on silica gel (dichloromethane, methanol, NH$_4$OH).

Yield: 1.65 g (54% global over 7 steps)

$^1$H NMR (CDCl$_3$, ppm): 0.88 (3H); 1.18-2.39 (38H); 2.79 (2H); 3.23-3.44 (2H); 3.47-3.69 (14H); 3.76 (0.92H); 3.82 (0.08H); 3.98 (0.08H); 4.03 (0.92H); 4.34 (0.08H); 4.39 (0.92H); 7.00-7.40 (2H).

LC/MS (ESI): 613.7; (calculated ([M+H]$^+$): 613.5).

AB: Synthesis of the co-polyamino acids

TABLE 1b

| No. | co-polyamino acids bearing carboxylates charges and hydrophobic radicals |
|---|---|
| AB1 | 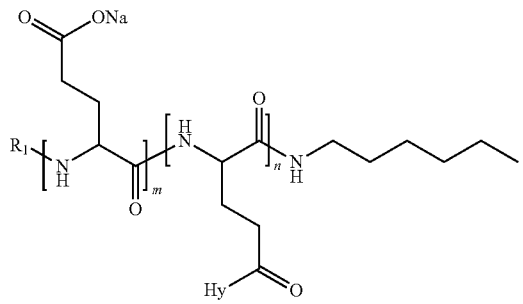<br>i = 0.05, DP (m + n) = 23<br>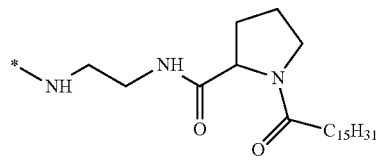<br>Hy =<br>R$_1$ = H or pyroglutamate |
| AB2 | 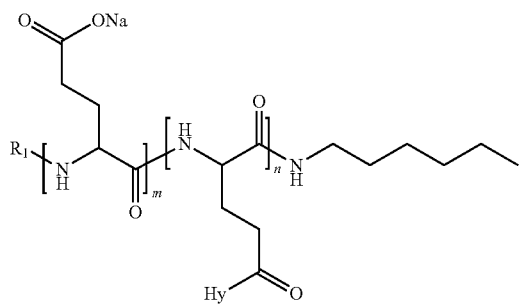<br>i = 0.05, DP (m + n) = 35<br>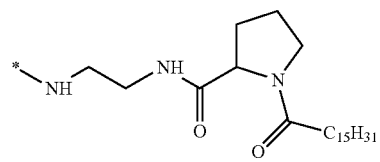<br>Hy =<br>R$_1$ = H or pyroglutamate |

TABLE 1b-continued
| No. | co-polyamino acids bearing carboxylates charges and hydrophobic radicals |
|---|---|
| AB3 | 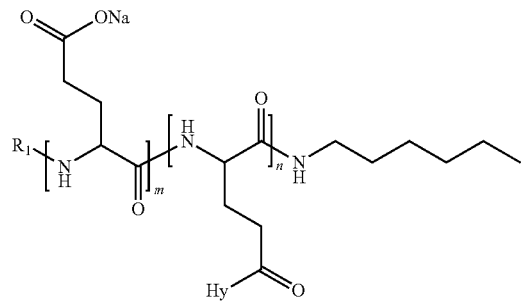
i = 0.10, DP (m + n) = 35
Hy = 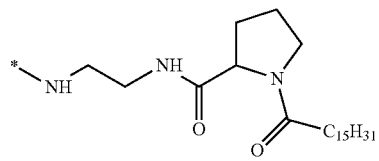
$R_1$ = H or pyroglutamate |
| AB4 | 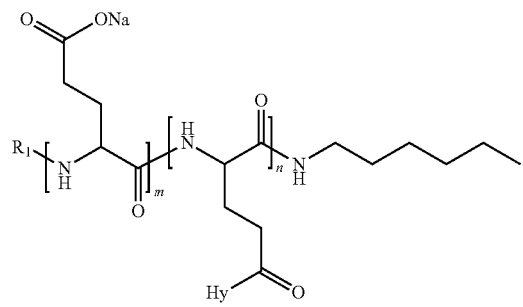
i = 0.052, DP (m + n) = 23
Hy = 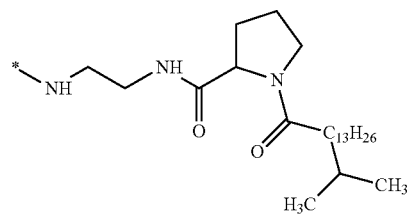
$R_1$ = H or pyroglutamate |

TABLE 1b-continued
| No. | co-polyamino acids bearing carboxylates charges and hydrophobic radicals |
|---|---|
| AB5 | 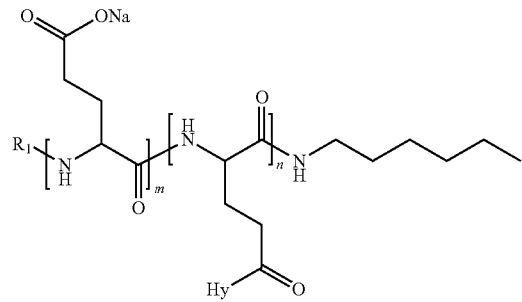
i = 0.05, DP (m + n) = 23
Hy =
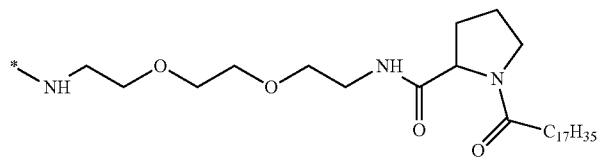
$R_1$ = H or pyroglutamate |
| AB6 | 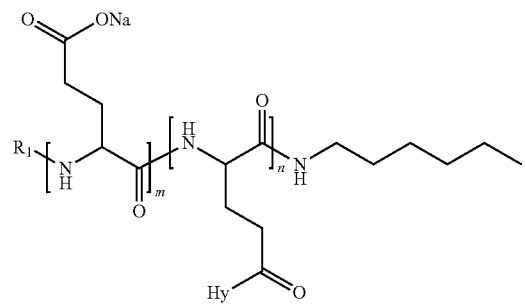
i = 0.025, DP (m + n) = 20
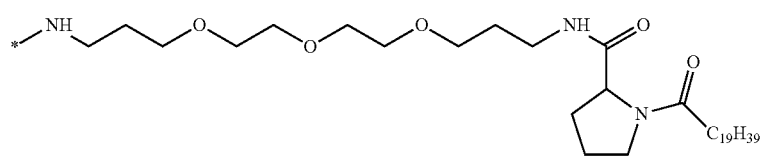
$R_i$ = H or pyroglutamate |

TABLE 1b-continued

| No. | co-polyamino acids bearing carboxylates charges and hydrophobic radicals |
|---|---|
| AB7 | $i = 0.03$, DP $(m + n) = 21$ <br> Hy = <br> $R_i = CH_3-CO-$, H or pyroglutamate |
| AB8 | $i = 0.03$, DP $(m + n) = 24$ <br> Hy = <br> $R_1 = $ H or pyroglutamate |

TABLE 1b-continued
| No. | co-polyamino acids bearing carboxylates charges and hydrophobic radicals |
|---|---|
| AB9 | 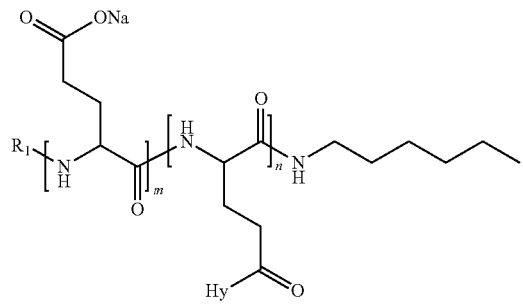<br>i = 0.12, DP (m + n) = 30<br><br>Hy =<br>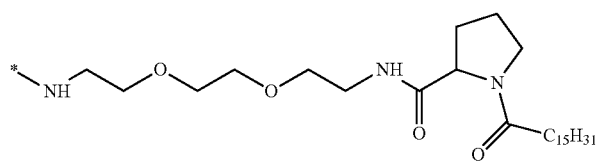<br>$R_1$ = H or pyroglutamate |
| AB10 | 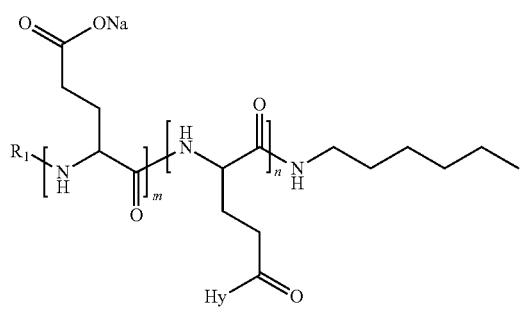<br>i = 0.08, DP (m + n) = 25<br>Hy =<br>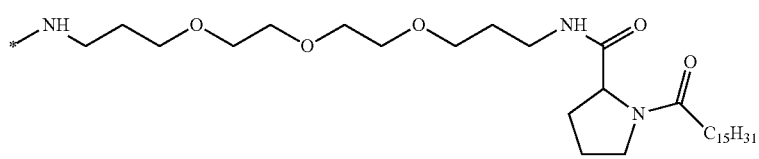<br>$R_1$ = H or pyroglutamate |

TABLE 1b-continued
| No. | co-polyamino acids bearing carboxylates charges and hydrophobic radicals |
|---|---|
| AB11 | 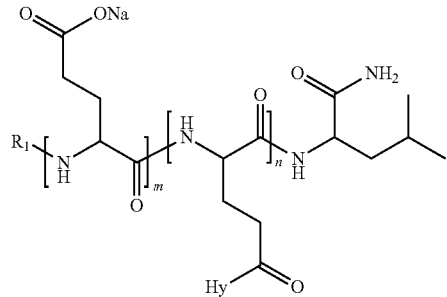
i = 0.05, DP (m + n) = 23
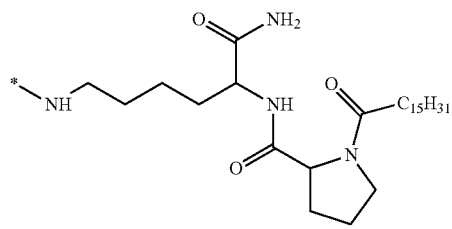
Hy =
$R_1$ = H or pyroglutamate |
| AB12 | 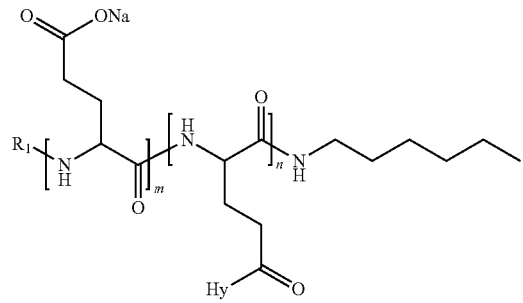
i = 0.04, DP (m + n) = 26
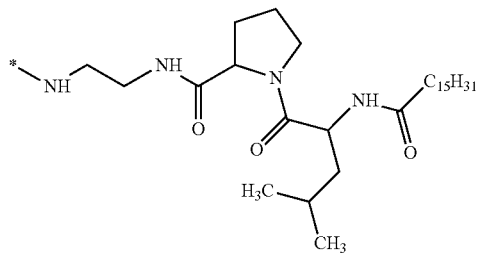
Hy =
$R_1$ = H or pyroglutamate |

TABLE 1b-continued
| No. | co-polyamino acids bearing carboxylates charges and hydrophobic radicals |
|---|---|
| AB13 | 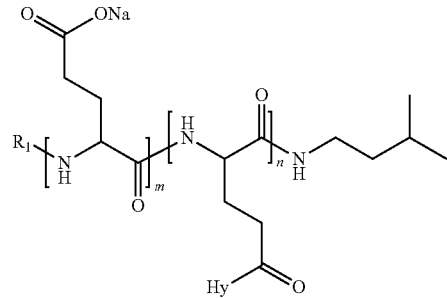 i = 0.12, DP (m + n) = 35<br><br>Hy = 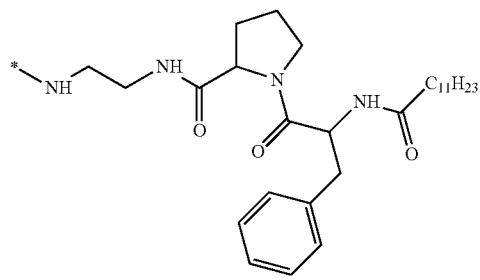<br>$R_1$ = H or pyroglutamate |
| AB21 | 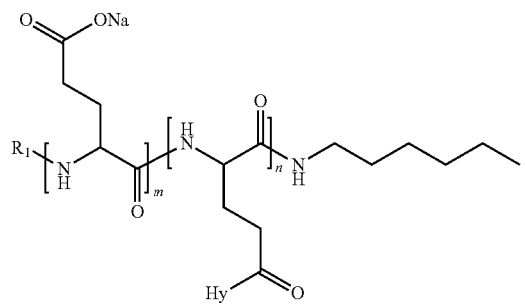 i = 0.056, DP (m + n) = 22<br><br>Hy = 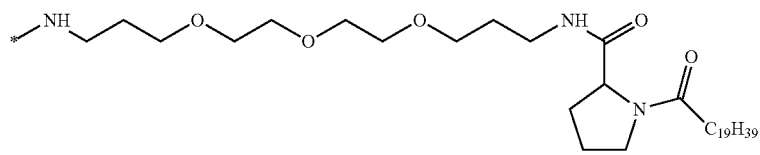<br>$R_1$ = H or pyroglutamate |

TABLE 1b-continued
| No. | co-polyamino acids bearing carboxylates charges and hydrophobic radicals |
|---|---|
| AB24 | 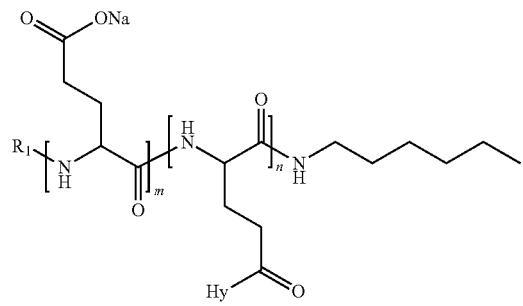 i = 0.089, DP (m + n) = 38<br><br>Hy =<br><br>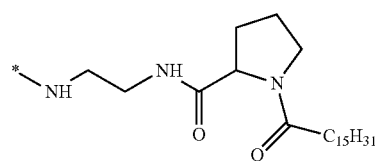<br><br>$R_1$ = $CH_3$—CO—, H or pyroglutamate |
| AB25 | 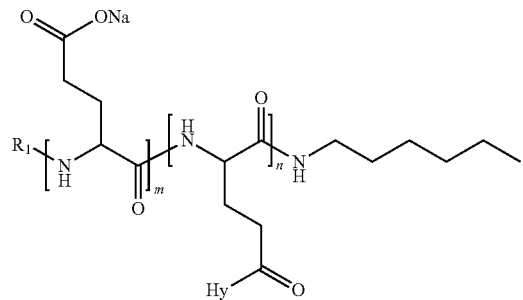 i = 0.16, DP (m + n) = 38<br><br>Hy =<br><br>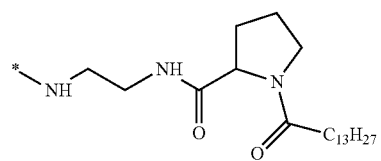<br><br>$R_1$ = $CH_3$—CO—, H or pyroglutamate |

TABLE 1b-continued

| No. | co-polyamino acids bearing carboxylates charges and hydrophobic radicals |
|---|---|
| AB28 | (structure shown) | i = 0.1, DP (m + n) = 38

Hy = (structure shown)

$R_1$ = $CH_3$—CO—, H or pyroglutamate

Part AB: Synthesis of the Co-Polyamino Acids

EXAMPLE AB1: CO-POLYAMINO ACID AB1—SODIUM POLY-L-GLUTAMATE MODIFIED BY MOLECULE AA1 AND HAVING A NUMBER AVERAGE MOLECULAR WEIGHT (MN) OF 2900 G/MOL

Co-Polyamino Acid AB1-1:

poly-L-glutamic acid having a relative number average molecular weight (Mn) of 3861 g/mol originating from the polymerization of the γ-benzyl-L-glutamate N-carboxyanhydride initiated by hexylamine.

γ-Benzyl-L-glutamate N-carboxyanhydride (89.9 g, 341 mmol) is placed under a vacuum for 30 minutes in a round-bottom flask dried in the oven, then anhydrous DMF (200 mL) is introduced. The mixture is then stirred under argon until the dissolution is complete, cooled to 4° C., then hexylamine (2.05 mL; 15.5 mmol) is introduced rapidly. The mixture is stirred between 4° C. and room temperature for 2 days. The reaction mixture is then heated at 65° C. for 2 h, cooled at room temperature, then poured dropwise into diisopropyl ether (3 L) under stirring. The white precipitate is recovered by filtration, washed with diisopropyl ether (2×200 mL), then dried under a vacuum at 30° C. to yield a poly(gamma-benzyl-L-glutamic) acid (BBLG).

Trifluoroacetic acid (TFA, 340 mL) at 4° C., a 33% hydrobromic acid solution (HBr) in acetic acid (240 mL, 1.37 mol) is added dropwise to a solution of PBLG (74.8 g). The mixture is stirred at room temperature for 2 h, then poured dropwise onto a 1:1 (v/v) mixture of diisopropyl ether and water under stirring (4 L). After 2 h of stirring, the heterogeneous mixture is allowed to rest overnight. The white precipitate is recovered by filtration, washed with a 1:1 (v/v) mixture of diisopropyl ether and water (340 mL), then with water (340 mL).

The solid obtained is then solubilized in water (1.5 L) by adjusting the pH to 7 by addition of a 10 N aqueous sodium hydroxide solution, then a 1 N aqueous sodium hydroxide solution. After solubilization, the theoretical concentration is adjusted to 20 g/L theoretical by addition of water to obtain a final volume 2.1 L.

The solution is filtered through a 0.45-μm filter, then purified by ultrafiltration against a 0.9% NaCl solution, then water until the conductimetry of the permeate is less than 50 μS/cm. The solution of co-polyamino acid is the concentrated until a final volume 1.8 L is obtained.

The aqueous solution is then acidified by addition of 37% hydrochloric acid solution until the pH is 2. After 4 h of stirring, the precipitate obtained is filtered, washed with water (2×340 mL), then dried under a vacuum at 30° C. to yield a poly-L-glutamic acid having a number average molecular weight (Mn) of 3861 g/mol with respect to a polyoxyethylene standard (PEG).

Co-Polyamino Acid AB1

The co-polyamino acid AB-1 (10.0 g) is solubilized in DMF (700 mL) at 30° C.-40° C., then cooled to 0° C. Molecule AA1 in hydrochloric salt form (1.64 g, 3.8 mmol) is suspended in DMF (23 mL), and triethylamine (0.39 g, 3.8 mmol) is then added and the mixture is heated slightly under stirring until the dissolution is complete. To the solution of co-polyamino acid at 0° C., N-methylmorpholine (NMM, 7.6 g, 75 mmol) in DMF (14 mL) and ethyl chloroformate (ECF, 8.2 g, 75 mmol) are added. After 10 min at 0° C., the solution containing molecule AA1 is added, and the mixture is maintained at 30° C. for 2 h. The reaction mixture is poured dropwise onto 5.5 L of water containing 15% by weight of sodium chloride and HCl (pH 2), then it is allowed to rest overnight. The precipitate is collected by filtration and dried under a vacuum for approximately 30 min. The white solid obtained is taken up in water (500 mL) and the pH is adjusted to 7 by slow addition of a 1N NaOH aqueous solution. After filtration through a 0.45-μm filter, the clear solution obtained is purified by ultrafiltration against a 0.9% NaCl solution, then water until the conductimetry of the permeate is less than 50 μS/cm. After discharging, the solution is filtered through a 0.2 μm filter and stored at 2-8° C.

Dry extract: 24.9 mg/g

An average degree of polymerization (DP) of 23 is estimated by $^1$H NMR in $D_2O$ by comparing the integration of the signals originating from the hydrophobe grafted onto that of the signals originating from the main chain.

Based on $^1$H NMR: i=0.05

The calculated average molecular weight of the co-polyamino acid AB1 is calculated on the basis of the molecular weights of the radicals $R_1$ and $R_2$, the aspartate and/or glutamate residue(s) (comprising an amide bond), the hydrophobic radical, the DS and the DP.

The calculated average molecular weight of the co-polyamino acid AB1 is 3945 g/mol.

HPLC-aqueous SEC (calibrant PEG): Mn=2900 g/mol.

EXAMPLE AB2: CO-POLYAMINO ACID AB2—SODIUM POLY-L-GLUTAMATE MODIFIED BY MOLECULE AA1 AND HAVING A NUMBER AVERAGE MOLECULAR WEIGHT (MN) OF 3700 G/MOL

By a method similar to the one used for the preparation of the co-polyamino acid AB1, applied to the hydrochloride salt of molecule AA1 (1.64 g, 3.8 mmol) and to a poly-L-glutamic acid having a relative Mn of 5200 g/mol (10.0 g) obtained by a method similar to the one used for the preparation of the co-polyamino acid AB1-1, a sodium poly-L-glutamate modified by molecule AA1 is obtained.

Dry extract: 14.1 mg/g

DP (estimated based on $^1$H NMR): 35

Based on $^1$H NMR: i=0.05

The calculated average molecular weight of the co-polyamino acid AB2 is 5972 g/mol.

HPLC aqueous-SEC (calibrant PEG): Mn=3700 g/mol.

EXAMPLE AB3: CO-POLYAMINO ACID AB3—SODIUM POLY-L-GLUTAMATE MODIFIED BY MOLECULE AA1 AND HAVING A NUMBER AVERAGE MOLECULAR WEIGHT (MN) OF 4900 G/MOL

By a method similar to the one used for the preparation of the co-polyamino acid AB1, applied to the hydrochloride salt of molecule AA1 (3.30 &g, 7.6 mmol) and to a poly-L-glutamic acid having a relative number average weight (Mn) of 5200 g/mol (10.0 g) obtained by a method similar to the one used for the preparation of the co-polyamino acid AB1-1, a sodium poly-L-glutamate modified by molecule AA1 is obtained.

Dry extract: 23.4 mg/g

DP (estimated based on $^1$H NMR): 35

The calculated average molecular weight of the co-polyamino acid AB3 is 6594 g/mol.

Based on $^1$H NMR: i=0.10

HPLC aqueous-SEC (calibrant PEG): Mn=4900 g/mol.

EXAMPLE AB4: CO-POLYAMINO ACID AB4—SODIUM POLY-L-GLUTAMATE MODIFIED BY MOLECULE AA2 AND HAVING A NUMBER AVERAGE MOLECULAR WEIGHT (MN) OF 1800 G/MOL

By a method similar to the one used for the preparation of the co-polyamino acid AB1, applied to the hydrochloride salt of molecule AA2 (1.09 g, 2.4 mmol) and to a poly-L-glutamic acid having an average weight Mn=5600 g/mol (6.3 g) obtained by a method similar to the one used for the preparation of the co-polyamino acid AB1-1 but with a step of deprotection of the benzyl esters using trimethylsilane iodide according to the protocol described in the publication J. Am. Chem. Soc. 2000, 122, 26-34 (Subramanian G. et al.), a sodium poly-L-glutamate modified by molecule AA2 is obtained.

Dry extract: 21.5 mg/g

DP (estimated based on $^1$H NMR): 35

Based on $^1$H NMR: i=0.052

The calculated average molecular weight of the co-polyamino acid AB4 is 6022 g/mol.

HPLC aqueous-SEC (calibrant PEG): Mn=1800 g/mol.

EXAMPLE AB5: CO-POLYAMINO ACID AB5—SODIUM POLY-L-GLUTAMATE MODIFIED BY MOLECULE AA6 AND HAVING A NUMBER AVERAGE MOLECULAR WEIGHT (MN) OF 2600 G/MOL

By a method similar to the one used for the preparation of the co-polyamino acid AB1, applied to the hydrochloride salt of molecule AA6 (2.06 g, 3.8 mmol) and to a poly-L-glutamic acid (9.8 g) obtained by a method similar to the one used for the preparation of the co-polyamino acid AB1-1, a sodium poly-L-glutamate modified by molecule AA6 is obtained.

Dry extract: 20.9 mg/g

DP (estimated based on $^1$H NMR): 23

Based on $^1$H NMR: i=0.05

The calculated average molecular weight of the co-polyamino acid AB5 is 4079 g/mol.

HPLC aqueous-SEC (calibrant PEG): Mn=2600 g/mol.

EXAMPLE AB6: CO-POLYAMINO ACID AB6—SODIUM POLY-L-GLUTAMATE MODIFIED BY MOLECULE AA7 AND HAVING A NUMBER AVERAGE MOLECULAR WEIGHT (MN) OF 4000 G/MOL

A poly-L-glutamic acid having an average weight Mn=3500 g/mol and a degree of polymerization 22 (10.0 g) obtained by a method similar to the one used for the preparation of the co-polyamino acid AB1-1 is solubilized in DMF (420 mL) at 30° C.-40° C., then maintained at this temperature. In parallel, the hydrochloride salt of molecule AA7 (1.47 g, 2.3 mmol) is suspended in DMF (12 mL), and triethylamine (0.23 g, 2.3 mmol) is added, the mixture is then heated slightly under stirring until the dissolution is complete. To the solution of co-polyamino acid in DMF, NMM (7.6 g, 75 mmol), the solution of AA7, then 2-hydroxypyridine N-oxide (HOPO, 0.84 g, 7.5 mmol) are added successively. The reaction mixture is then cooled to 0° C., then EDC (1.44 g, 7.5 mmol) is added and the temperature of the medium is increased to room temperature over a period of 2 h. The reaction medium is filtered through a woven 0.2-mm filter and poured dropwise onto 3.5 L of water containing 15% by weight of NaCl and HCl (pH 2) under stirring. At the end of the addition, the pH is readjusted to 2 with a 37% HCl solution, and the suspension is allowed to rest overnight. The precipitate is collected by filtration, then rinsed with 100 mL of water. The white solid obtained is solubilized in 500 mL of water by slow addition of a 1 N aqueous NaOH solution until the pH is 7 under stirring, then the solution is filtered through a 0.45-μm filter.

The clear solution obtained is purified by ultrafiltration against a 0.9% NaCl solution, then water until the conductimetry of the permeate is less than 50 µS/cm. The solution is filtered through a 0.2-µm filter and stored at 2-8° C.

Dry extract: 21.6 mg/g
DP (estimated based on $^1$H NMR): 20
Based on $^1$H NMR: i=0.025

The calculated average molecular weight of the co-polyamino acid AB6 is 3369 g/mol.

HPLC aqueous-SEC (calibrant PEG): Mn=4000 g/mol.

EXAMPLE AB7: CO-POLYAMINO ACID AB7—SODIUM POLY-L-GLUTAMATE CAPPED AT ONE OF ITS ENDS BY AN ACETYL GROUP AND MODIFIED BY MOLECULE AA7 AND HAVING A NUMBER AVERAGE MOLECULAR WEIGHT (MN) OF 3300 G/MOL

Co-polyamino acid AB7-1: poly-L-glutamic acid having a relative number average molecular weight (Mn) of 3600 g/mol and DP 21, originating from the polymerization of γ-benzyl-L-glutamate N-carboxyanhydride initiated by hexylamine, and capped at one of its ends by an acetyl group.

γ-Benzyl-L-glutamate N-carboxyanhydride (Glu(OBn)-NCA, 100.0 g, 380 mmol) is placed under a vacuum for 30 minutes in a round-bottom flask previously dried in the oven, then anhydrous DMF (225 mL) is introduced. The mixture is then stirred under argon until the dissolution is complete, cooled to 4° C., then hexylamine (1.78 g, 17 mmol) is introduced rapidly. The mixture is stirred between 4° C. and room temperature for 2 days, then precipitated in diisopropyl ether (3.4 L). The precipitate is recovered by filtration, washed two times with diisopropyl ether (225 mL), then dried to yield a white solid which is dissolved in 450 mL of THF. To this solution, DIPEA (31 mL, 176 mmol), then acetic anhydride (17 mL, 176 mmol) are added successively. After a night of stirring at room temperature, the solution is poured slowly into diisopropyl ether (3 L) under stirring. After 1 h of stirring, the precipitate is filtered, washed two times with diisopropyl ether (250 mL), then dried under a vacuum at 30° C. to yield a poly(gamma-benzyl-L-glutamic) acid capped at one of its ends by an acetyl group.

A 33% hydrobromic acid solution (HBr) in acetic acid (235 mL) is added dropwise to a solution of the co-polyamino acid above (72 g) in trifluoroacetic acid (TFA, 335 mL) at 4° C. The mixture is stirred at room temperature for 3 h 30, then poured dropwise onto a 1:1 (v/v) mixture of diisopropyl ether and water under stirring (4 L). After 2 h of stirring, the heterogeneous mixture is allowed to rest overnight. The white precipitate is recovered by filtration, washed with 1:1 (v/v) mixture of diisopropyl ether and water (340 mL), then with water (340 mL.).

The solid obtained is then dissolved in water (1.5 L) by adjusting the pH to 7 by addition of a 10 N aqueous sodium hydroxide solution, then a 1 N aqueous sodium hydroxide solution. After solubilization, the mixture is diluted by addition of water to obtain a final volume of 2.1 L. The solution is filtered through a 0.45-µm filter, then purified by ultrafiltration against a 0.9% NaCl solution, then water until the conductimetry of the permeate is less than 50 µS/cm. The solution of co-polyamino acid is then concentrated until a final volume of 1.8 L is obtained.

The aqueous solution is then acidified by addition of 37% hydrochloric acid solution until the pH is 2. After 4 h of stirring, the precipitate obtained is filtered, washed with water (330 mL), then dried under a vacuum at 30° C. to yield a poly-L-glutamic acid having a number average molecular weight (Mn) of 3600 g/mol with respect to a polyoxyethylene standard (PEG) and an average degree of polymerization of 21.

Co-polyamino acid AB7: By a method similar to the one used for the preparation of the co-polyamino acid AB6, applied to the hydrochloride salt of molecule AA7 (1.43 g, 2.2 mmol) and to the co-polyamino acid AB7-1 (10.0 g), a sodium poly-L-glutamate acid modified by molecule AA7 is obtained.

Dry extract: 24.3 mg/g
DP (estimated based on $^1$H NMR): 21
Based on $^1$H NMR: i=0.03

The calculated average molecular weight of the co-polyamino acid AB7 is 3677 g/mol.

HPLC aqueous-SEC (calibrant PEG): Mn 3300 g/mol.

EXAMPLE AB8: CO-POLYAMINO ACID AB8—SODIUM POLY-L-GLUTAMATE MODIFIED BY MOLECULE AA7 AND HAVING A NUMBER AVERAGE MOLECULAR WEIGHT (MN) OF 3600 G/MOL

Co-Polyamino Acid AB8-1:

poly-L-glutamic acid having a number average molecular weight (Mn) of 3800 g/mol and a degree of polymerization of 24, originating from the polymerization of γ-benzyl-L-glutamate N-carboxyanhydride initiated by ammonia.

By a method similar to the one described in the French patent FR-A-2 801 226, applied to γ-methyl-L-glutamic acid N-carboxyanhydride (25.0 g, 133.6 mmol) and to a 0.5 N ammonia solution in dioxane (12.1 mL, 6.05 mmol), a poly-L-glutamic acid is obtained.

Co-Polyamino Acid AB8:

By a method similar to the one used for the preparation of the co-polyamino acid AB6, applied to the hydrochloride salt of molecule AA7 (2.1 g, 3.24 mmol) and to the co-polyamino acid AB8-1 (14.3 g), a sodium poly-L-glutamate modified by molecule AA7 is obtained.

Dry extract: 25.2 mg/g
DP (estimated based on $^1$H NMR): 24
Based on $^1$H NMR: i=0.03

The calculated average molecular weight of the co-polyamino acid AB8 is 4099 g/mol.

HPLC aqueous-SEC (calibrant PEG): Mn=3600 g/mol.

EXAMPLE AB9: CO-POLYAMINO ACID AB9—SODIUM POLY-L-GLUTAMATE MODIFIED BY MOLECULE AA3 AND HAVING A NUMBER AVERAGE MOLECULAR WEIGHT (MN) OF 3200 G/MOL

By a method similar to the one used for the preparation of the co-polyamino acid AB1, applied to the hydrochloride salt of molecule AA3 and to a poly-L-glutamic acid obtained by a method similar to the one used for the preparation of the co-polyamino acid AB1-1, a sodium poly-L-glutamate modified by molecule AA3 is obtained.

Dry extract: 14.7 mg/g
DP (estimated based on $^1$H NMR): 30
Based on $^1$H NMR: i=0.12

The calculated average molecular weight of the co-polyamino acid AB9 is 6192 g/mol.

HPLC aqueous-SEC (calibrant PEG): Mn=3200 g/mol.

EXAMPLE AB10: CO-POLYAMINO ACID AB10—SODIUM POLY-L-GLUTAMATE MODIFIED BY MOLECULE AA4 AND HAVING A NUMBER AVERAGE MOLECULAR WEIGHT (MN) OF 2600 G/MOL

By a method similar to the one used for the preparation of the co-polyamino acid AB7, applied to the hydrochloride salt of molecule AA4 and to a poly-L-glutamic acid obtained by a method similar to the one used for the preparation of the co-polyamino acid AB1-1, a sodium poly-L-glutamate modified by molecule AA4 is obtained.

Dry extract: 18.3 mg/g
DP (estimated based on $^1$H NMR): 25
Based on $^1$H NMR: i=0.08
The calculated average molecular weight of the co-polyamino acid AB10 is 4870 g/mol.
HPLC aqueous-SEC (calibrant PEG): Mn=2600 g/mol.

EXAMPLE AB11: CO-POLYAMINO ACID AB11—SODIUM POLY-L-GLUTAMATE MODIFIED BY MOLECULE AA5 AND HAVING A NUMBER AVERAGE MOLECULAR WEIGHT (MN) OF 2700 G/MOL

By a method similar to the one used for the preparation of the co-polyamino acid AB6, applied to the hydrochloride salt of molecule AA5 and to a poly-L-glutamic acid obtained by a method similar to the one used for the preparation of the co-polyamino acid AB1-1, a sodium poly-L-glutamate modified by molecule AA5 is obtained.

Dry extract: 20.2 mg/g
DP (estimated based on $^1$H NMR): 23
Based on $^1$H NMR: i=0.05
The calculated average molecular weight of the co-polyamino acid AB11 is 4072 g/mol.
HPLC aqueous-SEC (calibrant PEG): Mn=2700 g/mol.

EXAMPLE AB12: CO-POLYAMINO ACID AB12—SODIUM POLY-L-GLUTAMATE MODIFIED BY MOLECULE AA8 AND HAVING A NUMBER AVERAGE MOLECULAR WEIGHT (MN) OF 3000 G/MOL

By a method similar to the one used for the preparation of the co-polyamino acid AB1, applied to the hydrochloride salt of molecule AA8 and to a poly-L-glutamic acid obtained by a method similar to the one used for the preparation of the co-polyamino acid AB1-1, a sodium poly-L-glutamate modified by molecule AA8 is obtained.

Dry extract: 19.5 mg/g
DP (estimated based on $^1$H NMR): 26
Based on $^1$H NMR: i=0.04
The calculated average molecular weight of the co-polyamino acid AB12 is 4477 g/mol.
HPLC aqueous-SEC (calibrant PEG): Mn=3000 g/mol.

EXAMPLE AB13: CO-POLYAMINO ACID AB13—SODIUM POLY-L-GLUTAMATE MODIFIED BY MOLECULE AA9 AND HAVING A NUMBER AVERAGE MOLECULAR WEIGHT (MN) OF 3300 G/MOL

By a method similar to the one used for the preparation of the co-polyamino acid AB6, applied to the hydrochloride salt of molecule AA9 and to a poly-L-glutamic acid obtained by a method similar to the one used for the preparation of the co-polyamino acid AB1-1 using isoamylamine as initiator instead of hexylamine, a sodium poly-L-glutamate modified by molecule AA9 is obtained.

Dry extract: 22.3 mg/g
DP (estimated based on $^1$H NMR): 35
Based on $^1$H NMR: i=0.12
The calculated average molecular weight of the co-polyamino acid AB13 is 7226 g/mol.
HPLC aqueous-SEC (calibrant PEG): Mn=3300 g/mol.

EXAMPLE AB21: CO-POLYAMINO ACID AB21—SODIUM POLY-L-GLUTAMATE MODIFIED BY MOLECULE AA7 AND HAVING A NUMBER AVERAGE MOLECULAR WEIGHT (MN) OF 3400 G/MOL

By a method similar to the one used for the preparation of the co-polyamino acid AB6, applied to the hydrochloride salt of molecule AA7 (2.44 g, 2.4 mmol) and to a poly-L-glutamic acid (10 g) obtained by a method similar to the one used for the preparation of the co-polyamino acid AB1-1, a sodium poly-L-glutamate modified by molecule AA7 is obtained.

Dry extract: 22.7 mg/g
DP (estimated based on $^1$H NMR): 22
Based on $^1$H NMR: i=0.056
The calculated average molecular weight of the co-polyamino acid AB21 is 4090 g/mol.
HPLC aqueous-SEC (calibrant PEG): Mn=3400 g/mol.

EXAMPLE AB24: CO-POLYAMINO ACID AB24—SODIUM POLY-L-GLUTAMATE CAPPED AT ONE OF ITS ENDS BY AN ACETYL GROUP AND MODIFIED BY MOLECULE AA1 AND HAVING A NUMBER AVERAGE MOLECULAR WEIGHT (MN) OF 3900 G/MOL

By a method similar to the one used for the preparation of the co-polyamino acid AB6, applied to the hydrochloride salt of molecule AA1 (1.330 g, 3.08 mmol) and to a poly-L-glutamic acid having a relative Mn of 5400 g/mol (4.0 g) obtained by a method similar to the one used for the preparation of the co-polyamino acid AB7-1, a sodium poly-L-glutamate capped at one of its ends by an acetyl group and modified by molecule AA1 is obtained.

Dry extract: 18.7 mg/g
DP (estimated based on $^1$H NMR): 38
Based on $^1$H NMR: i=0.089
The calculated average molecular weight of the co-polyamino acid AB24 is 7088 g/mol.
HPLC aqueous-SEC (calibrant PEG): Mn=3900 g/mol.

EXAMPLE AB25: CO-POLYAMINO ACID AB25—SODIUM POLY-L-GLUTAMATE CAPPED AT ONE OF ITS ENDS BY AN ACETYL GROUP AND MODIFIED BY MOLECULE AA12 AND HAVING A NUMBER AVERAGE MOLECULAR WEIGHT (MN) OF 3700 G/MOL

A poly-L-glutamic acid having a relative average weight Mn of 5400 g/mol and a degree of polymerization of 38 (10.0 g) obtained by a method similar to the one used for the preparation of the co-polyamino acid AB7-1 is solubilized in DMF (420 mL) at 30° C., then maintained at this temperature. In parallel, the hydrochloride salt of molecule AA12 (4.56 g, 11.29 mmol) is dissolved in chloroform (60 mL), and triethylamine (1.14 g, 11.29 mmol) is added. To the solution of co-polyamino acid in DMF, NMM (7.6 g, 75.26 mmol), then HOPO (2.51 g, 22.58 mmol) are added successively. The reaction medium is then cooled to 0° C., then EDC (4.33 g, 22.58 mmol) is added, the mixture is stirred for 1 h at 0° C., then the solution of molecule AA12 is added. The reaction medium is stirred for 2 h between 0° C. and room temperature. The reaction medium is filtered through a woven 0.2-mm filter and poured dropwise onto 3.95 L of water containing 15% by weight of NaCl and HCl (pH 2) under stirring. At the end of the addition, the pH is readjusted to 2 with a 37% HCl solution, and the suspension is allowed to rest overnight. The precipitate is collected by filtration, then solubilized in 780 mL of water by slow addition of a 1 N aqueous NaOH solution until the pH is 7 under stirring. After filtration through a 0.45-μm filter, the solution is diluted by addition of water to obtain a volume of 900 mL, then acetone (485 mL) is added to obtain a solution containing 30% by weight of acetone. This solution is filtered through an activated charcoal filter (3M R53SLP), then acetone is distilled (40° C., 100 mbar). After filtration through a 0.45-μm filter, the product is purified by ultrafiltration against a 0.9% aqueous NaCl solution, a carbonate buffer solution (150 mM), a 0.9% aqueous NaCl solution, a phosphate buffer solution (150 mM), a 0.9% aqueous NaCl solution, then water until the conductimetry of the permeate is less than 50 MS/cm. The solution is then concentrated until a final volume of 600 mL is obtained. The solution is filtered through a 0.2-μm filter and stored at 2-8° C.

Dry extract: 19.7 mg/g
DP (estimated based on $^1$H NMR): 38
Based on $^1$H NMR: i=0.16

The calculated average molecular weight of the co-polyamino acid AB25 is 7877 g/mol.
HPLC aqueous-SEC (calibrant PEG): Mn=3700 g/mol.

EXAMPLE AB28: CO-POLYAMINO ACID AB28—SODIUM POLY-L-GLUTAMATE CAPPED AT ONE OF ITS ENDS BY AN ACETYL GROUP AND MODIFIED BY MOLECULE AA14 AND HAVING A NUMBER AVERAGE MOLECULAR WEIGHT (MN) OF 4700 G/MOL

By a method similar to the one used for the preparation of co-polyamino acid AB6, applied to molecule AA14 (1.51 g, 2.46 mmol) and to a poly-L-glutamic acid having a relative Mn of 5400 g/mol (3.27 g) obtained by a method similar to the one used for the preparation of the co-polyamino acid AB7-1, a sodium poly-L-glutamate capped at one of its ends by an acetyl group modified by molecule AA14 is obtained after purification by ultrafiltration against a 0.9% aqueous NaCl solution, a carbonate buffer solution (150 mM), a 0.9% aqueous NaCl solution, a phosphate buffer solution (150 mM), 0.9% aqueous NaCl solution, then water until the conductimetry of the permeate is less than 50 μS/cm. The solution of co-polyamino acid is then concentrated to approximately 20 g/L theoretical and the pH is adjusted to 7. The aqueous solution is filtered through a 0.2-μm filter and stored at 4° C.

Dry extract: 6.1 mg/g
DP (estimated based on $^1$H NMR): 38
Based on $^1$H NMR: i=0.1

The calculated average molecular weight of the co-polyamino acid AB28 is 8062 g/mol.
HPLC aqueous-SEC (calibrant PEG): Mn=4700 g/mol.
Part B:
BB: Synthesis of the Hydrophobic Molecules in which p=2

The radicals are presented in the following table by the corresponding hydrophobic molecule before grafting onto the co-polyamino acid.

TABLE 1d list of the hydrophobic moleculaes synthesized according to the invention.

| No. | Structure of the hydrophobic molecule before grafting onto the co-polyamino acid |
|---|---|
| BA1 | 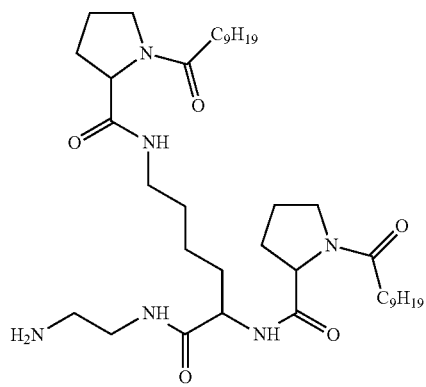 |

TABLE 1d-continued
list of the hydrophobic moleculaes synthesized according to the invention.
| No. | Structure of the hydrophobic molecule before grafting onto the co-polyamino acid |
|---|---|
| BA2 | 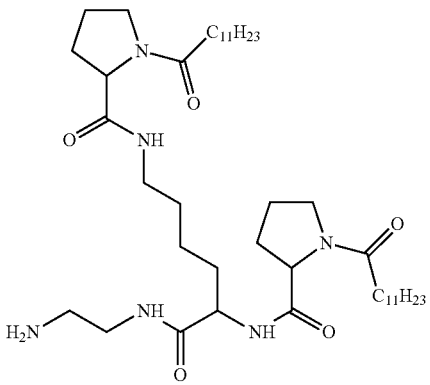 |
| BA3 | 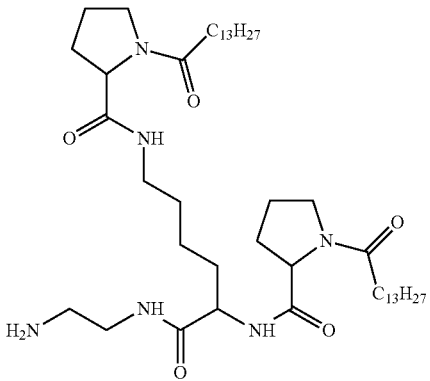 |
| BA4 | 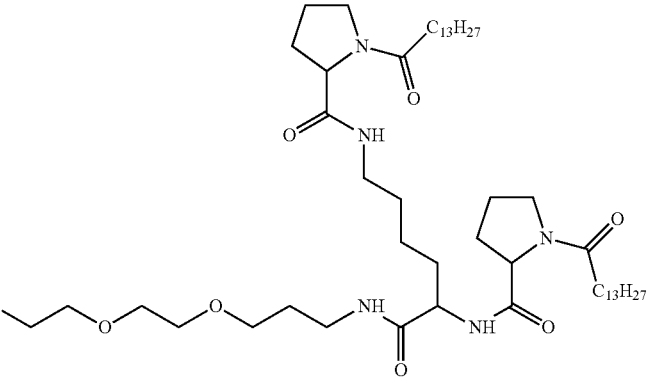 |
| BA5 | 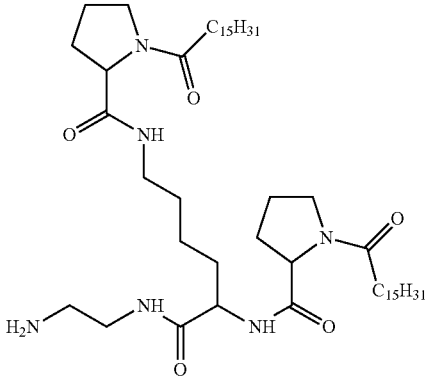 |

TABLE 1d-continued list of the hydrophobic moleculaes synthesized according to the invention.

| No. | Structure of the hydrophobic molecule before grafting onto the co-polyamino acid |
|---|---|
| BA6 | |
| BA7 | |

Part BA: Synthesis of the Hydrophobic Molecules in which p=2

EXAMPLE BA1: MOLECULE BA1

Molecule B1: Product Obtained by the Reaction Between Decanoic Acid and L-proline.

Dicyclohexyl carbodiimide (DCC) (16.29 g, 78.96 mmol) and N-hydroxysuccinimide (NHS) (9.09 g, 78.96 mmol) are successively added to a solution of decanoic acid (14.28 g, 82.91 mmol) in THF (520 mL) at 0° C. After 60 h of stirring at room temperature, the mixture is cooled to 0° C. for 20 min, filtered through a sintered filter. L-Proline (10 g, 86.86 mmol), diisopropylethylamine (DIPEA) (68.8 mL) and water (60 mL) are added to the filtrate. After 24 h of stirring at room temperature, the medium is diluted with water (300 mL). The aqueous phase is washed with ethyl acetate (2×250 mL), acidified to pH~1 with a 1 N aqueous HCl solution, then extracted with dichloromethane (3×150 mL). The combined organic phases are dried over $Na_2SO_4$, filtered, concentrated under a vacuum, and the residue is purified by chromatography on silica gel (cyclohexane, ethyl acetate).

Yield: 14.6 g (69%)

$^1$H NMR (CDCl$_3$, ppm): 0.87 (3H); 1.26 (12H); 1.65 (2H); 2.02 (3H); 2.34 (2H); 2.41 (1H); 3.48 (1H); 3.56 (1H); 4.58 (1H).

LC/MS (ESI): 270.2; (calculated ([M+H]$^+$): 270.4)

Molecule B2: Product Obtained by the Reaction Between Molecule B1 and L-lysine.

By a method similar to the one used for the preparation of molecule B1, applied to molecule B1 (14.57 g, 54.07 mmol) and to L-lysine (4.15 g, 28.39 mmol), a yellow oil is obtained.

Yield: 16.4 g (93%)

$^1$H NMR (CDCl$_3$, ppm): 0.88 (6H); 1.26 (24H); 1.35-1.65 (8H); 1.85-2.35 (12H); 2.53 (0.2H); 2.90 (0.8H); 3.45-3.75 (5H); 4.50-4.70 (3H); 7.82 (1H).

LC/MS (ESI): 649.6; (calculated ([M+H]$^+$): 649.9).

Molecule B3: Product Obtained by Reaction Between Molecule B2 and Boc-ethylenediamine.

DIPEA (8.80 mL) and 2-(1H-benzotriazol-1-yl)-1,1,3,3-tetramethyluronium tetrafluoroborate (TBTU, 8.52 g, 26.54 mmol) at room temperature are added to a solution of molecule 82 (16.4 g, 25.27 mmol) in THF (170 mL). After 30 min of stirring. Boc-ethylenediamine (4.45 g, 27.8 mmol) is added. After stirring at room temperature for 2 h, the solvent is evaporated at reduced pressure and the residue is diluted with ethyl acetate (400 mL). The organic phase is washed with water (250 mL), a saturated aqueous $NaHCO_3$ solution (250 mL), a 1 N aqueous HCl solution (250 mL), a saturated aqueous NaCl solution (250 mL) and dried over $Na_2SO_4$. After filtration and concentration under a vacuum, the residue obtained is purified by chromatography on silica gel (ethyl acetate, methanol) to yield a colorless oil.

Yield: 12.8 g (64%)

$^1$H NMR (CDCl$_3$, ppm): 0.87 (6H); 1.25-1.60 (42H); 1.80-2.05 (4H); 2.15-2.45 (9H); 3.10-3.75 (10H); 4.30 (1H); 4.50 (2H); 5.50 (0.6H); 5.89 (0.2H); 6.15 (0.2H); 7.03 (1H); 7.47 (1H).

LC/MS (ESI): 791.8; (calculated ([M+H]$^+$): 792.1).

Molecule BA1

4 N HCl solution in dioxane (20.2 mL) is added to a solution of molecule B3 (12.78 g, 16.15 mmol) in dichloromethane (110 ml) at 5° C. After 20 h of stirring at 5° C., the medium is concentrated under a vacuum. The residue obtained is dissolved in methanol and evaporated under a vacuum, this operation being repeated 4 times to yield a white solid of molecule BA1 in hydrochloride salt form.

Yield: 11.4 g (97%)

$^1$H NMR (DMSO-d$_6$, ppm): 0.85 (6H); 1.25-1.50 (33H); 1.57 (1H); 1.70-2.40 (12H); 2.82 (2H); 3.00 (2H); 3.25-3.70 (6H); 4.05-4.50 (3H); 7.75-8.45 (6H).

LC/MS (ESI): 691.6; (calculated ([M+H]$^+$): 692.0).

EXAMPLE BA2: MOLECULE BA2

Molecule 4: Product Obtained by the Reaction Between Lauric Acid and L-proline.

By a method similar to the one used for the preparation of molecule B1, applied to lauric acid (31.83 g, 157.9 mmol) and to L-proline (20 g, 173.7 mmol), a yellow oil is obtained.

Yield: 34.3 g (73%)

$^1$H NMR (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI): 298.2; (calculated ([M+H]$^+$): 298.4).

Molecule B5: Product Obtained by the Reaction Between Molecule B4 and L-lysine.

By a method similar to the one used for the preparation of molecule B1, applied to molecule B4 (33.72 g, 113.36 mmol) and to L-lysine (8.70 g, 59.51 mmol), a white solid is obtained.

Yield: 26.2 g (66%)

$^1$H NMR (CDCl$_3$, ppm): 0.88 (6H); 1.26 (321H); 1.35-1.65 (8H); 1.85-2.35 (15H); 2.87 (1H); 3.40-3.75 (5H); 4.50-4.75 (31H); 7.87 (1H).

LC/MS (ESI): 705.6; (calculated ([M+H]$^+$): 706.0).

Molecule B6: Product Obtained by Reaction Between Boc-ethylenediamine and Molecule B5.

By a method similar to the one used for the preparation of molecule B3, applied to molecule B5 (25.74 g, 36.51 mmol) and to Boc-ethylenediamine (6.43 g, 40.16 mmol), a colorless oil is obtained.

Yield: 30.9 g (quantitative)

$^1$H NMR (CDCl$_3$, ppm): 0.88 (6H); 1.35-1.65 (50H); 1.85-2.35 (13H); 3.05-3.75 (10H); 4.25-4.65 (3H); 5.50 (0.4H); 5.88 (0.2H); 6.16 (0.2H); 7.08 (1H); 7.26 (1H); 7.49 (0.2H)

LC/MS (ESI): 847.8; (calculated ([M+H]$^+$): 848.2).

Molecule BA2

After a method similar to the one used for the preparation of molecule BA1, applied to molecule B6 (30.9 g, 36.47 mmol), the residue obtained after concentration under a vacuum is dissolved in methanol and evaporated under a vacuum, this operation being repeated 4 times to yield a white solid of molecule BA2 in hydrochloride salt form after drying at reduced pressure.

Yield: 27.65 g (97%)

$^1$H NMR (DMSO-d$_6$, ppm): 0.85 (6H); 1.10-2.40 (54H); 2.75-3.15 (4H); 3.25-3.60 (6H); 4.05-4.50 (3H); 7.50-8.50 (6H).

LC/MS (ESI): 747.6; (calculated ([M+H]$^+$): 748.1).

EXAMPLE BA3: MOLECULE BA3

Molecule B7: Product Obtained by the Reaction Between Myristic Acid and L-proline.

By a method similar to the one used for the preparation of molecule B1, applied to myristic acid (18.93 g, 82.91 mmol) and to L-proline (10 g, 86.86 mmol), a yellowish oil is obtained.

Yield: 20 g (78%)

$^1$H NMR (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.2; (calculated ([M+H]$^+$): 326.6).

Molecule B8: Product Obtained by the Reaction Between Molecule B7 and L-lysine

By a method similar to the one used for the preparation of molecule B1, applied to molecule B7 (20.02 g, 61.5 mmol) and to L-lysine (4.72 g, 32.29 mmol), a white solid is obtained.

Yield: 12.3 g (53%)

$^1$H NMR (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+1]$^+$): 762.1).

Molecule B9: Product Obtained by the Reaction Between Boc-ethylenediamine and Molecule B8.

By a method similar to the one used for the preparation of molecule B3, applied to molecule B8 (12 g, 15.77 mmol) and to Boc-ethylenediamine (3.03 g, 18.92 mmol), a colorless oil is obtained after purification by column chromatography on silica gel (ethyl acetate, methanol).

Yield: 12.5 g (88%)

$^1$H NMR (DMSO-d$_6$, ppm): 0.85 (6H); 1.20-1.55 (55H); 1.50-2.25 (14H); 2.95-3.10 (6H); 3.31-3.55 (4H); 4.10-4.40 (3H); 6.74 (1H); 7.60-8.25 (3H).

LC/MS (ESI): 904.1; (calculated ([M+H]$^+$): 904.3).

Molecule BA3

By a method similar to the one used for the preparation of molecule BA1, applied to molecule B9 (12.5 g, 13.84 mmol), the residue obtained after concentration under a vacuum is dissolved in methanol and evaporated under a vacuum, this operation being repeated 4 times to yield a white solid of molecule BA3 in hydrochloride salt form after drying at reduced pressure.

Yield: 9.2 g (79%)

$^1$H NMR (DMSO-d$_6$, ppm): 0.85 (6H); 1.10-1.65 (48H); 1.70-2.35 (12H); 2.85 (2H); 3.01 (2H); 3.25-3.65 (6H); 4.10-4.50 (3H); 7.70-8.40 (6H).

LC/MS (ESI): 803.9; (calculated ([M+H]$^+$): 804.2).

EXAMPLE BA4: MOLECULE BA4

Molecule B10: Product Obtained by the Reaction Between Molecule B8 and Boc-1-amino-4,7,10-trioxa-3-tridecane.

By a method similar to the one used for the preparation of molecule B3, applied to molecule B8 (29.80 g, 39.15 mmol) and to Boc-1-amino-4,7,10-trioxa-13-tridecane (15.05 g, 46.96 mmol), a thick colorless oil is obtained.

Yield: 25.3 g (61%)

$^1$H NMR (DMSO-d$_6$, ppm): 0.85 (6H); 1.25-2.35 (75H); 2.85-3.20 (6H); 3.25-3.65 (16H); 4.10-4.45 (3H); 6.38 (0.1H); 6.72 (0.9H); 7.50-8.25 (3H).

LC/MS (ESI): 1064.2; (calculated ([M+H]$^+$: 1064.5).

Molecule BA4

After a method similar to the one used for the preparation of molecule BA1, applied to molecule B10 (25.3 g, 23.8 mmol), the residue obtained after concentration under a vacuum is dissolved in methanol and evaporated under a vacuum, this operation being repeated 4 times to yield a white solid of molecule BA4 in hydrochloride salt form after drying at reduced pressure.

Yield: 20.02 g (84%)

$^1$H NMR (DMSO-d$_6$, ppm): 0.85 (6H); 1.15-2.35 (66H); 2.80-3.20 (6H); 3.30-3.65 (16H); 4.10-4.45 (3H); 7.55-8.60 (6H).

LC/MS (ESI): 964.9; (calculated ([M+H]$^+$): 964.6).

EXAMPLE BA5: MOLECULE BA5

Molecule B11: Product Obtained by Reaction Between Palmitoyl Chloride and L-proline.

By a method similar to the one used for the preparation of molecule A26, applied to palmitoyl chloride (15.39 g, 55.99 mmol) and to L-proline (12.89 &g 111.98 mmol), a white solid of molecule B11 is obtained.

Yield: 19.10 g (96%)

$^1$H NMR (CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

LC/MS (ESI): 354.4; 707.8; (calculated ([M+H]$^+$): 354.3; ([2M+H]$^+$): 707.6).

Molecule B12: Product Obtained by Reaction Between Molecule B11 and L-lysine.

By a method similar to the one used for the preparation of molecule B1, applied to molecule B11 (19.10 g, 54.02 mmol) and to L-lysine (4.15 g, 28.36 mmol), an oily residue is obtained after concentration of the reaction medium at reduced pressure. This residue is diluted in water (150 mL), washed with ethyl acetate (2×75 mL), then the aqueous phase is acidified until the pH is 1 by slow addition of 6 N HCl. The product is extracted 3 times with dichloromethane, the organic phase is dried over Na$_2$SO$_4$, then filtered and concentrated at reduced pressure to yield 11.2 g of yellow oily residue. In parallel, the previous organic phase of ethyl acetate is washed with a 2 N aqueous HCl solution (2×75 mL), a saturated aqueous NaCl solution (75 mL), dried over Na$_2$SO$_4$, filtered and concentrated to yield 10.2 g of yellow oily residue. A white solid is obtained after recrystallization of each one of these residues in acetone.

Yield: 11.83 g (54%)

$^1$H NMR (CDCl$_3$, ppm): 0.87 (6H); 1.06-2.44 (70H); 2.78-2.96 (1H); 3.35-3.75 (5H); 4.28-4.43 (0.1H); 4.43-4.52 (0.2H); 4.52-4.61 (1.8H); 4.61-4.75 (0.9H); 7.74-8.02 (2H).

LC/MS (ESI): 818.0; (calculated ([M+H]$^+$): 818.7).

Molecule B13: Product Obtained by Coupling Between Molecule B12 and Boc-ethylenediamine By a method similar to the one used for the preparation of molecule A27, applied to molecule B12 (18.00 g, 22.02 mmol) in solution in THF and to Boc-ethylenediamine (4.23 g, 26.43 mmol), a white solid is obtained after recrystallization two times in acetonitrile.

Yield: 17.5 g (83%)

$^1$H NMR (DMSO-d$_6$, ppm): 0.85 (6H); 1.15-2.29 (79H); 2.92-3.12 (6H); 3.30-3.59 (4H); 4.06-4.13 (0.65H); 4.16-4.29 (2H); 4.38-4.42 (0.35H); 6.71-6.76 (1H); 7.60-7.69 (1.3H); 7.76-7.81 (0.65H); 7.93-7.97 (0.35H); 8.00-8.04 (0.35H); 8.10-8.17 (0.35H).

LC/MS (ESI): 960.4; (calculated ([M+H]$^+$): 960.8).

Molecule BA5

By a method similar to the one used for the preparation of molecule BA1, applied to molecule B13 (24.4 g, 25.43 mmol), the residue obtained after concentration under a vacuum is solubilized in dichloromethane (150 mL), the organic phase is washed 2 times with a 2 M aqueous sodium hydroxide solution (90 mL). Acetonitrile (120 mL) is added, and the dichloromethane is eliminated by concentration at reduced pressure. The medium is then allowed to rest for 72 h, and a white solid is obtained after filtration and rinsing with acetonitrile, then drying at reduced pressure. This operation is repeated 4 times.

Yield: 14.28 g (65%)

$^1$H NMR (DMSO-d6, ppm): 0.85 (6H); 1.06-2.32 (70H); 2.53-2.63 (2H); 2.89-3.61 (10H); 4.04-4.43 (3H); 7.55-7.62 (0.65H); 7.65-7.72 (0.65H); 7.80 (0.65H); 7.91 (0.35H); 8.03 (0.35H); 8.14-8.23 (0.35H).

LC/MS (ESI): 860.0; (calculated ([M+H]$^+$): 860.8).

EXAMPLE BA6: MOLECULE BA6

Molecule B14: Product Obtained by Coupling Between Molecule A26 and 2,3-diaminopropionic acid By a method similar to the one used for the preparation of molecule B1, applied to molecule A26 (80.00 g, 245.78 mmol) and to 2,3-diaminopropionic dihydrochloride (22.84 g, 129.04 mmol), a white solid is obtained after recrystallization in acetonitrile.

Yield: 69 g (78%)

$^1$H NMR (DMSO-d6, ppm): 0.86 (6H); 1.08-1.38 (40H); 1.40-1.55 (4H); 1.68-2.30 (12H); 3.16-3.66 (6H); 4.20-4.39 (3H); 7.67-8.31 (2H); 12.70 (1H).

LC/MS (ESI): 719.4; 741.5; (calculated ([M+H]$^+$): 719.6; ([M+Na]$^+$): 741.6).

Molecule B15: Product Obtained by Coupling Between Molecule B14 and Boc-ethylenediamine By a method similar to the one used for the preparation of molecule A27, applied to molecule B14 (32.00 g, 44.50 mmol) in solution in dichloromethane and to Boc-ethylenediamine (8.56 g, 53.40 mmol), a colorless oil is obtained after purification by chromatography on silica gel (ethyl acetate, methanol).

Yield: 24.5 g (64%)

$^1$H NMR (DMSO-d6, ppm): 0.85 (6H); 1.16-2.42 (65H); 2.89-3.14 (4H); 3.17-3.66 (6H); 4.11-4.43 (3H); 6.77 (1H); 7.38-8.23 (3H).

LC/MS (ESI): 861.7; (calculated ([M+H]$^+$): 861.7).

Molecule BA6

By a method similar to the one used for the preparation of molecule BA5, applied to molecule B15 (24.50 g, 28.45 mmol), a white solid is obtained after recrystallization in acetonitrile.

Yield: 19.7 g (91%)

$^1$H NMR (DMSO-d6, ppm): 0.85 (6H); 1.10-2.40 (58H); 2.51-2.62 (2H); 2.90-3.16 (2H); 3.16-3.67 (6H); 4.04-4.47 (3H); 7.33-8.27 (3H).

LC/MS (ESI): 761.5; (calculated ([M+H]$^+$): 761.6).

EXAMPLE BA7: MOLECULE BA7

Molecule B16: Product Obtained by the Reaction Between N-(tert-butoxycarbonyl)-1,6-diaminohexane and Molecule B8

By a method similar to the one used for the preparation of molecule A27, applied to molecule B8 (10 g, 13.14 mmol) and to N-(tert-butoxycarbonyl)-1,6-diaminohexane (3.41 g, 15.77 mmol) in dichloromethane, a white solid is obtained after recrystallization in acetonitrile.

Yield: 10.7 g (85%)

$^1$H NMR (CDCl$_3$, ppm): 0.88 (6H); 1.17-2.40 (79H); 3.00-3.71 (10H); 4.26-4.58 (3H); 4.67 (1H); 6.74 (1H); 7.34-7.49 (2H).

LC/MS (ESI): 959.9; (calculated ([M+H]$^+$): 959.8).

Molecule BA7

After a method similar to the one used for the preparation of molecule BA1, applied to molecule B16 (10.5 g, 10.94 mmol), a 2 N aqueous NaOH solution is added dropwise to the reaction medium cooled to 0° C. The aqueous phase is extracted with dichloromethane, then the organic phase is washed 3 times with a 5% aqueous NaCl solution. After drying over $Na_2SO_4$, the organic phase is filtered, concentrated under a vacuum and the residue is recrystallized in acetonitrile.

Yield: 5.4 g (58%)

$^1$H NMR ($CDCl_3$, ppm): 0.88 (6H); 1.19-2.40 (72H); 2.67 (2H); 3.03-3.70 (8H); 4.26-4.57 (3H); 6.71 (1H); 7.39-7.49 (2H).

LC/MS (ESI): 859.8; (calculated ([M+H]$^+$): 859.7).

BB: Synthesis of the Co-Polyamino Acids

Statistical Co-Polyamino Acids of Formulas VII or VIIa

TABLE 1e

| No. | co-polyamino acids bearing carboxylate charges and hydrophobic radicals |
|---|---|
| BB1 | 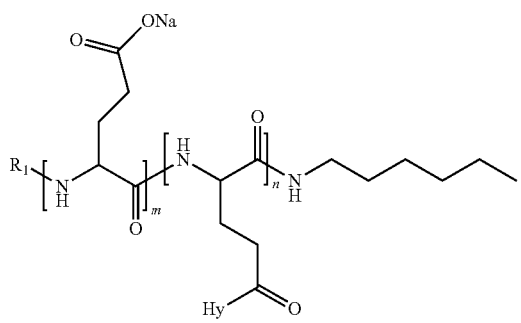<br>i = 0.05, DP (m + n) = 23<br>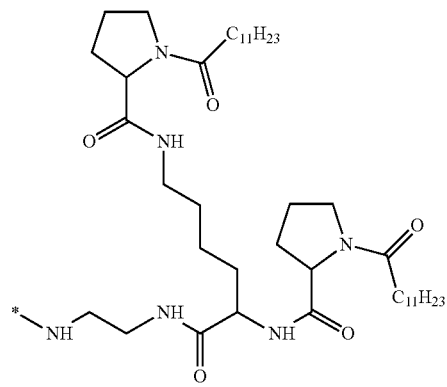<br>Hy =<br>$R_1$ = H or pyroglutamate |
| BB2 | 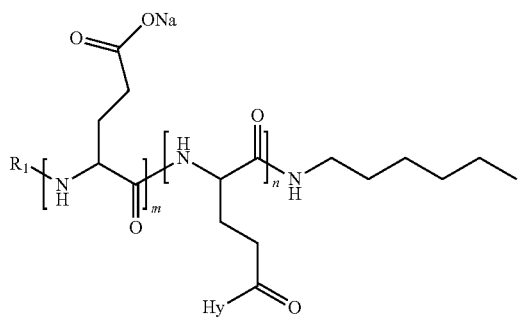<br>i = 0.047, DP (m + n) = 21 |

TABLE 1e-continued
| No. | co-polyamino acids bearing carboxylate charges and hydrophobic radicals |
|---|---|
|  | 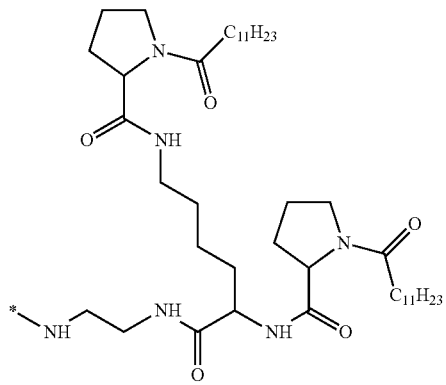 Hy = <br> $R_1$ = H or pyroglutamate |
| BB3 | 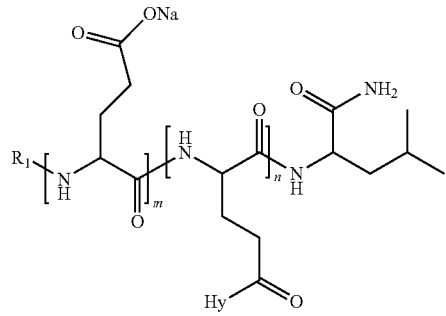 <br> i = 0.049, DP (m + n) = 34 <br> 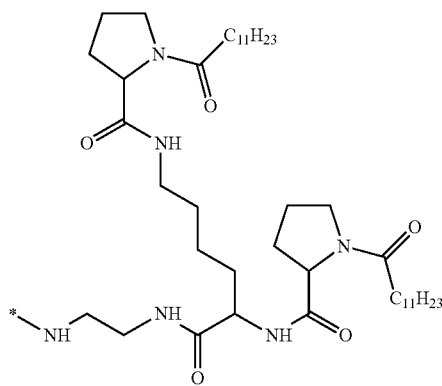 <br> Hy = <br> $R_1$ = H or pyroglutamate |

TABLE 1e-continued
| No. | co-polyamino acids bearing carboxylate charges and hydrophobic radicals |
|---|---|
| BB4 | 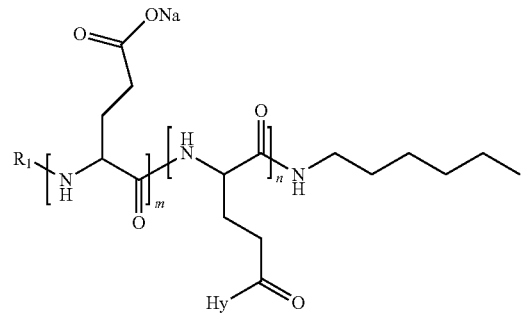<br>i = 0.04, DP (m + n) = 65<br><br>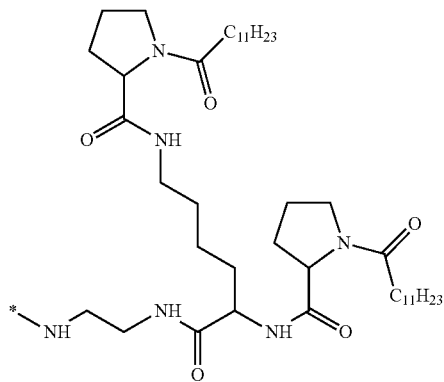<br>Hy =<br>$R_1$ = H or pyroglutamate |
| BB5 | 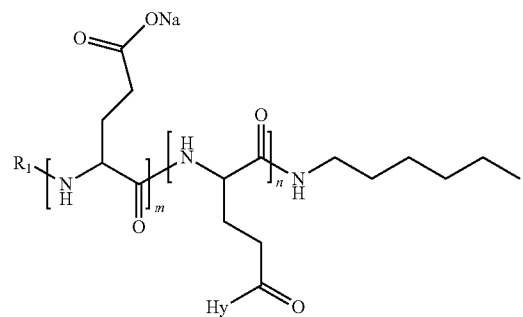<br>i = 0.042, DP (m + n) = 23 |

TABLE 1e-continued
| No. | co-polyamino acids bearing carboxylate charges and hydrophobic radicals |
|-----|------------------------------------------------------------------------|
|     | 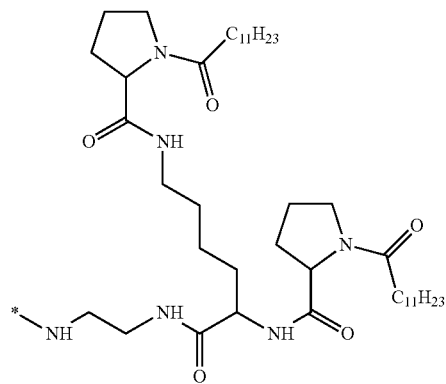 Hy = <br> R1 = CH$_3$—CO—, H or pyroglutamate |
| BB6 | 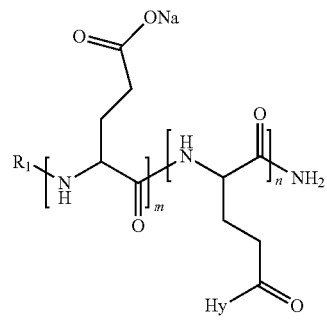 <br> i = 0.04, DP (m + n) = 24 <br><br> 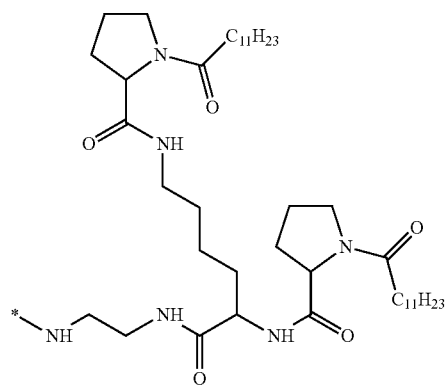 <br> Hy = <br> R1 = CH$_3$—CO—, H or pyroglutamate |

TABLE 1e-continued
| No. | co-polyamino acids bearing carboxylate charges and hydrophobic radicals |
|---|---|
| BB7 | 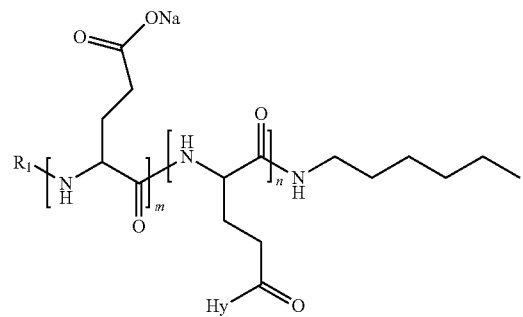<br>i = 0.042, DP (m + n) = 22<br>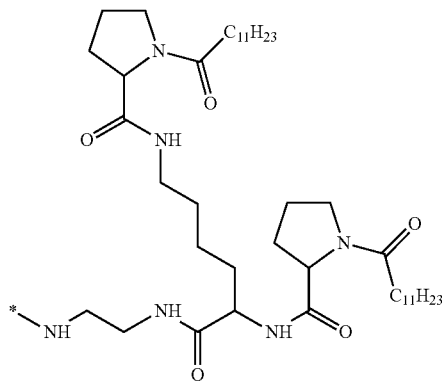<br>Hy =<br>R₁ = H or pyroglutamate |
| BB8 | 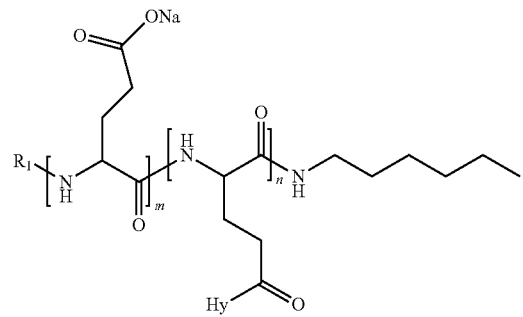<br>i = 0.026, DP (m + n) = 21 |

TABLE 1e-continued
| No. | co-polyamino acids bearing carboxylate charges and hydrophobic radicals |
|---|---|
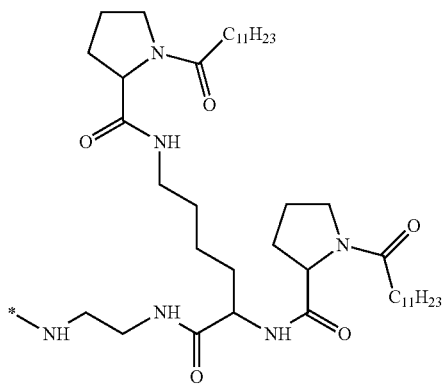
Hy =
R$_1$ = H or pyroglutamate
BB9
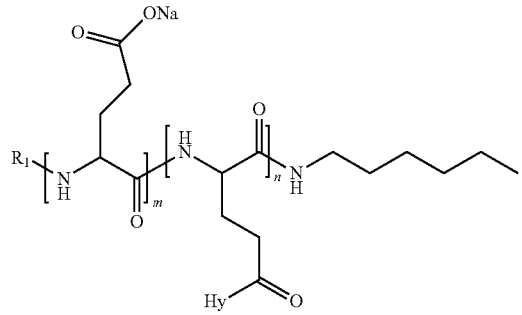
i = 0.05, DP (m + n) = 26
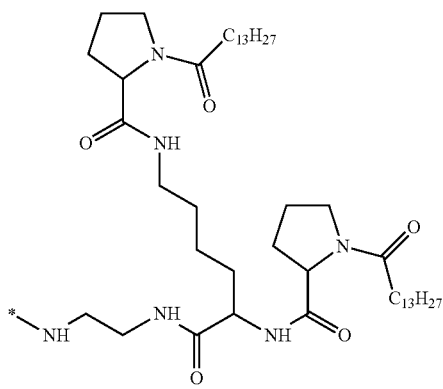
Hy =
R$_1$ = H or pyroglutamate

TABLE 1e-continued
| No. | co-polyamino acids bearing carboxylate charges and hydrophobic radicals |
|---|---|
| BB10 | 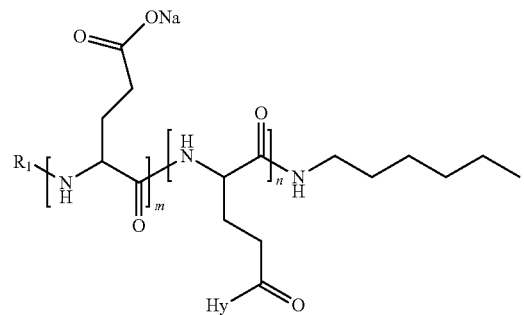
i = 0.029, DP (m + n) = 22
Hy = 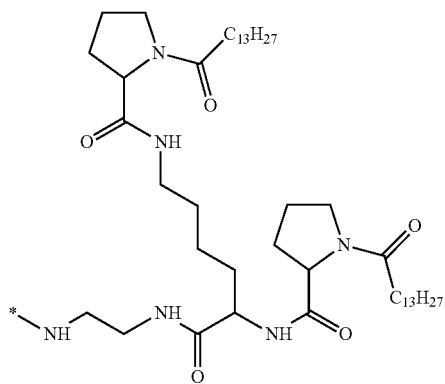
$R_1$ = H or pyroglutamate |
| BB11 | 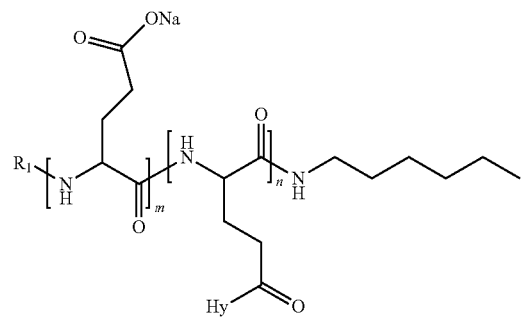
i = 0.032, DP (m + n) = 22 |

TABLE 1e-continued
| No. | co-polyamino acids bearing carboxylate charges and hydrophobic radicals |
|---|---|
| | 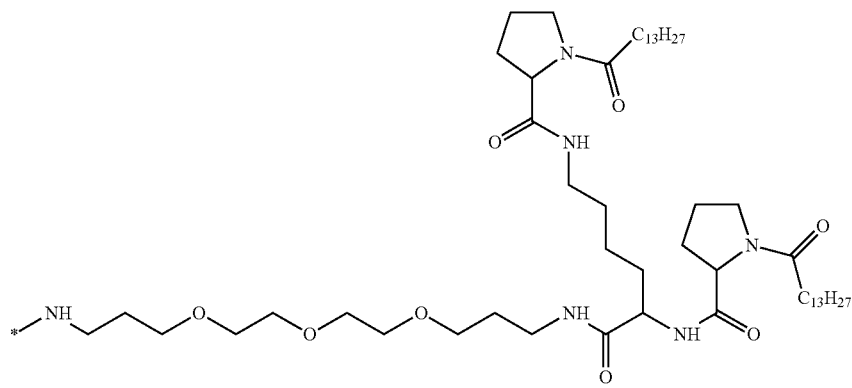<br>Hy =<br>R1 = CH₃—CO—, H or pyroglutamate |
| BB12 | 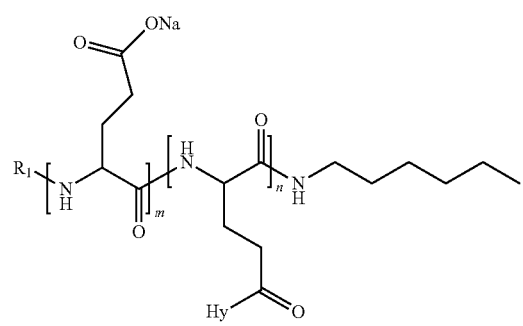<br>i = 0.03, DP (m + n) = 23<br>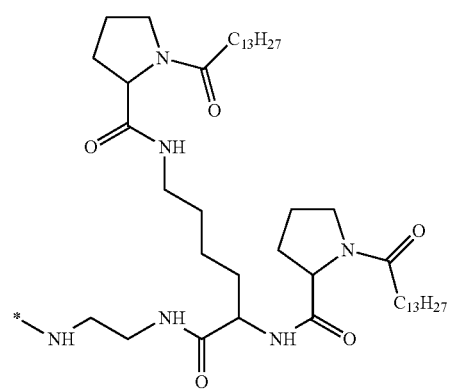<br>Hy =<br>R1 = CH₃—CO—, H or pyroglutamate |

TABLE 1e-continued

| No. | co-polyamino acids bearing carboxylate charges and hydrophobic radicals |
|---|---|
| BB13 | 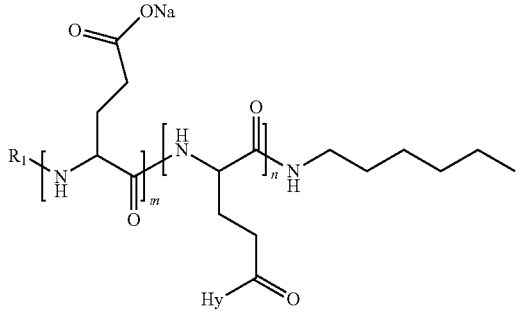 | i = 0.08, DP = 25

Hy = 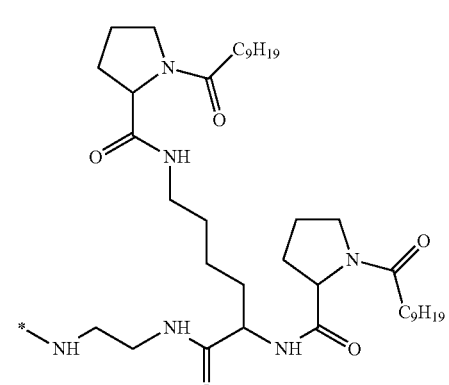

$R_1$ = H or pyroglutamate

Part BB: Synthesis of the Co-Polyamino Acids

EXAMPLE BB1: CO-POLYAMINO ACID BB1—SODIUM POLY-L-GLUTAMATE MODIFIED BY MOLECULE BA2 AND HAVING A NUMBER AVERAGE MOLECULAR WEIGHT (MN) OF 2400 G/MOL

Co-Polyamino Acid BB1-1:

poly-L-glutamic acid having a relative number average molecular weight (Mn) of 3860 g/mol originating from the polymerization of γ-benzyl-L-glutamate N-carboxyanhydride initiated by hexylamine γ-Benzyl-L-glutamate N-carboxyanhydride (90.0 g, 342 mmol) is placed for 30 min under a vacuum in a round-bottom flask dried beforehand in the oven, then anhydrous DMF (465 mL) is introduced. The mixture is then stirred under argon until the dissolution is complete, cooled to 4° C., then hexylamine (1.8 mL, 14 mmol) is introduced rapidly. The mixture is stirred between 4° C. and room temperature for 2 days. The reaction mixture is then heated at 65° C. for 4 h, cooled to room temperature, then poured dropwise into cold diisopropyl ether (6 L) under stirring. The white precipitate is recovered by filtration, washed with diisopropyl ether (500 mL, then 250 mL), then dried under a vacuum at 30° C. to yield a poly(γ-benzyl-L-glutamic) acid (PBLG).

A 33% hydrobromic acid solution (HBr) in acetic acid (135 mL, 0.77 mol) is added dropwise to a solution of PBLG (42.1 g) in trifluoroacetic acid (TFA, 325 mL) at 4° C. The mixture is stirred at room temperature for 2 h, then poured dropwise onto a 1:1 (v/v) mixture of diisopropyl ether and water under stirring (1.6 L). After 1 h 30 of stirring, the heterogeneous mixture is allowed to rest overnight. The white precipitate is recovered by filtration, washed with a 1:1 (v/v) mixture of diisopropyl ether and water (200 mL).

The solid obtained is then solubilized in water (1 L) by adjusting the pH to 7 by addition of a 10 N aqueous sodium hydroxide solution, then a 1 N aqueous sodium hydroxide solution. After solubilization, the theoretical concentration is adjusted to 25 g/L theoretical by addition of water to obtain a final volume of 1.5 L.

The solution is filtered through a 0.45-μm filter, then purified by ultrafiltration against a 0.9% NaCl solution, then water until the conductimetry of the permeate is less than 50 μS/cm.

The aqueous solution is then acidified by addition of 37% hydrochloric acid solution until the pH is 2. After 4 h of stirring, the precipitate obtained is filtered, then dried under a vacuum at 30° C. to yield a poly-L-glutamic acid having a number average molecular weight (Mn) of 3860 g/mol with respect to a polyoxyethylene standard (PEG).

Co-Polyamino Acid BB1

The co-polyamino acid BB-1 (10.0 g) is solubilized in DMF (700 mL) at 30-40° C., then cooled to 0° C. The hydrochloride salt of molecule BA2 (2.95 g, 3.8 mmol) is suspended in DMF (45 mL), and triethylamine (0.39 g, 3.8 mmol) is then added to this suspension, then the mixture is heated slightly under stirring until the dissolution is complete. N-Methylmorpholine (NMM, 7.6 g, 75 mmol) in DMF (14 mL) and ethyl chloroformate (ECF, 8.1 g, 75 mmol) are added to the solution of co-polyamino acid at 0° C. After 10 min at 0° C., the solution of molecule BA2 is added and the medium is maintained at 30° C. for 1 h. The reaction medium is poured dropwise onto 6 L of water containing 15% by weight of sodium chloride and HCl (pH 2), then it is allowed to rest overnight. The precipitate is collected by filtration, washed by the sodium chloride solution at pH 2 (1 L) and dried under a vacuum for approximately 1 h. The white solid obtained is taken up in water (600 mL) and the pH is adjusted to 7 by slow addition of a 1 N aqueous NaOH solution. The volume is adjusted to 700 mL by addition of water. After filtration through a 0.45-µm filter, the clear solution obtained is purified by ultrafiltration against a 0.9% NaCl solution, then water until the conductimetry of the permeate is less than 50 µS/cm. After discharging, the solution is filtered through a 0.2-µm filter and stored at 2-8° C.

Dry extract: 19.7 mg/g
DP (estimated based on $^1$H NMR): 23
Based on $^1$H NMR: i=6.05
The calculated average molecular weight of the co-polyamino acid BB1 is 4350 g/mol.
HPLC aqueous-SEC (calibrant PEG): Mn=2400 g/mol.

EXAMPLE BB2: CO-POLYAMINO ACID BB2—SODIUM POLY-L-GLUTAMATE MODIFIED BY MOLECULE BA2 AND HAVING A NUMBER AVERAGE MOLECULAR WEIGHT (MN) OF 4900 G/MOL

A poly-L-glutamic acid having a number average molecular weight (Mn) of 4100 g/mol (5.0 g) obtained by a method similar to the one used for the preparation of the co-polyamino acid BB1-1 is solubilized in DMF (205 mL) at 30-40° C., then maintained at this temperature. In parallel, the hydrochloride salt of molecule BA2 (1.44 g, 1.84 mmol) is suspended in DMF (10 mL), and triethylamine (0.19 g, 1.84 mmol) is added, then the mixture is heated slightly under stirring until the dissolution is complete. To the solution of co-polyamino acid in DMF, NMM (3.7 g, 36.7 mmol), the solution of molecule BA2, then 2-hydroxypyridine N-oxide (HOPO, 0.31 g, 2.76 mmol) are added successively. The reaction medium is then cooled to 0° C., then EDC (0.53 g, 2.76 mmol) is added and the temperature of the medium is raised again to room temperature for 3 h. The reaction medium is poured dropwise onto 1.55 L of water containing 15% by weight of NaCl and HCl (pH 2) under stirring. At the end of the addition, the pH is readjusted to 2 with a 1 N HCl solution, and the suspension is about to rest overnight. The precipitate is collected by filtration, then rinsed with 100 mL of water. The white solid obtained is dissolved in 200 mL of water by slow addition of a 1 N aqueous NaOH solution until the pH is 7 under stirring, then the solution is filtered through a 0.45-µm filter. The clear solution obtained is purified by ultrafiltration against a 0.9% NaCl solution, then water until the conductimetry of the permeate is less than 50 µS/cm. The solution obtained is filtered through a 0.2-µm filter and stored at 2-8° C.

Dry extract: 16.3 mg/g
DP (estimated based on $^1$H NMR): 21
Based on $^1$H NMR: i=0.047
The calculated average molecular weight of the co-polyamino acid BB2 is 3932 g/mol.
HPLC aqueous-SEC (calibrant PEG): Mn=4900 g/mol.

EXAMPLE BB3; CO-POLYAMINO ACID BB3—SODIUM POLY-L-GLUTAMATE MODIFIED BY MOLECULE BA2 AND HAVING A NUMBER AVERAGE MOLECULAR WEIGHT (MN) OF 6400 G/MOL

Co-Polyamino Acid BB3-1:
poly-L-glutamic acid having a number average molecular weight (Mn) of 17500 g/mol, originating from the polymerization of γ-methyl-L-glutamate N-carboxyanhydride initiated by L-leucinamide.

A poly-L-glutamic acid having a relative number average weight (Mn) of 17500 g/mol at a methyl polymethacrylate standard (PMMA) is obtained by polymerization of the γ-methyl N-carboxyanhydride of glutamic acid using L-leucinamide as initiator and carrying out a deprotection of the methyl esters by using a 37% hydrochloric acid solution according to the method described in the patent application FR-A-2 801 226.

By a method similar to the one used for the preparation of the co-polyamino acid BB2, applied to the hydrochloride salt of molecule BA2 (3.23 g, 4.1 mmol) and to the co-polyamino acid BB3-1 (11 g), a sodium poly-L-glutamate modified by molecule BA2 is obtained.

Dry extract: 27.5 mg/g
DP (estimated based on $^1$H NMR): 34
Based on $^1$H NMR: li=0.049
The calculated average molecular weight of the co-polyamino acid BB3 is 6405 g/mol.
HPLC aqueous-SEC (calibrant PEG): Mn=6400 g/mol.

EXAMPLE BB4: CO-POLYAMINO ACID BB4—SODIUM POLY-L-GLUTAMATE MODIFIED BY MOLECULE BA2 AND HAVING A NUMBER AVERAGE MOLECULAR WEIGHT (MN) OF 10500 G/MOL

By a method similar to the one used for the preparation of the co-polyamino acid BB2, applied to the hydrochloride salt of molecule BA2 (5 g, 6.35 mmol) and to a poly-L-glutamic acid having a number average molecular weight Mn=10800 g/mol (21.7 g) obtained by a method similar to the one used for the preparation of the co-polyamino acid BB1-1, a sodium poly-L-glutamate modified by molecule BA2 is obtained.

Dry extract: 28.2 mg/g
DP (estimated based on $^1$H NMR): 65
Based on $^1$H NMR: i=0.04
The calculated average molecular weight of the co-polyamino acid BB4 is 11721 g/mol.
HPLC aqueous-SEC (calibrant PEG): Mn=10500 g/mol.

EXAMPLE BB5: CO-POLYAMINO ACID BB5—SODIUM POLY-L-GLUTAMATE CAPPED AT ONE OF ITS ENDS BY AN ACETYL GROUP AND MODIFIED BY MOLECULE BA2 AND HAVING A NUMBER AVERAGE MOLECULAR WEIGHT (MN) OF 3600 G/MOL

Co-Polyamino Acid. BB5-1:
poly-L-glutamic acid having a Mn of 3700 g/mol originating from the polymerization of γ-benzyl-L-glutamate N-carboxyanhydride initiated by hexylamine and capped at one of its ends by an acetyl group.

γ-Benzyl-L-glutamate N-carboxyanhydride (100.0 g, 380 mmol) is placed under a vacuum for 30 minutes in a round-bottom flask dried beforehand in the oven, then anhydrous DMF (250 mL) is introduced. The mixture is then stirred under argon until the dissolution is complete, cooled to 4° C., then hexylamine (2.3 mL, 17 mmol) is introduced rapidly. The mixture is stirred between 4° C. and room temperature for 2 days, then precipitated in diisopropyl ether (3.4 L). The precipitate is recovered by filtration, washed two times with diisopropyl ether (225 mL), then dried to yield a white solid which is dissolved in 450 mL of THF. To this solution, N,N-diisopropylethylamine (DIPEA, 31 mL, 176 mmol), then acetic anhydride (17 mL, 176 mmol) are added successively. After one night of stirring at room temperature, the solution is poured slowly into diisopropyl ether (3 L) over a duration of 30 min and under stirring. After 1 h of stirring, the precipitate is filtered, washed two times with diisopropyl ether (200 mL), then dried under a vacuum at 30° C. to yield a poly(γ-benzyl-L-glutamic) acid capped at one of its ends by an acetyl group.

A 33% hydrobromic acid solution (HBr) in acetic acid (235 mL, 1.34 mol) is added dropwise to a solution of capped co-polyamino acid (72 g) in trifluoroacetic acid (TFA, 335 mL) at 4° C. The mixture is stirred at room temperature for 3 h 30, then poured dropwise onto a 1:1 (v/v) mixture of diisopropyl ether and water under stirring (4 L). After 2 h of stirring, the heterogeneous mixture is allowed to rest overnight. The white precipitate is recovered by filtration, washed with a 1:1 (v/v) mixture of diisopropyl ether and water (340 mL) then with water (340 mL). The solid obtained is then solubilized in water (1.5 L) by adjusting the pH to 7 by addition of a 10 N aqueous sodium hydroxide solution, then a 1 N aqueous sodium hydroxide solution. After solubilization, the theoretical concentration is adjusted to 20 g/L theoretical by addition of water to obtain a final volume of 2.1 L. The solution is filtered through a 0.45-μm filter, then purified by ultrafiltration against a 0.9% NaCl solution, then water until the conductimetry of the permeate is less than 50 μS/cm. The solution of co-polyamino acid is then concentrated until a final volume of 1.8 L is obtained. The aqueous solution is then acidified by addition of 37% hydrochloric acid solution until the pH is 2. After 4 h of stirring, the precipitate obtained is filtered, washed with water (330 mL), then dried under a vacuum at 30° C. to yield a poly-L-glutamic acid having a number average molecular weight (Mn) of 3700 g/mol with respect to a polyoxyethylene standard (PEG).

Co-Polyamino Acid BB5

By a method similar to the one used for the preparation of the co-polyamino acid BB2, applied to the hydrochloride salt of molecule BA2 (6.92 g, 8.8 mmol) and to the co-polyamino acid BB5-1 (30.0 g), a sodium poly-L-glutamate capped at one of its ends by an acetyl group and modified by molecule BA2 is obtained.

Dry extract: 29.4 mg/g
DP (estimated based on $^1$H NMR): 23
Based on $^1$H NMR: i=0.042
The calculated average molecular weight of the co-polyamino acid BB5 is 4302 g/mol.
HPLC aqueous-SEC (calibrant PEG): Mn=3600 g/mol.

EXAMPLE BB6: CO-POLYAMINO ACID BB6—SODIUM POLY-L-GLUTAMATE CAPPED AT ONE OF ITS ENDS BY AN ACETYL GROUP AND MODIFIED BY MOLECULE BA2 AND HAVING A NUMBER AVERAGE MOLECULAR WEIGHT (MN) OF 4100 G/MOL

By a method similar to the one used for the preparation of the co-polyamino acid BB2, applied to the hydrochloride salt of molecule BA2 (5.8 g, 7.4 mmol) and to a poly-L-glutamic acid having a number average molecular weight Mn=3800 g/mol (25 g) obtained by a method similar to the one used for the preparation of the co-polyamino acid BB5-1 using ammonia instead of hexylamine, a sodium poly-L-glutamate capped at one of its ends by an acetyl group and modified by molecule BA2 is obtained.

Dry extract: 27.6 mg/g
DP (estimated based on $^1$H NMR): 24
Based on $^1$H NMR: i=0.04
The calculated average molecular weight of the co-polyamino acid BB6 is 4387 g/mol.
HPLC aqueous-SEC (calibrant PEG): Mn=4100 g/mol.

EXAMPLE BB7: CO-POLYAMINO ACID BB7—SODIUM POLY-L-GLUTAMATE MODIFIED BY MOLECULE BA2 AND HAVING A NUMBER AVERAGE MOLECULAR WEIGHT (MN) OF 4200 G/MOL

By a method similar to the one used for the preparation of the co-polyamino acid BB2, applied to the hydrochloride salt of molecule BA2 (7.07 g, 9.0 mmol) and to a poly-L-glutamic acid having a number average molecular weight Mn=3600 g/mol (30.0 g) obtained by a method similar to the one used for the preparation of the co-polyamino acid BB1-1, a sodium poly-L-glutamate modified by molecule BA2 is obtained.

Dry extract: 28.3 mg/g
DP (estimated based on $^1$H NMR): 22
Based on $^1$H NMR: i=0.042
The calculated average molecular weight of the co-polyamino acid BB7 is 4039 g/mol.
HPLC aqueous-SEC (calibrant PEG): Mn=4200 g/mol.

EXAMPLE BB8: CO-POLYAMINO ACID BB5—SODIUM POLY-L-GLUTAMATE MODIFIED BY MOLECULE BA2 AND HAVING A NUMBER AVERAGE MOLECULAR WEIGHT (MN) OF 5200 G/MOL

By a method similar to the one used for the preparation of the co-polyamino acid BB2, applied to the hydrochloride salt of molecule BA2 (0.85 g, 1.1 mmol) and to a poly-L-glutamic acid having a number average molecular weight Mn=4100 g/mol (5.0 g) obtained by a method similar to the one used for the preparation of the co-polyamino acid BB1-1, a sodium poly-L-glutamate modified by molecule BA2 is obtained.

Dry extract: 28.6 mg/g
DP (estimated based on $^1$H NMR): 21
Based on $^1$H NMR: i=0.026
The calculated average molecular weight of the co-polyamino acid BB8 is 3620 g/mol.
HPLC aqueous-SEC (calibrant PEG): Mn=5200 g/mol.

EXAMPLE BB9: CO-POLYAMINO ACID BB9—SODIUM POLY-L-GLUTAMATE MODIFIED BY MOLECULE BA3 AND HAVING A NUMBER AVERAGE MOLECULAR WEIGHT (MN) OF 4700 G/MOL

By a method similar to the one used for the preparation of the co-polyamino acid BB2, applied to the hydrochloride salt of molecule BA3 (3.05 g, 3.6 mmol) and to a poly-L-glutamic acid having a number average molecular weight Mn=4100 g/mol (10.0 g) obtained by a method similar to the one used for the preparation of the co-polyamino acid BB1-1, a sodium poly-L-glutamate modified by molecule BA3 is obtained.

Dry extract: 28.6 mg/g
DP (estimated based on $^1$H NMR): 26
Based on $^1$H NMR: i=0.05
The calculated average molecular weight of the co-polyamino acid BB9 is 4982 g/mol.
HPLC aqueous-SEC (calibrant PEG): Mn=4700 g/mol.

EXAMPLE BB10: CO-POLYAMINO ACID BB10—SODIUM POLY-L-GLUTAMATE MODIFIED BY MOLECULE BA3 AND HAVING A NUMBER AVERAGE MOLECULAR WEIGHT (MN) OF 4200 G/MOL

By a method similar to the one used for the preparation of the co-polyamino acid BB2, applied to the hydrochloride salt of molecule BA3 (1.90 g, 2.3 mmol) and to a poly-L-glutamic acid having a number average molecular weight Mn=3500 g/mol (10.0 g) obtained by a method similar to the one used for the preparation of the co-polyamino acid BB1-1, a sodium poly-L-glutamate modified by molecule BA3 is obtained.

Dry extract: 25.9 mg/g
DP (estimated based on $^1$H NMR): 22
Based on $^1$H NMR: i=0.029
The calculated average molecular weight of the co-polyamino acid BB10 is 3872 g/mol.
HPLC aqueous-SEC (calibrant PEG): Mn=4200 g/mol.

EXAMPLE BB11: CO-POLYAMINO ACID BB11—SODIUM POLY-L-GLUTAMATE CAPPED AT ONE OF ITS ENDS BY AN ACETYL GROUP AND MODIFIED BY MOLECULE BA4 AND HAVING A NUMBER AVERAGE MOLECULAR WEIGHT (MN) OF 3900 G/MOL

By a method similar to the one used for the preparation of the co-polyamino acid BB2, applied to the hydrochloride salt of molecule BA4 (2.21 g, 2.2 mmol) and to a poly-L-glutamic acid having a number average weight Mn=3700 g/mol (10 g) obtained by a method similar to the one used for the preparation of the co-polyamino acid BB5-1, a sodium poly-L-glutamate capped at one of its ends by an acetyl group and modified by molecule BA4 is obtained.

Dry extract: 28.1 mg/g
DP (estimated based on $^1$H NMR): 22
Based on $^1$H NMR: i=0.032
The calculated average molecular weight of the co-polyamino acid BB11 is 4118 g/mol.
HPLC aqueous-SEC (calibrant PEG): Mn=3900 g/mol.

EXAMPLE BB12: CO-POLYAMINO ACID BB12—SODIUM POLY-L-GLUTAMATE CAPPED AT ONE OF ITS ENDS BY AN ACETYL GROUP AND MODIFIED BY MOLECULE BA3 AND HAVING A NUMBER AVERAGE MOLECULAR WEIGHT (MN) OF 3900 G/MOL

By a method similar to the one used for the preparation of the co-polyamino acid BB2, applied to the hydrochloride salt of molecule BA3 (1.9 g, 2.3 mmol) and to a poly-L-glutamic acid having a number average weight Mn=3600 g/mol (10 g) obtained by a method similar to the one used for the preparation of co-polyamino acid BB5-1, a sodium poly-L-glutamate capped at one of its ends by an acetyl group and modified by molecule BA3 is obtained.

Dry extract: 26.7 mg/g
DP (estimated based on $^1$H NMR): 23
Based on $^1$H NMR: i=0.03
The calculated average molecular weight of the co-polyamino acid BB12 is 4145 g/mol.
HPLC aqueous-SEC (calibrant PEG): Mn=3900 g/mol.

EXAMPLE BB13: CO-POLYAMINO ACID BB13—SODIUM POLY-L-GLUTAMATE MODIFIED BY MOLECULE BA1 AND HAVING A NUMBER AVERAGE MOLECULAR WEIGHT (MN) OF 2800 G/MOL

By a method similar to the one used for the preparation of the co-polyamino acid BB1, applied to the hydrochloride salt of molecule BA1 (3.65 g, 5 mmol) and to a poly-L-glutamic acid having a number average molecular weight Mn=3600 g/mol (10 g) obtained by a method similar to the one used for the preparation of the co-polyamino acid BB1-1, a sodium poly-L-glutamate modified by molecule BA1 is obtained.

Dry extract: 25.6 mg/g
DP (estimated based on $^1$H NMR): 25
Based on $^1$H NMR: i=0.08
The calculated average molecular weight of the co-polyamino acid BB13 is 5253 g/mol.
HPLC aqueous-SEC (calibrant PEG): Mn=2800 g/mol.

Part C:
The glucagon used is human glucagon originating from a peptide synthesis process. It originates from the company Bachem (reference 407473).

EXAMPLE C1: SOLUTION OF GLUCAGON AT 2 MG/ML

Powdered glucagon (80 mg) is introduced into a 45-mL flask. A 0.003 N aqueous hydrochloric acid solution (40 mL) is added. The glucagon powder is mixed by repeated inversions of the tube until the dissolution of the glucagon is complete. The solution of glucagon at 2 mg/mL is then filtered through a membrane (0.22 μm).

EXAMPLE C2: SOLUTION OF GLUCAGON AT 4 MG/ML

Powdered glucagon (160 mg) is introduced into a 45-mL flask. A 0.006 N aqueous hydrochloric acid solution (40 mL) is added. The glucagon powder is mixed by repeated inversions of the tube until the dissolution of the glucagon is complete. The solution of glucagon at 4 mg/mL is then filtered through a membrane (0.22 μm).

EXAMPLE C3: SOLUTION OF GLUCAGON AT 6 MG/ML

Powdered glucagon (240 mg) is introduced into a 45-mL flask. A 0.01 N aqueous hydrochloric acid solution (40 mL) is added. The glucagon powder is mixed by repeated inversions of the tube until the dissolution of the glucagon is complete. The solution of glucagon at 6 mg/mL is then filtered through a membrane (0.22 μm).

EXAMPLE C4: SOLUTION OF GLUCAGON AT 10 MG/ML

Powdered glucagon (400 mg) is introduced into a 45-mL flask. A 0.01 N aqueous hydrochloric acid solution (40 mL)

is added. The glucagon powder is mixed by repeated inversions of the tube until the dissolution of the glucagon is complete. The solution of glucagon at 10 mg/mL is then filtered through a membrane (0.22 μm).

Tests were carried out to verify whether the polyamino acids make it possible to solubilize the glucagon, and the minimum concentration of co-polyamino acid necessary to solubilize the glucagon was determined.

EXAMPLE CA2: COMPOSITIONS OF CO-POLYAMINO ACID AB21 AT VARIABLE CONCENTRATIONS AND GLUCAGON CONCENTRATION OF 1 MG/ML

X' mg of co-polyamino acid AB21 were weighed on a precision scale, and 2 mL of a 10 mM phosphate buffer solution comprising m-cresol (46 mM), glycerol (548 mM) were added. The composition is stirred until dissolution of the co-polyamino acid, then the solution is filtered through a membrane (0.22 μm).

2 mL of a glucagon solution as prepared in Example C1 are mixed at 2 mL of the solution of co-polyamino acid as prepared above, leading to a composition comprising X mg/mL of co-polyamino acid and 1 mg/mL of glucagon.

A visual inspection was carried out to determine whether or not a clear solution was obtained. The result of the minimum concentration is presented in Table 5.

EXAMPLE CA4: COMPOSITION OF CO-POLYAMINO ACID BB2 AT VARIABLE CONCENTRATIONS AND A GLUCAGON CONCENTRATION OF 1 MG/ML

In the same manner as described in Example CA2, compositions comprising X mg/mL of co-polyamino acid BB2 and 1 mg/mL of glucagon are prepared.

A visual inspection was carried out to determine whether or not a clear solution was obtained. The result of the minimum concentration is presented in Table 5.

EXAMPLE CA6: COMPOSITION OF CO-POLYAMINO ACID BB9 AT VARIABLE CONCENTRATIONS AND A GLUCAGON CONCENTRATION OF 1 MG/ML

In the same manner as described in Example CA2, compositions comprising X mg/mL of co-polyamino acids BB9 and 1 mg/mL of glucagon are prepared.

A visual inspection was carried out to determine whether or not a clear solution was obtained. The result of the minimum concentration is presented in Table 5.

TABLE 5

Minimum concentration of co-polyamino acid (in mg/mL) for the solubilization of human glucagon (1 mg/mL).

| Example | Co-polyamino acid | Minimum concentration (x mg/mL) of co-polyamino acid (in mg/mL) for the solubilization of human glucagon (1 mg/mL) |
|---|---|---|
| CA2 | AB21 | ≤1.25 |
| CA4 | BB2 | ≤0.82 |
| CA6 | BB9 | ≤1.25 |

Concentration series were prepared with co-polyamino acids according to the invention, leading to the obtention of the following stable solutions.

EXAMPLE CB2: SOLUTION OF CO-POLYAMINO ACID AB1 AT 15 MG/ML AND OF GLUCAGON AT 1 MG/ML 60 mg of co-polyamino acid AB1 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 μm).

2 mL of a glucagon solution as prepared in Example C1 are mixed with 2 mL of the solution of co-polyamino acid AB1 as prepared above. Then three samples of 1 mL each of this solution are prepared and placed under static conditions at 37° C.

EXAMPLE CB3: SOLUTION OF CO-POLYAMINO ACID AB5 AT 10 MG/ML AND OF GLUCAGON AT 1 MG/ML 40 mg of co-polyamino acid AB5 are weighed on a precision scale, and 2 mL of a 10 mM phosphate buffer solution comprising m-cresol (46 mM), glycerol (548 mM) are added. The composition is stirred until dissolution of the co-polyamino acid, then the solution is filtered through a membrane (0.22 μm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB4: SOLUTION OF CO-POLYAMINO ACID AB7 AT 8.6 MG/ML AND OF GLUCAGON AT 1 MG/ML 34.4 mg of co-polyamino acid AB7 are weighed on a precision scale, and 2 mL of a 10 mM phosphate buffer solution comprising m-cresol (46 mM), glycerol (548 mM) are added. The composition is stirred until dissolution of the co-polyamino acid, then the solution is filtered through a membrane (0.22 μm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB8: SOLUTION OF CO-POLYAMINO ACID BB2 AT 8 MG/ML AND OF GLUCAGON AT 1 MG/ML 32 mg of co-polyamino acid BB2 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 μm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB9: SOLUTION OF CO-POLYAMINO ACID BB5 AT 9 MG/ML AND OF GLUCAGON AT 1 MG/ML 36 mg of co-polyamino acid BB5 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB10: SOLUTION OF CO-POLYAMINO ACID BB7 AT 15.4 MG/ML AND OF GLUCAGON AT 1 MG/ML 61.6 mg of co-polyamino acid BB7 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 rpm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB11: SOLUTION OF CO-POLYAMINO ACID BB AT 7.6 MG/ML AND OF GLUCAGON AT 1 MG/ML 30.4 mg of co-polyamino acid BB8 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C are mixed with 2 mL of the solution of co-polyamino acid as prepared above. Then three samples of 1 mL each of this solution are prepared and placed under static conditions at 37° C.

EXAMPLE CB12: SOLUTION OF CO-POLYAMINO ACID BB9 AT 4.3 MG/ML AND OF GLUCAGON AT 1 MG/ML 17.2 mg of co-polyamino acid BB9 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB13: SOLUTION OF CO-POLYAMINO ACID BB11 AT 5.9 MG/ML AND OF GLUCAGON AT 1 mg/mL 23.6 mg of co-polyamino acid BB11 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB14: SOLUTION OF CO-POLYAMINO ACID BB11 AT 8.6 MG/ML AND OF GLUCAGON AT 1 MG/ML 34.4 mg of co-polyamino acid BB11 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C1 are mixed with 2 mL of the solution of co-polyamino acid as prepared above. Then three samples of 1 mL each of this solution are prepared and placed under static conditions at 37° C.

EXAMPLE CB25: SOLUTION OF CO-POLYAMINO ACID AB21 AT 8.6 MG/ML AND OF GLUCAGON AT 1 MG/ML 34.4 mg of co-polyamino acid AB21 are weighed on a precision scale and added to 2 mL of a 10 mM phosphate buffer solution comprising m-cresol (46 mM), glycerol (548 mM). The composition is stirred until dissolution of the co-polyamino acid, then the solution is filtered through a membrane (0.22 µm).

2 mL of a glucagon solution as prepared in Example C1 are mixed with 2 mL of the solution of co-polyamino acid as prepared above. Then three samples of 1 mL each of this solution are prepared and placed under static conditions at 37° C.

Part C'—Counter-Example Formulations

The cetyltrimethylammonium bromide (CTAB) originates from the company Sigma-Aldrich (ref A6909).

The dodecyl maltoside (DDM) originates from the company Sigma-Aldrich (ref D4641).

The name (mPEG-DSPE 2000) originates from the company Interchim (ref KVS081).

The myristoyl lysophosphatidyl choline (LMPC) originates from the company Combi-Block (ref: QE-2488).

In a manner similar to the composition described in Example CA2, compositions CEC1 to CEC10 are also prepared in a manner so as to obtain the desired concentrations (Table 6d).

TABLE 6d compositions of glucagon at 1 mg/mL at pH 7.2 in the presence of commercial products at different concentrations.

| Compositions | Glucagon (mg/mL) | Products of the prior art | concentration (mg/mL) | Phosphate buffer (mM) | pH |
|---|---|---|---|---|---|
| CEC1 | 1 | CTAB | 0.3 | 2 | 7.13 |
| CEC2 | 1 | CTAB | 15.7 | 2 | 7.14 |
| CEC3 | 1 | CTAB | 39.3 | 2 | 7.16 |
| CEC4 | 1 | DDM | 0.4 | 2 | ND |
| CEC5 | 1 | DDM | 3.2 | 2 | 7.15 |
| CEC6 | 1 | DDM | 10.7 | 2 | 7.34 |

TABLE 6d-continued compositions of glucagon at 1 mg/mL at pH 7.2 in the
presence of commercial products at different concentrations.

| Compositions | Glucagon (mg/mL) | Products of the prior art | concentration (mg/mL) | Phosphate buffer (mM) | pH |
|---|---|---|---|---|---|
| CEC7 | 1 | PEG-DSPE | 2.4 | 2 | 7.20 |
| CEC8 | 1 | PEG-DSPE | 10.9 | 2 | 7.12 |
| CEC9 | 1 | LMPC | 0.4 | 2 | ND |
| CEC10 | 1 | LMPC | 2.1 | 2 | 7.13 |

Part D: Stability

EXAMPLE D1: PHYSICAL STABILITY OF COMPOSITIONS OF CO-POLYAMINO ACID/GLUCAGON

The visual inspection of the samples placed under static conditions at 37° C. is carried out at 0, 7, 14 and 21 days at 37° C. in order to detect the appearance of visible particles or turbidity. This inspection is carried out according to the recommendations of the European Pharmacopoeia (EP 2.9.20): the samples are subjected to illumination of at least 2000 lux and are observed on a white background and a black background. When particles are visible in at least 2 of the 3 samples, the composition is considered unstable. Thus, stable means that on the day of inspection at least 2 samples were free of particles.

The results of the visual inspections are reported in the following Table 7.

The study of the physical stabilities of the compositions of Examples CB2 to CEC9 described in the table below was carried out on volumes of 1 mL of composition in flasks having a capacity of 3 mL (Adelphi—ref: VCDIN2RDLS1).

EXAMPLE D2: CHEMICAL STABILITY OF COMPOSITIONS OF CO-POLYAMINO ACID/GLUCAGON

An RP-HPLC method adapted based on the USP instructions was used to determine the concentration of glucagon and of its degradation products. This method was used in order to evaluate the chemical stability of the glucagon of the compositions. The HPLC conditions are as follows:

Column: 4.6×150 mm, C-18

Mobile phase A: Solution S/acetonitrile 80/20 (v/v), solution S being a 150 mM potassium dihydrogenophosphate solution in water, adjusted to pH 2.7 with an 85% phosphoric acid solution Mobile phase B: water/acetonitrile 60/40 (v/v)

Mobile phase C: water/acetonitrile 10/90 (v/v)

Column temperature: 45° C.

Detection: UV 210 nm

Temperature of the autosampler: 4° C.

The recovery was measured on samples at 7, 14 and 21 days at 37° C. under static conditions. The chemical stability data, that is to say the glucagon recovery obtained by RP-HPLC, is presented in the following Table 8.

The study of the chemical stabilities of the compositions described in the table below was carried out on compositions in flasks (1 mL of composition in flask having a capacity of 3 mL (Adelphi—ref: VCDIN2RDLS1)).

TABLE 7

Results of the visual inspections of compositions comprising a co-polyamino acid and glucagon

| Example | Co-Polyamino acid and product of the prior art (mg/mL) | Glucagon (mg/mL) | Exenatide (mg/mL) | L-methionine (mg/mL) | Stable at 7 days | Stable at 14 days | Stable at 21 days |
|---|---|---|---|---|---|---|---|
| CB2 | AB1 (15) | 1 | 0 | 0 | yes | no | no |
| CB3 | AB5 (10) | 1 | 0 | 0 | yes | yes | yes |
| CB4 | AB7 (8.6) | 1 | 0 | 0 | yes | yes | yes |
| CB8 | BB2 (8) | 1 | 0 | 0 | yes | yes | yes |
| CB9 | BB5 (9) | 1 | 0 | 0 | yes | yes | no |
| CB10 | BB7 (15.4) | 1 | 0 | 0 | yes | yes | yes |
| CB11 | BB8 (7.6) | 1 | 0 | 0 | yes | no | no |
| CB12 | BB9 (4.3) | 1 | 0 | 0 | yes | yes | yes |
| CB13 | BB11 (5.9) | 1 | 0 | 0 | yes | yes | no |
| CB14 | BB11 (8.6) | 1 | 0 | 0 | yes | yes | yes |
| CB25 | AB21 (8.6) | 1 | 0 | 0 | yes | yes | yes |
| CB26 | AB24 (6.1) | 1 | 0 | 0 | yes | yes | yes |
| CB27 | AB24 (3.0) | 1 | 0 | 0 | yes | yes | yes |
| CB30 | AB25 (6.7) | 1 | 0 | 0 | yes | yes | yes |
| CB31 | AB28 (6.9) | 1 | 0 | 0 | yes | yes | — |
| CEC1 | CTAB (0.3) | 1 | 0 | 0 | No | — | — |
| CEC6 | DDM (10.7) | 1 | 0 | 0 | No | — | — |
| CEC7 | mPEG-DSPE (2.4) | 1 | 0 | 0 | No | — | — |
| CEC9 | LMPC (0.4) | 1 | 0 | 0 | No | — | — |
| CEC10 | LPMC (2.1) | 1 | 0 | 0 | No | — | — |

"—" means not observed

TABLE 8

Measurements of recovery of compositions comprising a co-polyamino acid and glucagon

| Example | Co-Polyamino acid (mg/mL) | Glucagon (mg/mL) | Exenatide (mg/mL) | L-methionine (mg/mL) | Recovery at 7 days | Recovery at 14 days | Recovery at 21 days |
|---|---|---|---|---|---|---|---|
| CB4 | AB7 (8.6) | 1 | 0 | 0 | ≥95 | ≥90 | ≥85 |
| CB8 | BB2 (8) | 1 | 0 | 0 | — | ≥90 | ≥90 |
| CB10 | BB7 (15.4) | 1 | 0 | 0 | ≥95 | ≥90 | — |
| CB14 | BB11 (8-6) | 1 | 0 | 0 | ≥95 | ≥90 | ≥90 |
| CB25 | AB21 (8.6) | 1 | 0 | 0 | — | ≥90 | ≥85 |
| CB30 | AB25 | 1 | 0 | 0 | — | ≥90 | — |
| CEC2 | CTAB | 1 | 0 | 0 | — | <50 | |

"—" means not measured

Principle

The poor stability of a peptide can lead to the formation of amyloid fibrils defined as ordered macromolecular structures. These structures can possibly result from the formation of gel within the sample.

The test of monitoring the fluorescence of Thioflavin T (ThT) is used in order to analyze the physical stability of the solutions. Thioflavin is a small molecule probe that has a characteristic fluorescence signature when it binds to fibrils of the amyloid type (Naiki et al. (1989) Anal. BioChem. 177, 244-249, LeVine (1999) Methods. Enzymol. 309, 274-284). This method makes it possible to monitor the formation of fibrils for low ThT concentrations within undiluted solutions. This monitoring is carried out under accelerated stability conditions: under stirring and at 37° C.

Experimental Conditions

The samples are prepared just before the start of the measurement. The preparation of each composition is described in the associated example. Thioflavin T was added to the composition from a concentrated stock solution so as to induce a negligible dilution of the composition. The concentration of Thioflavin T in the composition is 40 µM.

A volume of 150 µL of the composition was introduced into a well of a 96-well plate, then 2.7 µL of concentrated ThT solution was introduced. Each composition was analyzed in three tests (triplicate) conducted on one plate. The plate was sealed with transparent film in order to prevent the evaporation of the composition.

This plate was then placed into the enclosure of a plate reader (EnVision 2104 Multilabel, Perkin Elmer). The temperature was regulated at 37° C., and a lateral stirring at 960 rpm with amplitude 1 mm was carried out.

A reading of the fluorescence intensity in each well was carried out with an excitation wavelength of 442 nm and an emission wavelength of 482 nm over time.

The fibril formation process manifests itself in a strong increase in fluorescence after a delay referred to as lag time. The lag time is determined visually, taking into consideration the time when the fluorescence signal starts to increase significantly above the baseline.

The lag time value reported corresponds to the average of the lag time measurements conducted on three wells.

The lag time results obtained are presented in the table below.

The results are presented in Table 9 below

TABLE 9 results of the latency times obtained with the compositions of co-polyamino acid or commercial products in the presence of 1 mg/mL of glucagon.

| Composition | Glucagon mg/mL | BC | Concentration by weight mg/mL | Latency time in hours |
|---|---|---|---|---|
| CB26 | 1 | AB24 | 6.1 | >68 |
| CB30 | 1 | AB25 | 6.7 | >68 |
| CB31 | 1 | AB28 | 6.9 | >63 |
| CEC7 | 1 | mPEG-DSPE | 2.4 | 2.6 |
| CEC9 | 1 | LMPC | 0.4 | 3.7 |

The latency times obtained with the compositions of co-polyamino acid in the presence of glucagon are higher than those of the formulations of commercial products in the presence of glucagon.

Compositions in the Form of an Injectable Aqueous Solution Comprising Human Glucagon and a Co-Polyamino Acid The invention thus relates to physically stable compositions in the form of an injectable aqueous solution, the pH of which is from 6.0 to 8.0, comprising at least:
a) human glucagon, and
b) a co-polyamino acid bearing carboxylate charges and hydrophobic radicals Hy, In an embodiment, the compositions according to the invention comprise, in addition, a gastrointestinal hormone.

The invention claimed is:
1. A composition in the form of an injectable aqueous solution, the pH of which is from 6.0 to 8.0, comprising at least:
a) human glucagon;
b) a co-polyamino acid consisting of glutamic or aspartic units, bearing carboxylate charges and hydrophobic radicals Hy, and said hydrophobic radicals Hy being radicals of the following formula I:

Formula I in which

GpR is a radical of formula II:

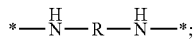

II

GpA is a radical of formula III or III':

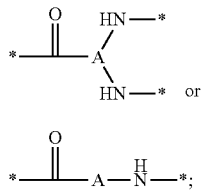

GpC is a radical of formula IV:

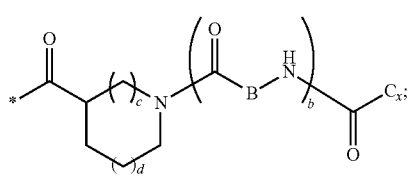

IV the * indicate the sites of attachment of the different groups bound by amide functions;
a is a whole number equal to 0 or 1;
b is a whole number equal to 0 or 1;
p is a whole number equal to 1 or 2, and
   if p is equal to 1, then a is equal to 0 or 1 and GpA is a radical of formula III', and
   if p is equal to 2, then a is equal to 1 and GpA is a radical of formula III;
c is a whole number equal to 0 or 1, and, if c is equal to 0, then d is equal to 1 or 2;
d is a whole number equal to 0, to 1 or 2;
r is a whole number equal to 0 or 1, and
   if r is equal to 0, then the hydrophobic radical of formula I is bound to the co-polyamino acid via a covalent bond between a carbonyl of the hydrophobic radical and a nitrogen atom in the N-terminal position of the co-polyamino acid, thus forming an amide function originating from the reaction of an amine function in N-terminal position of the precursor of the co-polyamino acid and an acid function borne by the precursor of the hydrophobic radical, and
   if r is equal to 1, then the hydrophobic radical of formula I is bound to the co-polyamino acid:
      via a covalent bond between a nitrogen atom of the hydrophobic radical and a carbonyl of the co-polyamino acid therefore forming an amide function originating from the reaction between an amine function of the precursor of the hydrophobic radical and an acid function borne by the precursor of the co-polyamino acid, or
      via a covalent bond between a carbonyl of the hydrophobic radical and a nitrogen atom in N-terminal position of the co-polyamino acid therefore forming an amide function originating from the reaction of an acid function of the precursor of the hydrophobic radical and an amine function in N terminal position borne by the precursor of the co-polyamino acid;

R is a radical selected from the group consisting of:
   a linear or branched divalent alkyl radical comprising, if GpR is a radical of formula II, from 2 to 12 carbon atoms;
   a linear or branched divalent alkyl radical comprising, if GpR is a radical of formula II, from 2 to 11 carbon atoms, said alkyl radical bearing one or more —CONH₂ functions, and
   an unsubstituted ether or polyether radical comprising from 4 to 14 carbon atoms and from 1 to 5 oxygen atoms;

A is a linear or branched alkyl radical comprising from 1 to 6 carbon atoms;

B is a linear or branched alkyl radical, optionally comprising an aromatic ring, comprising from 1 to 9 carbon atoms;

$C_x$ is a linear or branched monovalent alkyl radical, in which x indicates the number of carbon atoms, and:
   if p is equal to 1, x is from 11 to 25 ($11 \leq x \leq 25$);
   if p is equal to 2, x is from 9 to 15 ($9 \leq x \leq 15$), the ratio i between the number of hydrophobic radicals and the number of glutamic or aspartic units being between $0 < i \leq 0.5$;

when several hydrophobic radicals are borne by a co-polyamino acid, then they are identical or different, the degree of polymerization DP in glutamic or aspartic units is from 10 to 250;

the free acid functions being in the form of a salt of an alkaline cation selected from the group consisting of $Na^+$ and $K^+$.

2. The composition according to claim 1, wherein said hydrophobic radicals are selected from the hydrophobic radicals of formula I in which p=1, represented by the following formula V:

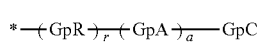

formula V wherein GpR, GpA, GpC, r and a have the definitions given above.

3. The composition according to claim 1, wherein said hydrophobic radicals are selected from the hydrophobic radicals of formula I in which a=1 and p=2, represented by the following formula VI:

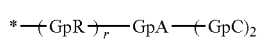

Formula VI wherein
GpR, GpA, GpC, r and a have the definitions given above.

4. The composition according to claim 1, wherein the co-polyamino acid bearing carboxylate charges and hydrophobic radicals is selected from the co-polyamino acids of the following formula VIIa:

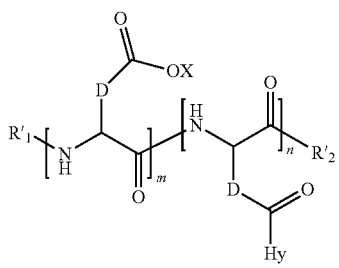

Formula VIIa in which,
- D represents, independently, either a —CH₂— group (aspartic unit) or a —CH₂—CH₂— group (glutamic unit),
- Hy is a hydrophobic radical selected from the hydrophobic radicals of formula I, V or VI, in which r=1 and GpR is a radical of Formula II,
- X represents an H or a cationic entity selected from the group comprising the metal cations;
- n+m represents the degree of polymerization DP of the co-polyamino acid, that is to say the average number of monomer units per chain and 5≤n+m≤250; R'1 is a radical selected from the group consisting of H, a C2 to C10 linear acyl group, a C4 to C10 branched acyl group, benzyl, a terminal "amino acid" unit and a pyroglutamate,
- R'2 is a —NR'R" radical, R' and R", which are identical or different, being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms, selected from the group consisting of O, N and S.

5. The composition according to claim 4, wherein co-polyamino acid bearing carboxylate charges and hydrophobic charges is selected from the co-polyamino acids of formulas VII in which R₁=R'₁ and R₂=R'₂ of the following formula VIIa:

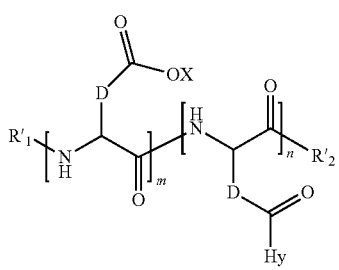

Formula VIIa in which
- m, n, X, D and Hy have the definitions given above,
- R'₁ is a radical selected from the group consisting of H, a C2 to C10 linear acyl group, a C4 to C10 branched acyl group, benzyl, a terminal "amino acid" unit and a pyroglutamate,
- R'₂ is a —NR'R" radical, R' and R", which are identical or different, being selected from the group consisting of H, the C2 to C10 linear or branched or cyclic alkyls, benzyl, and said alkyl R' and R" together optionally forming one or more saturated, unsaturated and/or aromatic rings and/or optionally comprising heteroatoms, selected from the group consisting of O, N and S.

6. The composition according to claim 4, wherein the co-polyamino acid bearing carboxylate charges and hydrophobic radicals is selected from the co-polyamino acids of formula VII or VIIa in which the at least one co-polyamino acid is selected from the co-polyamino acids in which group D is a —CH₂— group (aspartic unit).

7. The composition according to claim 4, wherein the co-polyamino acid bearing carboxylate charges and hydrophobic radicals is selected from the co-polyamino acids of formulas VII or VIIa in which the at least one co-polyamino acid is selected from the co-polyamino acids in which group D is a group —CH₂—CH₂— (glutamic unit).

8. The composition according to claim 1, wherein the concentration of co-polyamino acid bearing carboxylate charges and hydrophobic radicals is at most 40 mg/mL.

9. The composition according to claim 1, wherein the concentration of human glucagon is from 0.25 to 5 mg/mL.

10. The composition according to claim 1, wherein the molar ratio [hydrophobic radical]/[human glucagon] is less than 15.

11. The composition according to claim 1, wherein the composition comprises, in addition, a polyanionic compound.

12. The composition according to claim 1, wherein the composition comprises, in addition, a zinc salt.

13. The composition according to claim 1, wherein the composition comprises, in addition, a gastrointestinal hormone.

14. The composition according to claim 13, wherein the gastrointestinal hormone is selected from the group consisting of exenatide, liraglutide, lixisenatide, albiglutide and dulaglutide, their analogs or derivatives and their pharmaceutically acceptable salts thereof.

15. The composition according to claim 13, wherein the concentration of gastrointestinal hormone is within an interval from 0.01 to 10 mg/mL.

* * * * *